United States Patent [19]

Apple et al.

[11] Patent Number: 5,451,512
[45] Date of Patent: Sep. 19, 1995

[54] METHODS AND REAGENTS FOR HLA CLASS I A LOCUS DNA TYPING

[75] Inventors: Raymond J. Apple, San Francisco; Teodorica L. Bugawan, Castro Valley; Henry A. Erlich, Oakland, all of Calif.

[73] Assignee: Hoffmann-La Roche Inc., Nutley, N.J.

[21] Appl. No.: 127,954

[22] Filed: Sep. 28, 1993

Related U.S. Application Data

[63] Continuation-in-part of Ser. No. 788,113, Nov. 5, 1991, abandoned.

[51] Int. Cl.$^6$ .................. C12P 19/34; C12Q 1/68; C07H 21/04
[52] U.S. Cl. ........................... 435/91.2; 435/6; 536/23.5; 536/24.33
[58] Field of Search ............. 435/6, 91.2; 935/77, 935/78; 536/23.5, 24.33

[56] References Cited

U.S. PATENT DOCUMENTS 4,965,188 10/1990 Mullis et al. .................... 435/6

FOREIGN PATENT DOCUMENTS 0354580 2/1990 European Pat. Off. .
9207956 5/1992 WIPO .
9219771 11/1992 WIPO .

OTHER PUBLICATIONS

Parham et al, J. Immunology 142:3937–395 (1989).
Malissen et al., Feb., 1982, "Exon/Intron Organization and Complete Nucleotide Sequence of an HLA Gene" Proc. Natl. Acad. Sci. USA 79:893–897.
Saiki et al., Nov., 1986, "Analysis of Enzymatically Amplified B-Globin and HLA-DQalpha DNA With Allele-Specific Oligonucleotide Probes" Nature 324(13):163–166.
Bjorkman and Parham, 1990, "Structure, Function, and Diversity of Class I Major Histocompatibility Complex Molecules" Annu. Rev. Biochem. 59:253–288.
Zemmour and Parham, 1991, "HLA Class I Nucleotide Sequences, 1991" Immunogenetics 33:310–320.
Baxter-Lowe et al., Aug., 1989, "HLA Gene Amplification and Hybridization Analysis of Polymorphism HLA Matching for Bone Marrow Transplantation of a Patient With HLA-Deficient Severe Combined Immunodeficiency Syndrome" J. Clin. Invest. 84:613–618.
Lawlor et al., Feb. 1991, "Ancient HLA Genes From 7,500–Year–Old Archaeological Remains" Nature 349:785–788.
Ennis et al., Apr., 1990, "Rapid Cloning of HLA-A, B cDNA Using the Polymerase Chain Reaction: Frequency and Nature of Errors Produced in Amplification" Proc. Natl. Acad. Sci. USA 87:2833–2837.
Hill et al., 1991, "HLA Class I Typing by PCR: HLA-B27 and an African B27 Subtype" Lancet 337:640–642.
Fernandez-Vina et al., 1992, "DNA Typing for HLA Class I Alleles: I. Subsets of HLA-A2 and of -A48" Human Immunology 33:163–173.
Browning et al., 1993, "Tissue Typing the HLA-A Locus From Genomic DNA by Sequenc-Specific PCR: Comparison of HLA Genotype and Surface Expression on Colorectal Tumor Cell Lines" Proc. Natl. Acad. Sci. USA 90:2842–2845.
Oh et al., 1993, "Isoelectric Focusing Subtypes of HLA-A can be Defined by Oligonucleotide Typing" Tissue Antigens 41:135–142.
Yoshida et al., 1992, "Polymerase-Chain Reaction-Based Analysis of Polymorphism in the HLA-B Gene" Human Immunology 34:257–266.

Primary Examiner—Margaret Parr
Assistant Examiner—Eggerton Campbell
Attorney, Agent, or Firm—George M. Gould; Stacey R. Sias; Douglas A. Petry

[57] ABSTRACT

Primers for amplification of specific nucleic acid sequences of the second and third exon of HLA Class I A gene and probes for identifying polymorphic sequences contained in the amplified DNA can be used in processes for typing homozygous or heterozygous samples from a variety of sources and for detecting allelic variants not distinguishable by serological methods. This HLA-A DNA typing system can be used in a forward or reverse dot-blot format that is simple and rapid to perform, produces detectable signals in minutes, and can be used for tissue typing, determining individual identity, and identifying disease susceptible individuals.

2 Claims, 2 Drawing Sheets

Figure 1

Exon 2 HLA-A

| | A | | | | | B | | | | C | | | | | D | | | | | E | | | | | |
|---|---|---|---|---|---|---|---|---|---|---|---|---|---|---|---|---|---|---|---|---|---|---|---|---|---|
| | YFYTSS | YFFTSS | YFFTSS | YFSTSS | RGKPR | AASQK | AASRR | AASQR | QERPE | WDQET | WDGET | WDEET | WDLQT | WDRNT | TRNMK | TRNVK | NTRNV | KAHSQ | KAQSQ | HRVDL | DRVDL | DRANL | DRENL | DRESL | IALR |
| 0101 | | + | | | + | | | | + | | | | | | + | | | + | | | | | | | |
| 0201 | | + | | | | | + | | | + | | | | | | | | + | | + | | | | | |
| 0202 | | + | | | | + | | | | + | | | | | | | | + | | + | | | | | |
| 0203 | | + | | | | | + | | | + | | | | | | | | + | | + | | | | | |
| 0204 | | + | | | | | + | | | + | | | | | | | | + | | + | | | | | |
| 0205 | + | | | | | + | | | | + | | | | | | | | + | | + | | | | | |
| 0206 | + | | | | | | + | | | + | | | | | | | | + | | + | | | | | |
| 0210 | + | | | | | | + | | | + | | | | | | | | + | | + | | | | | |
| 0211 | | + | | | | | + | | | + | | | | | | | | + | | | | + | | | |
| 0212 | | + | | | | | + | | | + | | | | | | | | + | | + | | | | | |
| 0301 | | + | | | | | + | | | | + | | | | | + | | | + | + | | | | | |
| 0302 | | + | | | | | + | | | | + | | | | | + | | | + | + | | | | | |
| 1101 | + | | | | | | + | | | | + | | | | | + | | | + | + | | | | | |
| 1102 | + | | | + | | | + | | | | + | | | | | + | | | + | + | | | | | |
| 2301 | | | + | | | | + | | | | | + | | | | + | | | | | | | + | | + |
| 2401 | | | + | | | | + | | | | | + | | | | + | | | | | | | + | | + |
| 2402 | | | + | | | | + | | | | | + | | | | + | | | | | | | + | | + |
| 2403 | | | + | | | | + | | | | | + | | | | + | | | | | | | + | | + |
| 2501 | + | | | | | | + | | | | | | + | | | + | + | | | | | | + | + | |
| 2601 | + | | | | | | + | | | | | | + | | | + | + | | | | | + | | | |
| 2901 | | | + | | | | + | | | | | | + | | | + | | | + | | | + | | | |
| 2902 | | | + | | | | + | | | | | | + | | | + | | | + | | | + | | | |
| 3001 | | + | | | | | + | + | + | | | | | | | + | | | + | + | | | | | |
| 3002 | | | + | | | | + | + | + | | | | | | | + | | + | | | | | + | | |
| 3003 | | | + | | | | + | + | | | | | | | | + | | + | | | | | + | | |
| 3101 | | | + | | | | + | + | + | | | | | | | + | | + | | | + | | | | |
| 3201 | | + | | | | | + | + | | | | | | | | + | | + | | | | | | + | |
| 3301 | | | + | | | | + | | | | | + | | | | + | | + | + | | | | | | |
| 3401 | + | | | | | | + | | | | | + | | | | + | | | + | + | | | | | |
| 3402 | + | | | | | | + | | | | | + | | | | + | | + | | + | | | | | |
| 3601 | | | + | | | + | | | | + | | | | + | | | | + | | | | + | | | |
| 4301 | + | | | | | | + | | | | | | + | | | + | | + | | + | | | | | |
| 6601 | + | | | | | | + | | | | | | + | | | + | + | | + | + | | | | | |
| 6602 | + | | | | | | + | | | | | | + | | | + | + | | + | + | | | | | |
| 6801 | + | | | | | | + | | | | | | + | | | + | + | | + | + | | | | | |
| 6802 | + | | | | | | + | | | | | | + | | | + | + | | + | + | | | | | |
| 6901 | + | | | | | | + | | | | | | + | | | + | + | | + | + | | | | | |
| 7401 | | + | | | | | + | | + | | | | | | | + | | + | | + | | | | | |

Figure 2

Exon 3 HLA-A

| | | | | F | | | | G | | | H | | | I | | | | J | | | | | | | |
|---|---|---|---|---|---|---|---|---|---|---|---|---|---|---|---|---|---|---|---|---|---|---|---|---|---|
| | G S H T L Q | G S H T I Q | L Q M M F G | T I Q I M | H T V Q R M | H T I Q M M | H T V Q M M | G Y H Q Y | Y Q Q D A | G Y E Q H | Q I T K R K | Q T T K H K | Q I T Q R | A A H V A | E A A H E A | T A H E A | V H A | E Q L R A Y | E Q Q R A Y | E Q W R A Y | E Q Q R R V Y | E G R C V | C V D G L | S D W R | S D G R |
| 0101 | | + | | + | | | | | | | + | | | | | + | | | | | | + | + | + | |
| 0201 | | | | + | | | | + | | | + | | | + | | | | + | | | | | | + | |
| 0202 | + | | | | | | | + | | | + | | | + | | | | | | + | | | | + | |
| 0203 | | | | + | | | | + | | | + | | | | + | | | | | + | | | | + | |
| 0204 | | | | | | | + | + | | | + | | | + | | | | + | | | | | | + | |
| 0205 | + | | | | | | | + | | | + | | | + | | | | | | + | | | | + | |
| 0206 | | | | + | | | | + | | | + | | | + | | | | + | | | | | | + | |
| 0210 | | | | + | | | | + | | | + | | | + | | | | + | | | | | | | + |
| 0211 | | | | + | | | | + | | | + | | | + | | | | + | | | | | | + | |
| 0212 | | | | + | | | | + | | | + | | | + | | | | | + | | | | | + | |
| 0301 | | + | + | | | | | + | | | | | | | + | | | + | | | | | | | + |
| 0302 | | + | + | | | | | + | | | | | | + | | | | | + | | | | | | + |
| 1101 | | + | + | | | | | + | | | | | | | | | | | + | | | + | | | |
| 1102 | | + | + | | | | | + | | | | | | | | | | | + | | | + | | | |
| 2301 | + | | + | | | | | + | | | + | | | | | | | + | | | | | | | + |
| 2401 | + | | + | | | | | + | | + | + | | | | | | | + | | | | + | | | + |
| 2402 | + | | + | | | | | + | | + | + | | | | | | | + | | | | + | | | + |
| 2403 | + | | + | | | | | + | | + | + | | | | | | | + | | | | | | | + |
| 2501 | | + | | | | | | | + | | + | | | | + | | | | + | | | | | | |
| 2601 | | + | | | | | | | + | | + | | | | + | | | | + | | | | | | |
| 2901 | | + | | | + | | | | | | + | | | | | | | + | | | | | | | + |
| 2902 | | + | | | + | | | | | | + | | | | | | | + | | | | | | | + |
| 3001 | | + | + | | | | | | | + | + | | | | | | | + | | | | | | | + |
| 3002 | | + | + | | | | | | | + | + | | | | | | | + | | | | | | | + |
| 3003 | | + | + | | | | | | | + | + | | | | | | | + | | | | | | | + |
| 3101 | | + | | | + | | | + | | | + | | | | | | | + | | | | | | | + |
| 3201 | | + | | | + | | | + | | | + | | | | | | | + | | | | | | | |
| 3301 | | + | | | + | | | + | | | + | | | | | | | | | | | | | | + |
| 3401 | | + | | | + | | | + | | | + | | | | | + | | | + | | | | | | |
| 3402 | | + | + | | | | | + | | | + | | | | | + | | | | | | | | | + |
| 3601 | | + | + | | | | | | | + | + | | | | | | | + | | + | | | | | |
| 4301 | | + | | | | | | | | + | + | | | | + | | | | + | | | | + | | |
| 6601 | | + | | | | | | + | | | + | | | | + | | | | + | | | + | | | |
| 6602 | | + | | | | | | + | | | + | | | | + | | | + | | | | | | | |
| 6801 | | + | | | + | | | | | | + | | | + | | | | + | | | | | | | + |
| 6802 | | + | | | | | | + | | | + | | | + | | | | + | | | | | | | |
| 6901 | | | | + | | | | + | | | + | | | + | | | | + | | | | | | + | |
| 7401 | | + | | | + | | | | | | + | | | | | | | + | | | | | | | |

SEQUENCE LISTING ( 1 ) GENERAL INFORMATION:

( i i i ) NUMBER OF SEQUENCES: 173

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATGAGGTATT TCTACACCTC CG                    22

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACGGATGTGA AGAAATACCT C                                                                          21

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGATGTGGTG AAATACCTC                                                                             19

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATGAGGTATT TCTCCACATC CG                                                                         22

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGGAAGCCCC GCTTC                                                                                 15

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCCATCCTCT GGCTCGCG                                                                              18

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGCGAGCCAG AAGATGGAG                                                                             19

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCCATCCTCC GGCTCGC　　　　　　　　　　　　　　　　　17

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GAGCAGGAGA GGCCTGAGTA　　　　　　　　　　　　　　20

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GGAGTATTGG GACCAGGAGA C　　　　　　　　　　　　　21

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TGTCTCCCCG TCCCAATACT CC　　　　　　　　　　　　22

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GAGTATTGGG ACGAGGAGAC　　　　　　　　　　　　　　20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CCGTGTCTGC AGGTCCCAAT A                        21

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

GTATTGGGAC CGGAACACAC                          20

( 2 ) INFORMATION FOR SEQ ID NO:15:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

GAGACACGGA ATATGAAGGC C                        21

( 2 ) INFORMATION FOR SEQ ID NO:16:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

TGGGCCTTCA CATTCCGTGT                          20

( 2 ) INFORMATION FOR SEQ ID NO:17:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:17:

GGGCCTTCAC TTTCCCTGT                           19

( 2 ) INFORMATION FOR SEQ ID NO:18:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

TGAAAGGCCC ACTCACAGAC T                        21

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GTCTGTGACT GGGCCTTCA                        19

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CAGACTCACC GAGTGGACCT                      20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CCAGGTCCAG TCGGTCAGTC                      20

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GACTGACCGA GCGAACCTG                        19

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GACTGACCGA GAGAACCTG                        19

( 2 ) INFORMATION FOR SEQ ID NO:24:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:24:

CGCAGGCTCT CTCGGTC 17

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GATCGCGCTC CGCTACTAC 19

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GGTTCTCACA CCATCCAGAG 20

( 2 ) INFORMATION FOR SEQ ID NO:27:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CCTCCAGATG ATGTTTGGC 19

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GGTTCTCACA CCCTCCAG 18

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TCTCACACCA TCCAGATAAT GTA 23

( 2 ) INFORMATION FOR SEQ ID NO:30:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

ACATCCTCTG GACGGTGTG                                                               19

( 2 ) INFORMATION FOR SEQ ID NO:31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

ATACATCATC TGGATGGTGA GAGA                                             24

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

TCATCTGGAC GGTGTGAGAC                                                      20

( 2 ) INFORMATION FOR SEQ ID NO:33:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TCGGACTGGC GCTTC                                                                     15

( 2 ) INFORMATION FOR SEQ ID NO:34:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

AGCGCCCGTC CGAC                                                                       14

( 2 ) INFORMATION FOR SEQ ID NO:35:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:35:

GCGGGTACCA CCAGTACG                                                    18

(2) INFORMATION FOR SEQ ID NO:36:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:36:

GGGTATGAAC AGCACGCC                                                    18

(2) INFORMATION FOR SEQ ID NO:37:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:37:

GGTACCAGCA GGACGC                                                      16

(2) INFORMATION FOR SEQ ID NO:38:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:38:

TGCGCTGGGT GATCTG                                                      16

(2) INFORMATION FOR SEQ ID NO:39:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:39:

CAGATCACCA AGCGCAA                                                     17

(2) INFORMATION FOR SEQ ID NO:40:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:40:

CTCAGACCAC CAAGCACAAG 20

( 2 ) INFORMATION FOR SEQ ID NO:41:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

GCGGTCCATG CGGC 14

( 2 ) INFORMATION FOR SEQ ID NO:42:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

AGGCGGCCCA TGTG 14

( 2 ) INFORMATION FOR SEQ ID NO:43:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CCTCATGGGC CGCC 14

( 2 ) INFORMATION FOR SEQ ID NO:44:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GAGACGGCCC ATGAGG 16

( 2 ) INFORMATION FOR SEQ ID NO:45:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GAGCAGTTGA GAGCCTAC 18

( 2 ) INFORMATION FOR SEQ ID NO:46:

( i ) SEQUENCE CHARACTERISTICS:
        ( A ) LENGTH: 18 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:46:

TAGGCTCTCT GCTGCTCC                                                                                                    18

( 2 ) INFORMATION FOR SEQ ID NO:47:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:47:

GGTAGGCTCT CCACTGCTC                                                                                                   19

( 2 ) INFORMATION FOR SEQ ID NO:48:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:48:

AGGTAGACTC TCCGCTGCT                                                                                                   19

( 2 ) INFORMATION FOR SEQ ID NO:49:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:49:

GAGGGCCGGT GCGT                                                                                                        14

( 2 ) INFORMATION FOR SEQ ID NO:50:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:50:

CGGAGCCCGT CCACA                                                                                                       15

( 2 ) INFORMATION FOR SEQ ID NO:51:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:51:

```
AGGATCCAGA CGCCGAGGAT GGCCG                                                      25

( 2 ) INFORMATION FOR SEQ ID NO:52:

( i ) SEQUENCE CHARACTERISTICS:
             ( A ) LENGTH: 28 base pairs
             ( B ) TYPE: nucleic acid
             ( C ) STRANDEDNESS: single
             ( D ) TOPOLOGY: linear ( i i ) MOLECULE TYPE: DNA (genomic)

( x i ) SEQUENCE DESCRIPTION: SEQ ID NO:52:

CAGGATCCCT CCTTCCCGTT CTCCAGGT                                                   28

( 2 ) INFORMATION FOR SEQ ID NO:53:

( i ) SEQUENCE CHARACTERISTICS:
             ( A ) LENGTH: 270 base pairs
             ( B ) TYPE: nucleic acid
             ( C ) STRANDEDNESS: single
             ( D ) TOPOLOGY: linear ( i i ) MOLECULE TYPE: DNA (genomic)

( x i ) SEQUENCE DESCRIPTION: SEQ ID NO:53:

GCTCCCACTC CATGAGGTAT TTCTTCACAT CCGTGTCCCG GCCCGGCCGC GGGGAGCCCC               60

GCTTCATCGC CGTGGGCTAC GTGGACGACA CGCAGTTCGT GCGGTTCGAC AGCGACGCCG              120

CGAGCCAGAA GATGGAGCCG CGGGCGCCGT GGATAGAGCA GGAGGGGCCG GAGTATTGGG              180

ACCAGGAGAC ACGGAATATG AAGGCCCACT CACAGACTGA CCGAGCGAAC CTGGGGACCC              240

TGCGCGGCTA CTACAACCAG AGCGAGGACG                                               270

( 2 ) INFORMATION FOR SEQ ID NO:54:

( i ) SEQUENCE CHARACTERISTICS:
             ( A ) LENGTH: 270 base pairs
             ( B ) TYPE: nucleic acid
             ( C ) STRANDEDNESS: single
             ( D ) TOPOLOGY: linear ( i i ) MOLECULE TYPE: DNA (genomic)

( x i ) SEQUENCE DESCRIPTION: SEQ ID NO:54:

GCTCTCACTC CATGAGGTAT TTCTTCACAT CCGTGTCCCG GCCCGGCCGC GGGGAGCCCC               60

GCTTCATCGC AGTGGGCTAC GTGGACGACA CGCAGTTCGT GCGGTTCGAC AGCGACGCCG              120

CGAGCCAGAG GATGGAGCCG CGGGCGCCGT GGATAGAGCA GGAGGGTCCG GAGTATTGGG              180

ACGGGGAGAC ACGGAAAGTG AAGGCCCACT CACAGACTCA CCGAGTGGAC CTGGGGACCC              240

TGCGCGGCTA CTACAACCAG AGCGAGGCCG                                               270

( 2 ) INFORMATION FOR SEQ ID NO:55:

( i ) SEQUENCE CHARACTERISTICS:
             ( A ) LENGTH: 270 base pairs
             ( B ) TYPE: nucleic acid
             ( C ) STRANDEDNESS: single
             ( D ) TOPOLOGY: linear ( i i ) MOLECULE TYPE: DNA (genomic)

( x i ) SEQUENCE DESCRIPTION: SEQ ID NO:55:

GCTCTCACTC CATGAGGTAT TTCTTCACAT CCGTGTCCCG GCCCGGCCGC GGGGAGCCCC               60

GCTTCATCGC AGTGGGCTAC GTGGACGACA CGCAGTTCGT GCGGTTCGAC AGCGACGCCG              120

CGAGCCGGAG GATGGAGCCG CGGGCGCCGT GGATAGAGCA GGAGGGTCCG GAGTATTGGG              180
```

| ACGGGGAGAC | ACGGAAAGTG | AAGCCCACT | CACAGACTCA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:56:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:56:

| GCTCTCACTC | CATGAGGTAT | TTCTTCACAT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGTCCG | GAGTATTGGG | 180 |
| ACGGGGAGAC | ACGGAAAGTG | AAGCCCACT | CACAGACTCA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:57:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:57:

| GCTCTCACTC | CATGAGGTAT | TTCTTCACAT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGTCCG | GAGTATTGGG | 180 |
| ACGGGGAGAC | ACGGAAAGTG | AAGCCCACT | CACAGACTCA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:58:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:58:

| GCTCTCACTC | CATGAGGTAT | TTCTACACCT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCGGAG | GATGGAGCCG | CGGGCGCCGT | GGATAGAGCA | GGAGGGTCCG | GAGTATTGGG | 180 |
| ACGGGGAGAC | ACGGAAAGTG | AAGCCCACT | CACAGACTCA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:59:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:59:

| GCTCTCACTC | CATGAGGTAT | TTCTACACCT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGTCCG | GAGTATTGGG | 180 |
| ACGGGGAGAC | ACGGAAAGTG | AAGGCCCACT | CACAGACTCA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:60:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:60:

| GCTCTCACTC | CATGAGGTAT | TTCTACACCT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGTCCG | GAGTATTGGG | 180 |
| ACGGGGAGAC | ACGGAAAGTG | AAGGCCCACT | CACAGACTCA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:61:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:61:

| GCTCTCACTC | CATGAGGTAT | TTCTTCACAT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGTCCG | GAGTATTGGG | 180 |
| ACGGGGAGAC | ACGGAAAGTG | AAGGCCCACT | CACAGATTGA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:62:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:62:

| GCTCTCACTC | CATGAGGTAT | TTCTTCACAT | CCGTGTCCCG | GCCCGGCCGC | GGGGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGTCCG | GAGTATTGGG | 180 |
| ACGGGGAGAC | ACGGAAAGTG | AAGGCCCACT | CACAGACTCA | CCGAGTGGAC | CTGGGGACCC | 240 |

TGCGCGGCTA CTACAACCAG AGCGAGGCCG                                          270

( 2 ) INFORMATION FOR SEQ ID NO:63:

( i ) SEQUENCE CHARACTERISTICS:
          ( A ) LENGTH: 270 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:63:

GCTCCCACTC CATGAGGTAT TTCTTCACAT CCGTGTCCCG GCCCGGCCGC GGGGAGCCCC          60

GCTTCATCGC CGTGGGCTAC GTGGACGACA CGCAGTTCGT GCGGTTCGAC AGCGACGCCG          120

CGAGCCAGAG GATGGAGCCG CGGGCGCCGT GGATAGAGCA GGAGGGGCCG GAGTATTGGG          180

ACCAGGAGAC ACGGAATGTG AAGGCCCAGT CACAGACTGA CCGAGTGGAC CTGGGGACCC          240

TGCGCGGCTA CTACAACCAG AGCGAGGCCG                                          270

( 2 ) INFORMATION FOR SEQ ID NO:64:

( i ) SEQUENCE CHARACTERISTICS:
          ( A ) LENGTH: 270 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:64:

GCTCCCACTC CATGAGGTAT TTCTTCACAT CCGTGTCCCG GCCCGGCCGC GGGGAGCCCC          60

GCTTCATCGC CGTGGGCTAC GTGGACGACA CGCAGTTCGT GCGGTTCGAC AGCGACGCCG          120

CGAGCCAGAG GATGGAGCCG CGGGCGCCGT GGATAGAGCA GGAGGGGCCG GAGTATTGGG          180

ACCAGGAGAC ACGGAATGTG AAGGCCCAGT CACAGACTGA CCGAGTGGAC CTGGGGACCC          240

TGCGCGGCTA CTACAACCAG AGCGAGGCCG                                          270

( 2 ) INFORMATION FOR SEQ ID NO:65:

( i ) SEQUENCE CHARACTERISTICS:
          ( A ) LENGTH: 270 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:65:

GCTCCCACTC CATGAGGTAT TTCTACACCT CCGTGTCCCG GCCCGGCCGC GGGGAGCCCC          60

GCTTCATCGC CGTGGGCTAC GTGGACGACA CGCAGTTCGT GCGGTTCGAC AGCGACGCCG          120

CGAGCCAGAG GATGGAGCCG CGGGCGCCGT GGATAGAGCA GGAGGGGCCG GAGTATTGGG          180

ACCAGGAGAC ACGGAATGTG AAGGCCCAGT CACAGACTGA CCGAGTGGAC CTGGGGACCC          240

TGCGCGGCTA CTACAACCAG AGCGAGGACG                                          270

( 2 ) INFORMATION FOR SEQ ID NO:66:

( i ) SEQUENCE CHARACTERISTICS:
          ( A ) LENGTH: 270 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:66:

| | | | | | |
|---|---|---|---|---|---|
| GCTCCCACTC | CATGAGGTAT | TTCTACACCT | CCGTGTCCCG | GCCCGGCCGC | GGGAAGCCCC | 60
| GCTTCATCGC | CGTGGGCTAC | GTGGACGACA | CGCAGTTCGT | GCGGTTCGAC | AGCGACGCCG | 120
| CGAGCCAGAG | GATGGAGCCG | CGGGCGCCGT | GGATAGAGCA | GGAGGGGCCG | GAGTATTGGG | 180
| ACCAGGAGAC | ACGGAATGTG | AAGGCCCAGT | CACAGACTGA | CCGAGTGGAC | CTGGGGACCC | 240
| TGCGCGGCTA | CTACAACCAG | AGCGAGGACG | | | | 270

( 2 ) INFORMATION FOR SEQ ID NO:67:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

| | | | | | |
|---|---|---|---|---|---|
| GCTCCCACTC | CATGAGGTAT | TTCTCCACAT | CCGTGTCCCG | GCCCGGCCGC | GGGGAGCCCC | 60
| GCTTCATCGC | CGTGGGCTAC | GTGGACGACA | CGCAGTTCGT | GCGGTTCGAC | AGCGACGCCG | 120
| CGAGCCAGAG | GATGGAGCCG | CGGGCGCCGT | GGATAGAGCA | GGAGGGGCCG | GAGTATTGGG | 180
| ACGAGGAGAC | AGGGAAAGTG | AAGGCCCACT | CACAGACTGA | CCGAGAGAAC | CTGCGGATCG | 240
| CGCTCCGCTA | CTACAACCAG | AGCGAGGCCG | | | | 270

( 2 ) INFORMATION FOR SEQ ID NO:68:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

| | | | | | |
|---|---|---|---|---|---|
| GCTCCCACTC | CATGAGGTAT | TTCTCCACAT | CCGTGTCCCG | GCCCGGCCGC | GGGGAGCCCC | 60
| GCTTCATCGC | CGTGGGCTAC | GTGGACGACA | CGCAGTTCGT | GCGGTTCGAC | AGCGACGCCG | 120
| CGAGCCAGAG | GATGGAGCCG | CGGGCGCCGT | GGATAGAGCA | GGAGGGGCCG | GAGTATTGGG | 180
| ACGAGGAGAC | AGGGAAAGTG | AAGGCCCACT | CACAGACTGA | CCGAGAGAAC | CTGCGGATCG | 240
| CGCTCCGCTA | CTACAACCAG | AGCGAGGCCG | | | | 270

( 2 ) INFORMATION FOR SEQ ID NO:69:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

| | | | | | |
|---|---|---|---|---|---|
| GCTCCCACTC | CATGAGGTAT | TTCTCCACAT | CCGTGTCCCG | GCCCGGCCGC | GGGGAGCCCC | 60
| GCTTCATCGC | CGTGGGCTAC | GTGGACGACA | CGCAGTTCGT | GCGGTTCGAC | AGCGACGCCG | 120
| CGAGCCAGAG | GATGGAGCCG | CGGGCGCCGT | GGATAGAGCA | GGAGGGGCCG | GAGTATTGGG | 180
| ACGAGGAGAC | AGGGAAAGTG | AAGGCCCACT | CACAGACTGA | CCGAGAGAAC | CTGCGGATCG | 240
| CGCTCCGCTA | CTACAACCAG | AGCGAGGCCG | | | | 270

( 2 ) INFORMATION FOR SEQ ID NO:70:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

```
GCTCCCACTC  CATGAGGTAT  TTCTCCACAT  CCGTGTCCCG  GCCCGGCCGC  GGGGAGCCCC    60
GCTTCATCGC  CGTGGGCTAC  GTGGACGACA  CGCAGTTCGT  GCGGTTCGAC  AGCGACGCCG   120
CGAGCCAGAG  GATGGAGCCG  CGGGCGCCGT  GGATAGAGCA  GGAGGGGCCG  GAGTATTGGG   180
ACGAGGAGAC  AGGGAAAGTG  AAGGCCCACT  CACAGACTGA  CCGAGAGAAC  CTGCGGATCG   240
CGCTCCGCTA  CTACAACCAG  AGCGAGGCCG                                      270
```

( 2 ) INFORMATION FOR SEQ ID NO:71:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

```
GCTCCCACTC  CATGAGGTAT  TTCTACACCT  CCGTGTCCCG  GCCCGGCCGC  GGGGAGCCCC    60
GCTTCATCGC  CGTGGGCTAC  GTGGACGACA  CGCAGTTCGT  GCGGTTCGAC  AGCGACGCCG   120
CGAGCCAGAG  GATGGAGCCG  CGGGCGCCGT  GGATAGAGCA  GGAGGGGCCG  GAGTATTGGG   180
ACCGGAACAC  ACGGAATGTG  AAGGCCCACT  CACAGACTGA  CCGAGAGAGC  CTGCGGATCG   240
CGCTCCGCTA  CTACAACCAG  AGCGAGGACG                                      270
```

( 2 ) INFORMATION FOR SEQ ID NO:72:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

```
GCTCCCACTC  CATGAGGTAT  TTCTACACCT  CCGTGTCCCG  GCCCGGCCGC  GGGGAGCCCC    60
GCTTCATCGC  CGTGGGCTAC  GTGGACGACA  CGCAGTTCGT  GCGGTTCGAC  AGCGACGCCG   120
CGAGCCAGAG  GATGGAGCCG  CGGGCGCCGT  GGATAGAGCA  GGAGGGGCCG  GAGTATTGGG   180
ACCGGAACAC  ACGGAATGTG  AAGGCCCACT  CACAGACTGA  CCGAGCGAAC  CTGGGGACCC   240
TGCGCGGCTA  CTACAACCAG  AGCGAGGACG                                      270
```

( 2 ) INFORMATION FOR SEQ ID NO:73:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

```
GCTCCCACTC  CATGAGGTAT  TTCACCACAT  CCGTGTCCCG  GCCCGGCCGC  GGGGAGCCCC    60
```

```
GCTTCATCGC CGTGGGCTAC GTGGACGACA CGCAGTTCGT GCGGTTTGAC AGCGACGCCG      120

CGAGCCAGAG GATGGAGCCG CGGGCACCGT GGATAGAGCA GGAGGGGCCG GAGTATTGGG      180

ACCTGCAGAC ACGGAATGTG AAGGCCCAGT CACAGACTGA CCGAGCGAAC CTGGGGACCC      240

TGCGCGGCTA CTACAACCAG AGCGAGGCCG                                       270
```

( 2 ) INFORMATION FOR SEQ ID NO:74:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

```
GCTCCCACTC CATGAGGTAT TTCACCACAT CCGTGTCCCG GCCCGGCCGC GGGGAGCCCC      60

GCTTCATCGC CGTGGGCTAC GTGGACGACA CGCAGTTCGT GCGGTTTGAC AGCGACGCCG      120

CGAGCCAGAG GATGGAGCCG CGGGCACCGT GGATAGAGCA GGAGGGGCCG GAGTATTGGG      180

ACCTGCAGAC ACGGAATGTG AAGGCCCAGT CACAGACTGA CCGAGCGAAC CTGGGGACCC      240

TGCGCGGCTA CTACAACCAG AGCGAGGCCG                                       270
```

( 2 ) INFORMATION FOR SEQ ID NO:75:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

```
GCTCCCACTC CATGAGGTAT TTCTTCACAT CCGTGTCCCG GCCCGGCAGT GGAGAGCCCC      60

GCTTCATCGC AGTGGGCTAC GTGGACGACA CGCAGTTCGT GCGGTTCGAC AGCGACGCCG      120

CGAGCCAGAG GATGGAGCCG CGGGCGCCGT GGATAGAGCA GGAGAGGCCT GAGTATTGGG      180

ACCAGGAGAC ACGGAATGTG AAGGCCCAGT CACAGACTGA CCGAGTGGAC CTGGGGACCC      240

TGCGCGGCTA CTACAACCAG AGCGAGGCCG                                       270
```

( 2 ) INFORMATION FOR SEQ ID NO:76:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

```
GCTCCCACTC CATGAGGTAT TTCTCCACAT CCGTGTCCCG GCCCGGCAGT GGAGAGCCCC      60

GCTTCATCGC AGTGGGCTAC GTGGACGACA CGCAGTTCGT GCGGTTCGAC AGCGACGCCG      120

CGAGCCAGAG GATGGAGCCG CGGGCGCCGT GGATAGAGCA GGAGAGGCCT GAGTATTGGG      180

ACCAGGAGAC ACGGAATGTG AAGGCCCACT CACAGACTGA CCGAGAGAAC CTGGGGACCC      240

TGCGCGGCTA CTACAACCAG AGCGAGGCCG                                       270
```

( 2 ) INFORMATION FOR SEQ ID NO:77:

( i ) SEQUENCE CHARACTERISTICS:

( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:77:

| GCTCCCACTC | CATGAGGTAT | TTCTCCACAT | CCGTGTCCCG | GCCCGGCAGT | GGAGAGCCCC | 60 |
| GCTTCATCGC | AGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGGCCG | GAGTATTGGG | 180 |
| ACCAGGAGAC | ACGGAATGTG | AAGGCCCACT | CACAGACTGA | CCGAGAGAAC | CTGGGGACCC | 240 |
| TGCGCGGCTA | CTACAACCAG | AGCGAGGCCG | | | | 270 |

( 2 ) INFORMATION FOR SEQ ID NO:78:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:78:

| GCTCCCACTC | CATGAGGTAT | TTCACCACAT | CCGTGTCCCG | GCCCGGCCGC | GGGGAGCCCC | 60 |
| GCTTCATCGC | CGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGAGGCCT | GAGTATTGGG | 180 |
| ACCAGGAGAC | ACGGAATGTG | AAGGCCCACT | CACAGATTGA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:79:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:79:

| GCTCCCACTC | CATGAGGTAT | TTCACCACAT | CCGTGTCCCG | GCCCGGCCGC | GGGGAGCCCC | 60 |
| GCTTCATCGC | CGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGAGGCCT | GAGTATTGGG | 180 |
| ACCAGGAGAC | ACGGAATGTG | AAGGCCCACT | CACAGATTGA | CCGAGTGGAC | CTGGGGACCC | 240 |
| TGCGCGGCTA | CTACAACCAG | AGCGAGGCCG | | | | 270 |

( 2 ) INFORMATION FOR SEQ ID NO:80:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:80:

| GCTCCCACTC | CATGAGGTAT | TTCTTCACAT | CCGTGTCCCG | GCCCGGCCGC | GGGGAGCCCC | 60 |
| GCTTCATCGC | CGTGGGCTAC | GTGGACGACA | CGCAGTTCGT | GCGGTTTGAC | AGCGACGCCG | 120 |

```
CGAGCCAGAG GATGGAGCCG CGGGCGCCGT GGATAGAGCA GGAGGGGCCG GAGTATTGGG      180

ACCAGGAGAC ACGGAATGTG AAGGCCCACT CACAGACTGA CCGAGAGAGC CTGCGGATCG      240

CGCTCCGCTA CTACAACCAG AGCGAGGCCG                                       270
```

( 2 ) INFORMATION FOR SEQ ID NO:81:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

```
GCTCCCACTC CATGAGGTAT TTCACCACAT CCGTGTCCCG GCCCGGCCGC GGGGAGCCCC      60

GCTTCATCGC CGTGGGCTAC GTGGACGACA CGCAGTTCGT GCGGTTCGAC AGCGACGCCG      120

CGAGCCAGAG GATGGAGCCG CGGGCGCCGT GGATAGAGCA GGAGGGGCCG GAGTATTGGG      180

ACCGGAACAC ACGGAATGTG AAGGCCCACT CACAGATTGA CCGAGTGGAC CTGGGGACCC      240

TGCGCGGCTA CTACAACCAG AGCGAGGCCG                                       270
```

( 2 ) INFORMATION FOR SEQ ID NO:82:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

```
GCTCCCACTC CATGAGGTAT TTCTACACCT CCGTGTCCCG GCCCGGCCGC GGGGAGCCCC      60

GCTTCATCGC CGTGGGCTAC GTGGACGACA CGCAGTTCGT GCGGTTCGAC AGCGACGCCG      120

CGAGCCAGAG GATGGAGCCG CGGGCGCCGT GGATAGAGCA GGAGGGGCCG GAGTATTGGG      180

ACCGGAACAC ACGGAAAGTG AAGGCCCAGT CACAGACTGA CCGAGTGGAC CTGGGGACCC      240

TGCGCGGCTA CTACAACCAG AGCGAGGACG                                       270
```

( 2 ) INFORMATION FOR SEQ ID NO:83:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:83:

```
GCTCCCACTC CATGAGGTAT TTCTACACCT CCGTGTCCCG GCCCGGCCGC GGGGAGCCCC      60

GCTTCATCGC CGTGGGCTAC GTGGACGACA CGCAGTTCGT GCGGTTCGAC AGCGACGCCG      120

CGAGCCAGAG GATGGAGCCG CGGGCGCCGT GGATAGAGCA GGAGGGGCCG GAGTATTGGG      180

ACCGGAACAC ACGGAATGTG AAGGCCCAGT CACAGACTGA CCGAGTGGAC CTGGGGACCC      240

TGCGCGGCTA CTACAACCAG AGCGAGGACG                                       270
```

( 2 ) INFORMATION FOR SEQ ID NO:84:

( i ) SEQUENCE CHARACTERISTICS:
        ( A ) LENGTH: 270 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:84:

| GCTCCCACTC | CATGAGGTAT | TTCTTCACAT | CCGTGTCCCG | GCCCGGCCGC | GGGGAGCCCC | 60 |
| GCTTCATCGC | CGTGGGCTAC | GTGGACGACA | CGCAGTTCGT | GCGGTTCGAC | AGCGACGCCG | 120 |
| CGAGCCAGAA | GATGGAGCCG | CGGGCGCCGT | GGATAGAGCA | GGAGGGGCCG | GAGTATTGGG | 180 |
| ACCAGGAGAC | ACGGAATATG | AAGGCCCACT | CACAGACTGA | CCGAGCGAAC | CTGGGGACCC | 240 |
| TGCGCGGCTA | CTACAACCAG | AGCGAGGACG | | | | 270 |

( 2 ) INFORMATION FOR SEQ ID NO:85:

( i ) SEQUENCE CHARACTERISTICS:
      ( A ) LENGTH: 270 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:85:

| GCTCCCACTC | CATGAGGTAT | TTCTACACCT | CCGTGTCCCG | GCCCGGCCGC | GGGGAGCCCC | 60 |
| GCTTCATCGC | CGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGGCCG | GAGTATTGGG | 180 |
| ACCTGCAGAC | ACGGAATGTG | AAGGCCCACT | CACAGACTGA | CCGAGCGAAC | CTGGGGACCC | 240 |
| TGCGCGGCTA | CTACAACCAG | AGCGAGGACG | | | | 270 |

( 2 ) INFORMATION FOR SEQ ID NO:86:

( i ) SEQUENCE CHARACTERISTICS:
      ( A ) LENGTH: 270 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:86:

| GCTCCCACTC | CATGAGGTAT | TTCTACACCT | CCGTGTCCCG | GCCCGGCCGC | GGGGAGCCCC | 60 |
| GCTTCATCGC | CGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGGCCG | GAGTATTGGG | 180 |
| ACCGGAACAC | ACGGAATGTG | AAGGCCCAGT | CACAGACTGA | CCGAGTGGAC | CTGGGGACCC | 240 |
| TGCGCGGCTA | CTACAACCAG | AGCGAGGACG | | | | 270 |

( 2 ) INFORMATION FOR SEQ ID NO:87:

( i ) SEQUENCE CHARACTERISTICS:
      ( A ) LENGTH: 270 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:87:

| GCTCCCACTC | CATGAGGTAT | TTCTACACCT | CCGTGTCCCG | GCCCGGCCGC | GGGGAGCCCC | 60 |
| GCTTCATCGC | CGTGGGCTAC | GTGGACGACA | CGCAGTTCGT | GCGGTTCGAC | AGCGACGCCG | 120 |
| CGAGCCAGAG | GATGGAGCCG | CGGGCGCCGT | GGATAGAGCA | GGAGGGGCCG | GAGTATTGGG | 180 |
| ACCGGAACAC | ACGGAATGTG | AAGGCCCAGT | CACAGACTGA | CCGAGTGGAC | CTGGGGACCC | 240 |

```
TGCGCGGCTA  CTACAACCAG  AGCGAGGCCG                                              270
```

( 2 ) INFORMATION FOR SEQ ID NO:88:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:88:

```
GCTCCCACTC  CATGAGGTAT  TTCTACACCT  CCGTGTCCCG  GCCCGGCCGC  GGGGAGCCCC      60
GCTTCATCGC  CGTGGGCTAC  GTGGACGACA  CGCAGTTCGT  GCGGTTCGAC  AGCGACGCCG     120
CGAGCCAGAG  GATGGAGCCG  CGGGCGCCGT  GGATAGAGCA  GGAGGGGCCG  GAGTATTGGG     180
ACCGGAACAC  ACGGAATGTG  AAGGCCCAGT  CACAGACTGA  CCGAGTGGAC  CTGGGGACCC     240
TGCGCGGCTA  CTACAACCAG  AGCGAGGCCG                                         270
```

( 2 ) INFORMATION FOR SEQ ID NO:89:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:89:

```
GCTCCCACTC  CATGAGGTAT  TTCTACACTT  CCGTGTCCCG  GCCCGGCCGC  GGGGAGCCCC      60
GCTTCATCGC  CGTGGGCTAC  GTGGACGACA  CGCAGTTCGT  GCGGTTCGAC  AGCGACGCCG     120
CGAGCCAGAG  GATGGAGCCG  CGGGCGCCGT  GGATAGAGCA  GGAGGGGCCG  GAGTATTGGG     180
ACCGGAACAC  ACGGAATGTG  AAGGCCCAGT  CACAGACTGA  CCGAGTGGAC  CTGGGGACCC     240
TGCGCGGCTA  CTACAACCAG  AGCGAGGCCG                                         270
```

( 2 ) INFORMATION FOR SEQ ID NO:90:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:90:

```
GCTCCCACTC  CATGAGGTAT  TTCTACACCT  CCATGTCCCG  GCCCGGCCGC  GGGGAGCCCC      60
GCTTCATCGC  CGTGGGCTAC  GTGGACGACA  CGCAGTTCGT  GCGGTTCGAC  AGCGACGCCG     120
CGAGCCAGAG  GATGGAGCCG  CGGGCGCCGT  GGATAGAGCA  GGAGGGGCCG  GAGTATTGGG     180
ACCGGAACAC  ACGGAATGTG  AAGGCCCAGT  CACAGACTGA  CCGAGTGGAC  CTGGGGACCC     240
TGCGCGGCTA  CTACAACCAG  AGCGAGGCCG                                         270
```

( 2 ) INFORMATION FOR SEQ ID NO:91:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

| | | | | | |
|---|---|---|---|---|---|
| GCTCCCACTC | CATGAGGTAT | TTCTACACCT | CCGTGTCCCG | GCCCGGCCGC | GGGGAGCCCC | 60
| GCTTCATCGC | CGTGGGCTAC | GTGGACGACA | CGCAGTTCGT | GCGGTTCGAC | AGCGACGCCG | 120
| CGAGCCAGAG | GATGGAGCCG | CGGGCGCCGT | GGATAGAGCA | GGAGGGGCCG | GAGTATTGGG | 180
| ACCGGAACAC | ACGGAATGTG | AAGGCCCAGT | CACAGACTGA | CCGAGTGGAC | CTGGGGACCC | 240
| TGCGCGGCTA | CTACAACCAG | AGCGAGGCCG | | | | 270

( 2 ) INFORMATION FOR SEQ ID NO:92:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:92:

| | | | | | |
|---|---|---|---|---|---|
| GCTCCCACTC | CATGAGGTAT | TTCTTCACAT | CCGTGTCCCG | GCCCGGCCGC | GGGGAGCCCC | 60
| GCTTCATCGC | CGTGGGCTAC | GTGGACGACA | CGCAGTTCGT | GCGGTTTGAC | AGCGACGCCG | 120
| CGAGCCAGAG | GATGGAGCCG | CGGGCGCCGT | GGATAGAGCA | GGAGGGGCCG | GAGTATTGGG | 180
| ACCAGGAGAC | ACGGAATGTG | AAGGCCCACT | CACAGACTGA | CCGAGTGGAC | CTGGGGACCC | 240
| TGCGCGGCTA | CTACAACCAG | AGCGAGGCCG | | | | 270

( 2 ) INFORMATION FOR SEQ ID NO:93:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:93:

| | | | | | |
|---|---|---|---|---|---|
| GCTCCCACTC | CATGAGGTAT | TTCTACACCT | CCGTGTCCCG | GCCCGGCCGC | GGGGAGCCCC | 60
| GCTTCATCGC | AGTGGGCTAC | GTGGACGACA | CGCAGTTCGT | GCGGTTCGAC | AGCGACGCCG | 120
| CGAGTCCGAG | GATGGAGCCG | CGGGCGCCGT | GGATAGAGCA | GGAGGGGCCG | GAGTATTGGG | 180
| ACCGGGAGAC | ACAGAACTTC | AAGGCCCACA | CACAGACTGA | CCGAGAGAAC | CTGCGGAACC | 240
| TGCGCGGCTA | CTACAACCAG | AGCGAGGCCG | | | | 270

( 2 ) INFORMATION FOR SEQ ID NO:94:

( i ) SEQUENCE CHARACTERISTICS:
    ( A ) LENGTH: 276 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:94:

| | | | | | |
|---|---|---|---|---|---|
| GTTCTCACAC | CATCCAGATA | ATGTATGGCT | GCGACGTGGG | GCCGGACGGG | CGCTTCCTCC | 60
| GCGGGTACCG | GCAGGACGCC | TACGACGGCA | AGGATTACAT | CGCCCTGAAC | GAGGACCTGC | 120
| GCTCTTGGAC | CGCGGCGGAC | ATGGCAGCTC | AGATCACCAA | GCGCAAGTGG | GAGGCGGTCC | 180
| ATGCGGCGGA | GCAGCGGAGA | GTCTACCTGG | AGGGCCGGTG | CGTGGACGGG | CTCCGCAGAT | 240
| ACCTGGAGAA | CGGGAAGGAG | ACGCTGCAGC | GCACGG | | | 276

( 2 ) INFORMATION FOR SEQ ID NO:95:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:95:

```
GTTCTCACAC CGTCCAGAGG ATGTATGGCT GCGACGTGGG GTCGGACTGG CGCTTCCTCC    60

GCGGGTACCA CCAGTACGCC TACGACGGCA AGGATTACAT CGCCCTGAAA GAGGACCTGC   120

GCTCTTGGAC CGCGGCGGAC ATGGCAGCTC AGACCACCAA GCACAAGTGG GAGGCGGCCC   180

ATGTGGCGGA GCAGTTGAGA GCCTACCTGG AGGGCACGTG CGTGGAGTGG CTCCGCAGAT   240

ACCTGGAGAA CGGGAAGGAG ACGCTGCAGC GCACGG                             276
```

( 2 ) INFORMATION FOR SEQ ID NO:96:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

```
GTTCTCACAC CCTCCAGAGG ATGTATGGCT GCGACGTGGG GTCGGACTGG CGCTTCCTGC    60

GCGGGTACCA CCAGTACGCC TACGACGGCA AGGATTACAT CGCCCTGAAA GAGGACCTGC   120

GCTCTTGGAC CGCGGCGGAC ATGGCAGCTC AGACCACCAA GCACAAGTGG GAGGCGGCCC   180

ATGTGGCGGA GCAGTGGAGA GCCTACCTGG AGGGCACGTG CGTGGAGTGG CTCCGCAGAT   240

ACCTGGAGAA CGGGAAGGAG ACGCTGCAGC GCACGG                             276
```

( 2 ) INFORMATION FOR SEQ ID NO:97:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:97:

```
GTTCTCACAC CGTCCAGAGG ATGTATGGCT GCGACGTGGG GTCGGACTGG CGCTTCCTCC    60

GCGGGTACCA CCAGTACGCC TACGACGGCA AGGATTACAT CGCCCTGAAA GAGGACCTGC   120

GCTCTTGGAC CGCGGCGGAC ATGGCAGCTC AGACCACCAA GCACAAGTGG GAGACGGCCC   180

ATGAGGCGGA GCAGTGGAGA GCCTACCTGG AGGGCACGTG CGTGGAGTGG CTCCGCAGAT   240

ACCTGGAGAA CGGGAAGGAG ACGCTGCAGC GCACGG                             276
```

( 2 ) INFORMATION FOR SEQ ID NO:98:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:98:

```
GTTCTCACAC  CGTCCAGATG  ATGTATGGCT  GCGACGTGGG  GTCGGACTGG  CGCTTCCTCC      60

GCGGGTACCA  CCAGTACGCC  TACGACGGCA  AGGATTACAT  CGCCCTGAAA  GAGGACCTGC     120

GCTCTTGGAC  CGCGGCGGAC  ATGGCAGCTC  AGACCACCAA  GCACAAGTGG  GAGGCGGCCC    180

ATGTGGCGGA  GCAGTTGAGA  GCCTACCTGG  AGGGCACGTG  CGTGGAGTGG  CTCCGCAGAT    240

ACCTGGAGAA  CGGGAAGGAG  ACGCTGCAGC  GCACGG                                276
```

( 2 ) INFORMATION FOR SEQ ID NO:99:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:99:

```
GTTCTCACAC  CCTCCAGAGG  ATGTATGGCT  GCGACGTGGG  GTCGGACTGG  CGCTTCCTGC      60

GCGGGTACCA  CCAGTACGCC  TACGACGGCA  AGGATTACAT  CGCCCTGAAA  GAGGACCTGC     120

GCTCTTGGAC  CGCGGCGGAC  ATGGCAGCTC  AGACCACCAA  GCACAAGTGG  GAGGCGGCCC    180

ATGTGGCGGA  GCAGTGGAGA  GCCTACCTGG  AGGGCACGTG  CGTGGAGTGG  CTCCGCAGAT    240

ACCTGGAGAA  CGGGAAGGAG  ACGCTGCAGC  GCACGG                                276
```

( 2 ) INFORMATION FOR SEQ ID NO:100:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:100:

```
GTTCTCACAC  CGTCCAGAGG  ATGTATGGCT  GCGACGTGGG  GTCGGACTGG  CGCTTCCTCC      60

GCGGGTACCA  CCAGTACGCC  TACGACGGCA  AGGATTACAT  CGCCCTGAAA  GAGGACCTGC     120

GCTCTTGGAC  CGCGGCGGAC  ATGGCAGCTC  AGACCACCAA  GCACAAGTGG  GAGGCGGCCC    180

ATGTGGCGGA  GCAGTTGAGA  GCCTACCTGG  AGGGCACGTG  CGTGGAGTGG  CTCCGCAGAT    240

ACCTGGAGAA  CGGGAAGGAG  ACGCTGCAGC  GCACGG                                276
```

( 2 ) INFORMATION FOR SEQ ID NO:101:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:101:

```
GTTCTCACAC  CGTCCAGAGG  ATGTTTGGCT  GCGACGTGGG  GTCGGACGGG  CGCTTCCTCC      60

GCGGGTACCA  CCAGTACGCC  TACGACGGCA  AGGATTACAT  CGCCCTGAAA  GAGGACCTGC     120

GCTCTTGGAC  CGCGGCGGAC  ATGGCAGCTC  AGACCACCAA  GCACAAGTGG  GAGGCGGCCC    180

ATGTGGCGGA  GCAGTTGAGA  GCCTACCTGG  AGGGCACGTG  CGTGGAGTGG  CTCCGCAGAT    240

ACCTGGAGAA  CGGGAAGGAG  ACGCTGCAGC  GCACGG                                276
```

( 2 ) INFORMATION FOR SEQ ID NO:102:

```
    ( i ) SEQUENCE CHARACTERISTICS:
            ( A ) LENGTH: 276 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:102:

GTTCTCACAC  CGTCCAGAGG  ATGTATGGCT  GCGACGTGGG  GTCGGACTGG  CGCTTCCTCC       60

GCGGGTACCA  CCAGTACGCC  TACGACGGCA  AGGATTACAT  CGCCCTGAAA  GAGGACCTGC      120

GCTCTTGGAC  CGCGGCGGAC  ATGGCAGCTC  AGACCACCAA  GCACAAGTGG  GAGGCGGCCC      180

ATGTGGCGGA  GCAGTTGAGA  GCCTACCTGG  AGGGCACGTG  CGTGGAGTGG  CTCCGCAGAT      240

ACCTGGAGAA  CGGGAAGGAG  ACGCTGCAGC  GCACGG                                  276

( 2 ) INFORMATION FOR SEQ ID NO:103:

( i ) SEQUENCE CHARACTERISTICS:
            ( A ) LENGTH: 276 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:103:

GTTCTCACAC  CGTCCAGAGG  ATGTATGGCT  GCGACGTGGG  GTCGGACTGG  CGCTTCCTCC       60

GCGGGTACCA  CCAGTACGCC  TACGACGGCA  AGGATTACAT  CGCCCTGAAA  GAGGACCTGC      120

GCTCTTGGAC  CGCGGCGGAC  ATGGCAGCTC  AGACCACCAA  GCACAAGTGG  GAGGCGGCCC      180

ATGTGGCGGA  GCAGCAGAGA  GCCTACCTGG  AGGGCACGTG  CGTGGAGTGG  CTCCGCAGAT      240

ACCTGGAGAA  CGGGAAGGAG  ACGCTGCAGC  GCACGG                                  276

( 2 ) INFORMATION FOR SEQ ID NO:104:

( i ) SEQUENCE CHARACTERISTICS:
            ( A ) LENGTH: 276 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:104:

GTTCTCACAC  CATCCAGATA  ATGTATGGCT  GCGACGTGGG  GTCGGACGGG  CGCTTCCTCC       60

GCGGGTACCG  GCAGGACGCC  TACGACGGCA  AGGATTACAT  CGCCCTGAAC  GAGGACCTGC      120

GCTCTTGGAC  CGCGGCGGAC  ATGGCGGCTC  AGATCACCAA  GCGCAAGTGG  GAGGCGGCCC      180

ATGAGGCGGA  GCAGTTGAGA  GCCTACCTGG  ATGGCACGTG  CGTGGAGTGG  CTCCGCAGAT      240

ACCTGGAGAA  CGGGAAGGAG  ACGCTGCAGC  GCACGG                                  276

( 2 ) INFORMATION FOR SEQ ID NO:105:

( i ) SEQUENCE CHARACTERISTICS:
            ( A ) LENGTH: 276 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:105:

GTTCTCACAC  CATCCAGATA  ATGTATGGCT  GCGACGTGGG  GTCGGACGGG  CGCTTCCTCC       60

GCGGGTACCG  GCAGGACGCC  TACGACGGCA  AGGATTACAT  CGCCCTGAAC  GAGGACCTGC      120
```

| | | | | | |
|---|---|---|---|---|---|
| GCTCTTGGAC | CGCGGCGGAC | ATGGCGGCTC | AGATCACCAA | GCGCAAGTGG | GAGGCGGCCC | 180
| ATGTGGCGGA | GCAGCAGAGA | GCCTACCTGG | ATGGCACGTG | CGTGGAGTGG | CTCCGCAGAT | 240
| ACCTGGAGAA | CGGGAAGGAG | ACGCTGCAGC | GCACGG | | | 276

( 2 ) INFORMATION FOR SEQ ID NO:106:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:106:

| | | | | | |
|---|---|---|---|---|---|
| GTTCTCACAC | CATCCAGATA | ATGTATGGCT | GCGACGTGGG | GCCGGACGGG | CGCTTCCTCC | 60
| GCGGGTACCG | GCAGGACGCC | TACGACGGCA | AGGATTACAT | CGCCCTGAAC | GAGGACCTGC | 120
| GCTCTTGGAC | CGCGGCGGAC | ATGGCAGCTC | AGATCACCAA | GCGCAAGTGG | GAGGCGGCCC | 180
| ATGCGGCGGA | GCAGCAGAGA | GCCTACCTGG | AGGGCCGGTG | CGTGGAGTGG | CTCCGCAGAT | 240
| ACCTGGAGAA | CGGGAAGGAG | ACGCTGCAGC | GCACGG | | | 276

( 2 ) INFORMATION FOR SEQ ID NO:107:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

| | | | | | |
|---|---|---|---|---|---|
| GTTCTCACAC | CATCCAGATA | ATGTATGGCT | GCGACGTGGG | GCCGGACGGG | CGCTTCCTCC | 60
| GCGGGTACCG | GCAGGACGCC | TACGACGGCA | AGGATTACAT | CGCCCTGAAC | GAGGACCTGC | 120
| GCTCTTGGAC | CGCGGCGGAC | ATGGCAGCTC | AGATCACCAA | GCGCAAGTGG | GAGGCGGCCC | 180
| ATGCGGCGGA | GCAGCAGAGA | GCCTACCTGG | AGGGCCGGTG | CGTGGAGTGG | CTCCGCAGAT | 240
| ACCTGGAGAA | CGGGAAGGAG | ACGCTGCAGC | GCACGG | | | 276

( 2 ) INFORMATION FOR SEQ ID NO:108:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:108:

| | | | | | |
|---|---|---|---|---|---|
| GTTCTCACAC | CCTCCAGATG | ATGTTTGGCT | GCGACGTGGG | GTCGGACGGG | CGCTTCCTCC | 60
| GCGGGTACCA | CCAGTACGCC | TACGACGGCA | AGGATTACAT | CGCCCTGAAA | GAGGACCTGC | 120
| GCTCTTGGAC | CGCGGCGGAC | ATGGCGGCTC | AGATCACCCA | GCGCAAGTGG | GAGGCGGCCC | 180
| GTGTGGCGGA | GCAGTTGAGA | GCCTACCTGG | AGGGCACGTG | CGTGGACGGG | CTCCGCAGAT | 240
| ACCTGGAGAA | CGGGAAGGAG | ACGCTGCAGC | GCACGG | | | 276

( 2 ) INFORMATION FOR SEQ ID NO:109:

( i ) SEQUENCE CHARACTERISTICS:
        ( A ) LENGTH: 276 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:109:

| | | | | | |
|---|---|---|---|---|---|
| GTTCTCACAC | CCTCCAGATG | ATGTTTGGCT | GCGACGTGGG | GTCGGACGGG | CGCTTCCTCC | 60 |
| GCGGGTACCA | CCAGTACGCC | TACGACGGCA | AGGATTACAT | CGCCCTGAAA | GAGGACCTGC | 120 |
| GCTCTTGGAC | CGCGGCGGAC | ATGGCGGCTC | AGATCACCAA | GCGCAAGTGG | GAGGCGGCCC | 180 |
| ATGTGGCGGA | GCAGCAGAGA | GCCTACCTGG | AGGGCACGTG | CGTGGACGGG | CTCCGCAGAT | 240 |
| ACCTGGAGAA | CGGGAAGGAG | ACGCTGCAGC | GCGCGG | | | 276 |

( 2 ) INFORMATION FOR SEQ ID NO:110:

( i ) SEQUENCE CHARACTERISTICS:
( A ) LENGTH: 276 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:110:

| | | | | | |
|---|---|---|---|---|---|
| GTTCTCACAC | CCTCCAGATG | ATGTTTGGCT | GCGACGTGGG | GTCGGACGGG | CGCTTCCTCC | 60 |
| GCGGGTACCA | CCAGTACGCC | TACGACGGCA | AGGATTACAT | CGCCCTGAAA | GAGGACCTGC | 120 |
| GCTCTTGGAC | CGCGGCGGAC | ATGGCGGCTC | AGATCACCAA | GCGCAAGTGG | GAGGCGGCCC | 180 |
| ATGTGGCGGA | GCAGCAGAGA | GCCTACCTGG | AGGGCACGTG | CGTGGACGGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:111:

( i ) SEQUENCE CHARACTERISTICS:
( A ) LENGTH: 276 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:111:

| | | | | | |
|---|---|---|---|---|---|
| GTTCTCACAC | CCTCCAGATG | ATGTTTGGCT | GCGACGTGGG | GTCGGACGGG | CGCTTCCTCC | 60 |
| GCGGGTACCA | CCAGTACGCC | TACGACGGCA | AGGATTACAT | CGCCCTGAAA | GAGGACCTGC | 120 |
| GCTCTTGGAC | CGCGGCGGAC | ATGGCGGCTC | AGATCACCAA | GCGCAAGTGG | GAGGCGGCCC | 180 |
| ATGTGGCGGA | GCAGCAGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:112:

( i ) SEQUENCE CHARACTERISTICS:
( A ) LENGTH: 276 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:112:

| | | | | | |
|---|---|---|---|---|---|
| GTTCTCACAC | CATCCAGAGG | ATGTATGGCT | GCGACGTGGG | GCCGGACGGG | CGCTTCCTCC | 60 |
| GCGGGTACCA | GCAGGACGCT | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGACGGCCC | 180 |

| ATGAGGCGGA | GCAGTGGAGA | GCCTACCTGG | AGGGCCGGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:113:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:113:

| GTTCTCACAC | CATCCAGAGG | ATGTATGGCT | GCGACGTGGG | GCCGGACGGG | CGCTTCCTCC | 60 |
| GCGGGTACCA | GCAGGACGCT | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGACGGCCC | 180 |
| ATGAGGCGGA | GCAGTGGAGA | GCCTACCTGG | AGGGCCGGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:114:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:114:

| GTTCTCACAC | CATCCAGATG | ATGTATGGCT | GCCACGTGGG | GTCGGACGGG | CGCTTCCTCC | 60 |
| GCGGGTACCG | GCAGGACGCC | TACGACGGCA | AGGATTACAT | CGCCTTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTGTGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:115:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:115:

| GTTCTCACAC | CATCCAGATG | ATGTATGGCT | GCGACGTGGG | GTCGGACGGG | CGCTTCCTCC | 60 |
| GCGGGTACCG | GCAGGACGCC | TACGACGGCA | AGGATTACAT | CGCCTTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTGTGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:116:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:116:

| | | | | | |
|---|---|---|---|---|---|
| GTTCTCACAC | CATCCAGATA | ATGTATGGCT | GCGACGTGGG | GTCGGACGGG | CGCTTCCTCC | 60 |
| GCGGGTATGA | ACAGCACGCC | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTTGGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:117:

( i ) SEQUENCE CHARACTERISTICS:
      ( A ) LENGTH: 276 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:117:

| | | | | | |
|---|---|---|---|---|---|
| GTTCTCACAC | CATCCAGATA | ATGTATGGCT | GCGACGTGGG | GTCGGACGGG | CGCTTCCTCC | 60 |
| GCGGGTATGA | ACAGCACGCC | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTCGGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:118:

( i ) SEQUENCE CHARACTERISTICS:
      ( A ) LENGTH: 276 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:118:

| | | | | | |
|---|---|---|---|---|---|
| GTTCTCACAC | CATCCAGATA | ATGTATGGCT | GCGACGTGGG | GTCGGACGGG | CGCTTCCTCC | 60 |
| GCGGGTATGA | ACAGCACGCC | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTCGGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:119:

( i ) SEQUENCE CHARACTERISTICS:
      ( A ) LENGTH: 276 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:119:

| | | | | | |
|---|---|---|---|---|---|
| GTTCTCACAC | CATCCAGATG | ATGTATGGCT | GCGACGTGGG | GTCGGACGGG | CGCTTCCTCC | 60 |
| GCGGGTACCA | GCAGGACGCC | TACGACGGCA | AGGATTACAT | CGCCTTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTGTGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:120:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

| | | | | | |
|---|---|---|---|---|---|
| GTTCTCACAC | CATCCAGATG | ATGTATGGCT | GCGACGTGGG | GTCGGACGGG | CGCTTCCTCC | 60 |
| GCGGGTACCA | GCAGGACGCC | TACGACGGCA | AGGATTACAT | CGCCTTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTGTGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:121:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:121:

| | | | | | |
|---|---|---|---|---|---|
| GTTCTCACAC | CATCCAGATG | ATGTATGGCT | GCGACGTGGG | GCCGGACGGG | CGCCTCCTCC | 60 |
| GCGGGTACCA | GCAGGACGCC | TACGACGGCA | AGGATTACAT | CGCCTTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTGTGGCGGA | GCAGTTGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:122:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:122:

| | | | | | |
|---|---|---|---|---|---|
| GTTCTCACAC | CATCCAGATG | ATGTATGGCT | GCGACGTGGG | GTCGGACGGG | CGCTTCCTCC | 60 |
| GCGGGTACCA | GCAGGACGCC | TACGACGGCA | AGGATTACAT | CGCCTTGAAC | GAGGACCTGC | 120 |
| GCTCTTGGAC | CGCGGCGGAC | ATGGCGGCTC | AGATCACCCA | GCGCAAGTGG | GAGGCGGCCC | 180 |
| GTGTGGCGGA | CGAGTTGAGA | GCCTACCTGG | AGGGCACGTG | CGTGGAGTGG | CTCCGCAGAC | 240 |
| ACCTGGAGAA | CGGGAAGGAG | ACGCTGCAGC | GCACGG | | | 276 |

( 2 ) INFORMATION FOR SEQ ID NO:123:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:123:

```
GTTCTCACAC CATCCAGAGG ATGTATGGCT GCGACGTGGG GCCGGACGGG CGCTTCCTCC      60
GCGGGTACCA GCAGGACGCT TACGACGGCA AGGATTACAT CGCCCTGAAC GAGGACCTGC     120
GCTCTTGGAC CGCGGCGGAC ATGGCGGCTC AGATCACCCA GCGCAAGTGG GAGACGGCCC     180
ATGAGGCGGA GCAGTGGAGA GCCTACCTGG AGGGCACGTG CGTGGAGTGG CTCCGCAGAT     240
ACCTGGAGAA CGGGAAGGAG ACGCTGCAGC GCACGG                               276
```

( 2 ) INFORMATION FOR SEQ ID NO:124:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:124:

```
GTTCTCACAC CATCCAGATA ATGTATGGCT GCGACGTGGG GTCGGACGGG CGCTTCCTCC      60
GCGGGTACCG GCAGGACGCT TACGACGGCA AGGATTACAT CGCCCTGAAC GAGGACCTGC     120
GCTCTTGGAC CGCGGCGGAC ATGGCGGCTC AGATCACCCA GCGCAAGTGG GAGACGGCCC     180
ATGAGGCGGA GCAGTTGAGA GCCTACCTGG AGGGCACGTG CGTGGAGTGG CTCCGCAGAT     240
ACCTGGAGAA CGGGAAGGAG ACGCTGCAGC GCACGG                               276
```

( 2 ) INFORMATION FOR SEQ ID NO:125:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:125:

```
GTTCTCACAC CATCCAGATA ATGTATGGCT GCGACGTGGG GCCGGACGGG CGCTTCCTCC      60
GCGGGTACCG GCAGGACGCC TACGACGGCA AGGATTACAT CGCCCTGAAC GAGGACCTGC     120
GCTCTTGGAC CGCGGCGGAC ATGGCAGCTC AGATCACCAA GCGCAAGTGG GAGGCGGTCC     180
ATGCGGCGGA GCAGCGGAGA GTCTACCTGG AGGGCACGTG CGTGGAGTGG CTCCGCAGAT     240
ACCTGGAGAA CGGGAAGGAG ACGCTGCAGC GCACGG                               276
```

( 2 ) INFORMATION FOR SEQ ID NO:126:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:126:

```
GTTCTCACAC CATCCAGAGG ATGTATGGCT GCGACGTGGG GCCGGACGGG CGCTTCCTCC      60
GCGGGTACCA GCAGGACGCT TACGACGGCA AGGATTACAT CGCCCTGAAC GAGGACCTGC     120
GCTCTTGGAC CGCGGCGGAC ATGGCGGCTC AGATCACCCA GCGCAAGTGG GAGACGGCCC     180
ATGAGGCGGA GCAGTGGAGA GCCTACCTGG AGGGCCGGTG CGTGGAGTGG CTCCGCAGAT     240
ACCTGGAGAA CGGGAAGGAG ACGCTGCAGC GCACGG                               276
```

( 2 ) INFORMATION FOR SEQ ID NO:127:

( i ) SEQUENCE CHARACTERISTICS:
  ( A ) LENGTH: 276 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:127:

| | | | | | | |
|---|---|---|---|---|---|---|
| GTTCTCACAC | CATCCAGAGG | ATGTATGGCT | GCGACGTGGG | GCCGGACGGG | CGCTTCCTCC | 60 |
| GCGGGTACCA | GCAGGACGCT | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGACGGCCC | 180 |
| ATGAGGCGGA | GCAGTGGAGA | GCCTACCTGG | AGGGCCGGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:128:

( i ) SEQUENCE CHARACTERISTICS:
    ( A ) LENGTH: 276 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:128:

| | | | | | | |
|---|---|---|---|---|---|---|
| GTTCTCACAC | CATCCAGAGG | ATGTATGGCT | GCGACGTGGG | GCCGGACGGG | CGCTTCCTCC | 60 |
| GCGGGTACCA | GCAGGACGCT | TACGACGGCA | AGGATTACAT | CGCCCTGAAC | GAGGACCTGC | 120 |
| GCTCTTGGAC | CGCGGCGGAC | ATGGCGGCTC | AGATCACCCA | GCGCAAGTGG | GAGACGGCCC | 180 |
| ATGAGGCGGA | GCAGTGGAGA | GCCTACCTGG | AGGGCGAGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:129:

( i ) SEQUENCE CHARACTERISTICS:
    ( A ) LENGTH: 276 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:129:

| | | | | | | |
|---|---|---|---|---|---|---|
| GTTCTCACAC | CATCCAGATG | ATGTATGGCT | GCGACGTGGG | GTCGGACGGG | CGCTTCCTCC | 60 |
| GCGGGTACCG | GCAGGACGCC | TACGACGGCA | AGGATTACAT | CGCCCTGAAA | GAGGACCTGC | 120 |
| GCTCTTGGAC | CGCGGCGGAC | ATGGCAGCTC | AGACCACCAA | GCACAAGTGG | GAGGCGGCCC | 180 |
| ATGTGGCGGA | GCAGTGGAGA | GCCTACCTGG | AGGGCACGTG | CGTGGAGTGG | CTCCGCAGAT | 240 |
| ACCTGGAGAA | CGGGAAGGAG | ACGCTGCAGC | GCACGG | | | 276 |

( 2 ) INFORMATION FOR SEQ ID NO:130:

( i ) SEQUENCE CHARACTERISTICS:
    ( A ) LENGTH: 276 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:130:

| | | | | | | |
|---|---|---|---|---|---|---|
| GTTCTCACAC | CATCCAGATG | ATGTATGGCT | GCGACGTGGG | GTCGGACGGG | CGCTTCCTCC | 60 |

| | | | | | |
|---|---|---|---|---|---|
| GCGGGTACCG | GCAGGACGCC | TACGACGGCA | AGGATTACAT | CGCCCTGAAA | GAGGACCTGC | 120
| GCTCTTGGAC | CGCGGCGGAC | ATGGCAGCTC | AGACCACCAA | GCACAAGTGG | GAGGCGGCCC | 180
| ATGTGGCGGA | GCAGTGGAGA | GCCTACCTGG | AGGGCACGTG | CGTGGAGTGG | CTCCGCAGAT | 240
| ACCTGGAGAA | CGGGAAGGAG | ACGCTGCAGC | GCACGG | | | 276

(2) INFORMATION FOR SEQ ID NO:131:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:131:

| | | | | | |
|---|---|---|---|---|---|
| GTTCTCACAC | CATCCAGAGG | ATGTATGGCT | GCGACGTGGG | GCCGGACGGG | CGCTTCCTCC | 60
| GCGGGTACCA | CCAGTACGCC | TACGACGGCA | AGGATTACAT | CGCCCTGAAA | GAGGACCTGC | 120
| GCTCTTGGAC | CGCGGCGGAC | ATGGCAGCTC | AGACCACCAA | GCACAAGTGG | GAGGCGGCCC | 180
| ATGTGGCGGA | GCAGTGGAGA | GCCTACCTGG | AGGGCACGTG | CGTGGAGTGG | CTCCGCAGAT | 240
| ACCTGGAGAA | CGGGAAGGAG | ACGCTGCAGC | GCACGG | | | 276

(2) INFORMATION FOR SEQ ID NO:132:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:132:

| | | | | | |
|---|---|---|---|---|---|
| GTTCTCACAC | CGTCCAGAGG | ATGTATGGCT | GCGACGTGGG | GTCGGACTGG | CGCTTCCTCC | 60
| GCGGGTACCA | CCAGTACGCC | TACGACGGCA | AGGATTACAT | CGCCCTGAAA | GAGGACCTGC | 120
| GCTCTTGGAC | CGCGGCGGAC | ATGGCAGCTC | AGACCACCAA | GCACAAGTGG | GAGGCGGCCC | 180
| ATGTGGCGGA | GCAGTTGAGA | GCCTACCTGG | AGGGCACGTG | CGTGGAGTGG | CTCCGCAGAT | 240
| ACCTGGAGAA | CGGGAAGGAG | ACGCTGCAGC | GCACGG | | | 276

(2) INFORMATION FOR SEQ ID NO:133:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:133:

| | | | | | |
|---|---|---|---|---|---|
| GTTCTCACAC | CATCCAGATG | ATGTATGGCT | GCGACGTGGG | GCCGGACGGG | CGCCTCCTCC | 60
| GCGGGTACCA | GCAGGACGCC | TACGACGGCA | AGGATTACAT | CGCCTTGAAC | GAGGACCTGC | 120
| GCTCTTGGAC | CGCGGCGGAC | ATGGCGGCTC | AGATCACCCA | GCGCAAGTGG | GAGGCGGCCC | 180
| GTGTGGCGGA | GCAGTTGAGA | GCCTACCTGG | AGGGCACGTG | CGTGGAGTGG | CTCCGCAGAT | 240
| ACCTGGAGAA | CGGGAAGGAG | ACGCTGCAGC | GCACGG | | | 276

(2) INFORMATION FOR SEQ ID NO:134:

(i) SEQUENCE CHARACTERISTICS:
        (A) LENGTH: 276 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:134:

| | | | | | |
|---|---|---|---|---|---|
| GGTCTCACAC | CCTCCAGAGG | ATGTATGGCT | GCGACGTGGG | GCCGGACGGG | CGCCTCCTCC | 60 |
| GCGGGTATAA | CCAGTACGCC | TACGACGGCA | AGGATTACAT | CGCCCTGAAC | GAGGACCTGC | 120 |
| GCTCCTGGAC | CGCGGCGGAC | ACGGCGGCTC | AGATCACCCA | GCGCAAGTGG | GAGGCGGCCC | 180 |
| GTGTGGCGGA | GCAGCTGAGA | GCCTACCTGG | AGGGCACGTG | CGTGGAGTGG | CTCCGCAGAT | 240 |
| ACCTGGAGAA | CGGGAAGGAG | ACGCTGCAGC | GCGCGG | | | 276 |

(2) INFORMATION FOR SEQ ID NO:135:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:135:

```
Gly Ser His Ser Met Arg Tyr Phe Tyr Thr Ser Val Ser Arg Pro Gly
 1               5                  10                  15
Arg Gly Glu Pro Arg Phe Ile Ala Val Gly Tyr Val Asp Asp Thr Gln
            20                  25                  30
Phe Val Arg Phe Asp Ser Asp Ala Ala Ser Pro Arg Met Glu Pro Arg
        35                  40                  45
Ala Pro Trp Ile Glu Gln Glu Gly Pro Glu Tyr Trp Asp Arg Glu Thr
    50                  55                  60
Gln Ile Val Lys Ala Asn Thr Gln Thr Asp Arg Glu Ser Leu Arg Asn
65                  70                  75                  80
Leu Arg Gly Tyr Tyr Asn Gln Ser Glu Ala Gly Ser His Thr Leu Gln
                85                  90                  95
Arg Met Tyr Gly Cys Asp Val Gly Pro Asp Gly Arg Leu Leu Arg Gly
            100                 105                 110
Tyr Asp Gln Tyr Ala Tyr Asp Gly Lys Asp Tyr Ile Ala Leu Asn Glu
        115                 120                 125
Asp Leu Arg Ser Trp Thr Ala Ala Asp Thr Ala Ala Gln Ile Thr Gln
    130                 135                 140
Arg Lys Trp Glu Ala Ala Arg Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Ala
            180
```

(2) INFORMATION FOR SEQ ID NO:136:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:136:

```
Gly Ser His Ser Met Arg Tyr Phe Phe Thr Ser Val Ser Arg Pro Gly
 1               5                  10                  15
```

```
Arg Gly Glu Pro Arg Phe Ile Ala Val Gly Tyr Val Asp Asp Thr Gln
            20                      25                  30

Phe Val Arg Phe Asp Ser Asp Ala Ala Ser Gln Lys Met Glu Pro Arg
            35                  40                  45

Ala Pro Trp Ile Glu Gln Glu Gly Pro Glu Tyr Trp Asp Gln Glu Thr
        50                  55                  60

Arg Asn Met Lys Ala His Ser Gln Thr Asp Arg Ala Asn Leu Gly Thr
65                      70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Lys
        130                 135                 140

Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr
            180
```

( 2 ) INFORMATION FOR SEQ ID NO:137:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:137:

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                      70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
        130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr
            180
```

( 2 ) INFORMATION FOR SEQ ID NO:138:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:138:

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Arg Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr
            180
```

( 2 ) INFORMATION FOR SEQ ID NO:139:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:139:

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
```

5,451,512

113                                            114
-continued 100                         105                         110

Tyr His Gln Tyr Ala Tyr Asp Gly Lys Asp Tyr Ile Ala Leu Lys Glu
            115                     120                     125

Asp Leu Arg Ser Trp Thr Ala Ala Asp Met Ala Ala Gln Thr Thr Lys
            130                     135                     140

His Lys Trp Glu Thr Ala His Glu Ala Glu Gln Trp Arg Ala Tyr Leu
    145                     150                     155                     160

Glu Gly Thr Cys Val Glu Trp Leu Arg Arg Tyr Leu Glu Asn Gly Lys
                            165                     170                     175

Glu Thr Leu Gln Arg Thr
                    180

( 2 ) INFORMATION FOR SEQ ID NO:140:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:140:

Gly Ser His Ser Met Arg Tyr Phe Phe Thr Ser Val Ser Arg Pro Gly
    1                   5                       10                      15

Arg Gly Glu Pro Arg Phe Ile Ala Val Gly Tyr Val Asp Asp Thr Gln
                    20                      25                      30

Phe Val Arg Phe Asp Ser Asp Ala Ala Ser Gln Arg Met Glu Pro Arg
                    35                      40                      45

Ala Pro Trp Ile Glu Gln Glu Gly Pro Glu Tyr Trp Asp Gly Glu Thr
            50                      55                      60

Arg Lys Val Lys Ala His Ser Gln Thr His Arg Val Asp Leu Gly Thr
    65                      70                      75                      80

Leu Arg Gly Tyr Tyr Asn Gln Ser Glu Ala Gly Ser His Thr Val Gln
                            85                      90                      95

Met Met Tyr Gly Cys Asp Val Gly Ser Asp Trp Arg Phe Leu Arg Gly
                    100                     105                     110

Tyr His Gln Tyr Ala Tyr Asp Gly Lys Asp Tyr Ile Ala Leu Lys Glu
            115                     120                     125

Asp Leu Arg Ser Trp Thr Ala Ala Asp Met Ala Ala Gln Thr Thr Lys
            130                     135                     140

His Lys Trp Glu Ala Ala His Val Ala Glu Gln Leu Arg Ala Tyr Leu
    145                     150                     155                     160

Glu Gly Thr Cys Val Glu Trp Leu Arg Arg Tyr Leu Glu Asn Gly Lys
                            165                     170                     175

Glu Thr Leu Gln Arg Thr
                    180

( 2 ) INFORMATION FOR SEQ ID NO:141:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:141:

Gly Ser His Ser Met Arg Tyr Phe Tyr Thr Ser Val Ser Arg Pro Gly
    1                   5                       10                      15

```
Arg  Gly  Gln  Pro  Arg  Phe  Ile  Ala  Val  Gly  Tyr  Val  Asp  Asp  Thr  Gln
               20                       25                      30

Phe  Val  Arg  Phe  Asp  Ser  Asp  Ala  Ala  Ser  Arg  Arg  Met  Glu  Pro  Arg
          35                       40                      45

Ala  Pro  Trp  Ile  Glu  Gln  Glu  Gly  Pro  Glu  Tyr  Trp  Asp  Gly  Glu  Thr
     50                       55                           60

Arg  Lys  Val  Lys  Ala  His  Ser  Gln  Thr  His  Arg  Val  Asp  Leu  Gly  Thr
65                       70                       75                           80

Leu  Arg  Gly  Tyr  Tyr  Asn  Gln  Ser  Glu  Ala  Gly  Ser  His  Thr  Leu  Gln
                    85                       90                           95

Arg  Met  Tyr  Gly  Cys  Asp  Val  Gly  Ser  Asp  Trp  Arg  Phe  Leu  Arg  Gly
               100                      105                     110

Tyr  His  Gln  Tyr  Ala  Tyr  Asp  Gly  Lys  Asp  Tyr  Ile  Ala  Leu  Lys  Glu
          115                      120                     125

Asp  Leu  Arg  Ser  Trp  Thr  Ala  Ala  Asp  Met  Ala  Ala  Gln  Thr  Thr  Lys
     130                      135                     140

His  Lys  Trp  Glu  Ala  Ala  His  Val  Ala  Glu  Gln  Trp  Arg  Ala  Tyr  Leu
145                      150                     155                          160

Glu  Gly  Thr  Cys  Val  Glu  Trp  Leu  Arg  Arg  Tyr  Leu  Glu  Asn  Gly  Lys
               165                      170                     175

Glu  Thr  Leu  Gln  Arg  Thr
               180
```

( 2 ) INFORMATION FOR SEQ ID NO:142:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:142:

```
Gly  Ser  His  Ser  Met  Arg  Tyr  Phe  Tyr  Thr  Ser  Val  Ser  Arg  Pro  Gly
1                   5                        10                      15

Arg  Gly  Glu  Pro  Arg  Phe  Ile  Ala  Val  Gly  Tyr  Val  Asp  Asp  Thr  Gln
               20                       25                      30

Phe  Val  Arg  Phe  Asp  Ser  Asp  Ala  Ala  Ser  Gln  Arg  Met  Glu  Pro  Arg
          35                       40                      45

Ala  Pro  Trp  Ile  Glu  Gln  Glu  Gly  Pro  Glu  Tyr  Trp  Asp  Gly  Glu  Thr
     50                       55                           60

Arg  Lys  Val  Lys  Ala  His  Ser  Gln  Thr  His  Arg  Val  Asp  Leu  Gly  Thr
65                       70                       75                           80

Leu  Arg  Gly  Tyr  Tyr  Asn  Gln  Ser  Glu  Ala  Gly  Ser  His  Thr  Val  Gln
                    85                       90                           95

Arg  Met  Tyr  Gly  Cys  Asp  Val  Gly  Ser  Asp  Trp  Arg  Phe  Leu  Arg  Gly
               100                      105                     110

Tyr  His  Gln  Tyr  Ala  Tyr  Asp  Gly  Lys  Asp  Tyr  Ile  Ala  Leu  Lys  Glu
          115                      120                     125

Asp  Leu  Arg  Ser  Trp  Thr  Ala  Ala  Asp  Met  Ala  Ala  Gln  Thr  Thr  Lys
     130                      135                     140

His  Lys  Trp  Glu  Ala  Ala  His  Val  Ala  Glu  Gln  Leu  Arg  Ala  Tyr  Leu
145                      150                     155                          160

Glu  Gly  Thr  Cys  Val  Glu  Trp  Leu  Arg  Arg  Tyr  Leu  Glu  Asn  Gly  Lys
               165                      170                     175

Glu  Thr  Leu  Gln  Arg  Thr
               180
```

( 2 ) INFORMATION FOR SEQ ID NO:143:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:143:

```
Gly Ser His Ser Met Arg Tyr Phe Tyr Thr Ser Val Ser Arg Pro Gly
 1               5                  10                  15
Arg Gly Glu Pro Arg Phe Ile Ala Val Gly Tyr Val Asp Asp Thr Gln
             20                  25                  30
Phe Val Arg Phe Asp Ser Asp Ala Ala Ser Gln Arg Met Glu Pro Arg
         35                  40                  45
Ala Pro Trp Ile Glu Gln Glu Gly Pro Glu Tyr Trp Asp Gly Glu Thr
     50                  55                  60
Arg Lys Val Lys Ala His Ser Gln Thr His Arg Val Asp Leu Gly Thr
 65                  70                  75                  80
Leu Arg Gly Tyr Tyr Asn Gln Ser Glu Ala Gly Ser His Thr Val Gln
                 85                  90                  95
Arg Met Phe Gly Cys Asp Val Gly Ser Asp Gly Arg Phe Leu Arg Gly
             100                 105                 110
Tyr His Gln Tyr Ala Tyr Asp Gly Lys Asp Tyr Ile Ala Leu Lys Glu
         115                 120                 125
Asp Leu Arg Ser Trp Thr Ala Ala Asp Met Ala Ala Gln Thr Thr Lys
     130                 135                 140
His Lys Trp Glu Ala Ala His Val Ala Glu Gln Leu Arg Ala Tyr Leu
145                 150                 155                 160
Glu Gly Thr Cys Val Glu Trp Leu Arg Arg Tyr Leu Glu Asn Gly Lys
                 165                 170                 175
Glu Thr Leu Gln Arg Thr
            180
```

( 2 ) INFORMATION FOR SEQ ID NO:144:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:144:

```
Gly Ser His Ser Met Arg Tyr Phe Phe Thr Ser Val Ser Arg Pro Gly
 1               5                  10                  15
Arg Gly Glu Pro Arg Phe Ile Ala Val Gly Tyr Val Asp Asp Thr Gln
             20                  25                  30
Phe Val Arg Phe Asp Ser Asp Ala Ala Ser Gln Arg Met Glu Pro Arg
         35                  40                  45
Ala Pro Trp Ile Glu Gln Glu Gly Pro Glu Tyr Trp Asp Gly Glu Thr
     50                  55                  60
Arg Lys Val Lys Ala His Ser Gln Ile Asp Arg Val Asp Leu Gly Thr
 65                  70                  75                  80
Leu Arg Gly Tyr Tyr Asn Gln Ser Glu Ala Gly Ser His Thr Val Gln
                 85                  90                  95
Arg Met Tyr Gly Cys Asp Val Gly Ser Asp Trp Arg Phe Leu Arg Gly
             100                 105                 110
```

| Tyr | His | Gln | Tyr | Ala | Tyr | Asp | Gly | Lys | Asp | Tyr | Ile | Ala | Leu | Lys | Glu |
|---|---|---|---|---|---|---|---|---|---|---|---|---|---|---|---|
| | | 115 | | | | 120 | | | | | 125 | | | | |

| Asp | Leu | Arg | Ser | Trp | Thr | Ala | Ala | Asp | Met | Ala | Ala | Gln | Thr | Thr | Lys |
|---|---|---|---|---|---|---|---|---|---|---|---|---|---|---|---|
| | 130 | | | | 135 | | | | | 140 | | | | | |

| His | Lys | Trp | Glu | Ala | Ala | His | Val | Ala | Glu | Gln | Leu | Arg | Ala | Tyr | Leu |
|---|---|---|---|---|---|---|---|---|---|---|---|---|---|---|---|
| 145 | | | | | 150 | | | | | 155 | | | | | 160 |

| Glu | Gly | Thr | Cys | Val | Glu | Trp | Leu | Arg | Arg | Tyr | Leu | Glu | Asn | Gly | Lys |
|---|---|---|---|---|---|---|---|---|---|---|---|---|---|---|---|
| | | | | 165 | | | | | 170 | | | | | 175 | |

| Glu | Thr | Leu | Gln | Arg | Thr |
|---|---|---|---|---|---|
| | | | 180 | | |

( 2 ) INFORMATION FOR SEQ ID NO:145:

( i ) SEQUENCE CHARACTERISTICS:
( A ) LENGTH: 182 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:145:

| Gly | Ser | His | Ser | Met | Arg | Tyr | Phe | Phe | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |

| Arg | Gly | Glu | Pro | Arg | Phe | Ile | Ala | Val | Gly | Tyr | Val | Asp | Asp | Thr | Gln |
|---|---|---|---|---|---|---|---|---|---|---|---|---|---|---|---|
| | | | 20 | | | | | 25 | | | | | 30 | | |

| Phe | Val | Arg | Phe | Asp | Ser | Asp | Ala | Ala | Ser | Gln | Arg | Met | Glu | Pro | Arg |
|---|---|---|---|---|---|---|---|---|---|---|---|---|---|---|---|
| | | 35 | | | | | 40 | | | | | 45 | | | |

| Ala | Pro | Trp | Ile | Glu | Gln | Glu | Gly | Pro | Glu | Tyr | Trp | Asp | Gly | Glu | Thr |
|---|---|---|---|---|---|---|---|---|---|---|---|---|---|---|---|
| | 50 | | | | | 55 | | | | | 60 | | | | |

| Arg | Lys | Val | Lys | Ala | His | Ser | Gln | Thr | His | Arg | Val | Asp | Leu | Gly | Thr |
|---|---|---|---|---|---|---|---|---|---|---|---|---|---|---|---|
| 65 | | | | | 70 | | | | | 75 | | | | | 80 |

| Leu | Arg | Gly | Tyr | Tyr | Asn | Gln | Ser | Glu | Ala | Gly | Ser | His | Thr | Val | Gln |
|---|---|---|---|---|---|---|---|---|---|---|---|---|---|---|---|
| | | | | 85 | | | | | 90 | | | | | 95 | |

| Arg | Met | Tyr | Gly | Cys | Asp | Val | Gly | Ser | Asp | Trp | Arg | Phe | Leu | Arg | Gly |
|---|---|---|---|---|---|---|---|---|---|---|---|---|---|---|---|
| | | | 100 | | | | | 105 | | | | | 110 | | |

| Tyr | His | Gln | Tyr | Ala | Tyr | Asp | Gly | Lys | Asp | Tyr | Ile | Ala | Leu | Lys | Glu |
|---|---|---|---|---|---|---|---|---|---|---|---|---|---|---|---|
| | | 115 | | | | 120 | | | | | 125 | | | | |

| Asp | Leu | Arg | Ser | Trp | Thr | Ala | Ala | Asp | Met | Ala | Ala | Gln | Thr | Thr | Lys |
|---|---|---|---|---|---|---|---|---|---|---|---|---|---|---|---|
| | 130 | | | | 135 | | | | | 140 | | | | | |

| His | Lys | Trp | Glu | Ala | Ala | His | Val | Ala | Glu | Gln | Gln | Arg | Ala | Tyr | Leu |
|---|---|---|---|---|---|---|---|---|---|---|---|---|---|---|---|
| 145 | | | | | 150 | | | | | 155 | | | | | 160 |

| Glu | Gly | Thr | Cys | Val | Glu | Trp | Leu | Arg | Arg | Tyr | Leu | Glu | Asn | Gly | Lys |
|---|---|---|---|---|---|---|---|---|---|---|---|---|---|---|---|
| | | | | 165 | | | | | 170 | | | | | 175 | |

| Glu | Thr | Leu | Gln | Arg | Thr |
|---|---|---|---|---|---|
| | | | 180 | | |

( 2 ) INFORMATION FOR SEQ ID NO:146:

( i ) SEQUENCE CHARACTERISTICS:
( A ) LENGTH: 182 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:146:

| Gly | Ser | His | Ser | Met | Arg | Tyr | Phe | Phe | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |

| Arg | Gly | Glu | Pro | Arg | Phe | Ile | Ala | Val | Gly | Tyr | Val | Asp | Asp | Thr | Gln |

```
                            20                        25                        30
        Phe  Val  Arg  Phe  Asp  Ser  Asp  Ala  Ala  Ser  Gln  Arg  Met  Glu  Pro  Arg
                  35                       40                       45

Ala  Pro  Trp  Ile  Glu  Gln  Glu  Gly  Pro  Glu  Tyr  Trp  Asp  Gln  Glu  Thr
             50                       55                       60

Arg  Asn  Val  Lys  Ala  Gln  Ser  Gln  Thr  Asp  Arg  Val  Asp  Leu  Gly  Thr
        65                       70                       75                       80

Leu  Arg  Gly  Tyr  Tyr  Asn  Gln  Ser  Glu  Ala  Gly  Ser  His  Thr  Ile  Gln
                            85                       90                       95

Ile  Met  Tyr  Gly  Cys  Asp  Val  Gly  Ser  Asp  Gly  Arg  Phe  Leu  Arg  Gly
                       100                      105                      110

Tyr  Arg  Gln  Asp  Ala  Tyr  Asp  Gly  Lys  Asp  Tyr  Ile  Ala  Leu  Asn  Glu
                  115                      120                      125

Asp  Leu  Arg  Ser  Trp  Thr  Ala  Ala  Asp  Met  Ala  Ala  Gln  Ile  Thr  Lys
             130                      135                      140

Arg  Lys  Trp  Glu  Ala  Ala  His  Glu  Ala  Glu  Gln  Leu  Arg  Ala  Tyr  Leu
        145                      150                      155                      160

Asp  Gly  Thr  Cys  Val  Glu  Trp  Leu  Arg  Arg  Tyr  Leu  Glu  Asn  Gly  Lys
                       165                      170                      175

Glu  Thr  Leu  Gln  Arg  Thr
                       180
```

( 2 ) INFORMATION FOR SEQ ID NO:147:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:147:

```
        Gly  Ser  His  Ser  Met  Arg  Tyr  Phe  Phe  Thr  Ser  Val  Ser  Arg  Pro  Gly
        1                   5                        10                       15

Arg  Gly  Glu  Pro  Arg  Phe  Ile  Ala  Val  Gly  Tyr  Val  Asp  Asp  Thr  Gln
                       20                       25                       30

Phe  Val  Arg  Phe  Asp  Ser  Asp  Ala  Ala  Ser  Gln  Arg  Met  Glu  Pro  Arg
                  35                       40                       45

Ala  Pro  Trp  Ile  Glu  Gln  Glu  Gly  Pro  Glu  Tyr  Trp  Asp  Gln  Glu  Thr
             50                       55                       60

Arg  Asn  Val  Lys  Ala  Gln  Ser  Gln  Thr  Asp  Arg  Val  Asp  Leu  Gly  Thr
        65                       70                       75                       80

Leu  Arg  Gly  Tyr  Tyr  Asn  Gln  Ser  Glu  Ala  Gly  Ser  His  Thr  Ile  Gln
                            85                       90                       95

Ile  Met  Tyr  Gly  Cys  Asp  Val  Gly  Ser  Asp  Gly  Arg  Phe  Leu  Arg  Gly
                       100                      105                      110

Tyr  Arg  Gln  Asp  Ala  Tyr  Asp  Gly  Lys  Asp  Tyr  Ile  Ala  Leu  Asn  Glu
                  115                      120                      125

Asp  Leu  Arg  Ser  Trp  Thr  Ala  Ala  Asp  Met  Ala  Ala  Gln  Ile  Thr  Lys
             130                      135                      140

Arg  Lys  Trp  Glu  Ala  Ala  His  Val  Ala  Glu  Gln  Leu  Arg  Ala  Tyr  Leu
        145                      150                      155                      160

Asp  Gly  Thr  Cys  Val  Glu  Trp  Leu  Arg  Arg  Tyr  Leu  Glu  Asn  Gly  Lys
                       165                      170                      175

Glu  Thr  Leu  Gln  Arg  Thr
                       180
```

(2) INFORMATION FOR SEQ ID NO:148:

(i) SEQUENCE CHARACTERISTICS:
        (A) LENGTH: 182 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:148:

```
Gly Ser His Ser Met Arg Tyr Phe Tyr Thr Ser Val Ser Arg Pro Gly
 1               5                  10                  15

Arg Gly Glu Pro Arg Phe Ile Ala Val Gly Tyr Val Asp Asp Thr Gln
             20                  25                  30

Phe Val Arg Phe Asp Ser Asp Ala Ala Ser Gln Arg Met Glu Pro Arg
         35                  40                  45

Ala Pro Trp Ile Glu Gln Glu Gly Pro Glu Tyr Trp Asp Gln Glu Thr
     50                  55                  60

Arg Asn Val Lys Ala Gln Ser Gln Thr Asp Arg Val Asp Leu Gly Thr
 65                  70                  75                  80

Leu Arg Gly Tyr Tyr Asn Gln Ser Glu Asp Gly Ser His Thr Ile Gln
                 85                  90                  95

Ile Met Tyr Gly Cys Asp Val Gly Pro Asp Gly Arg Phe Leu Arg Gly
             100                 105                 110

Tyr Arg Gln Asp Ala Tyr Asp Gly Lys Asp Tyr Ile Ala Leu Asn Glu
         115                 120                 125

Asp Leu Arg Ser Trp Thr Ala Ala Asp Met Ala Ala Gln Ile Thr Lys
     130                 135                 140

Arg Lys Trp Glu Ala Ala His Ala Ala Glu Gln Gln Arg Ala Tyr Leu
145                 150                 155                 160

Glu Gly Arg Cys Val Glu Trp Leu Arg Arg Tyr Leu Glu Asn Gly Lys
                 165                 170                 175

Glu Thr Leu Gln Arg Thr
             180
```

(2) INFORMATION FOR SEQ ID NO:149:

(i) SEQUENCE CHARACTERISTICS:
        (A) LENGTH: 182 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:149:

```
Gly Ser His Ser Met Arg Tyr Phe Tyr Thr Ser Val Ser Arg Pro Gly
 1               5                  10                  15

Arg Gly Lys Pro Arg Phe Ile Ala Val Gly Tyr Val Asp Asp Thr Gln
             20                  25                  30

Phe Val Arg Phe Asp Ser Asp Ala Ala Ser Gln Arg Met Glu Pro Arg
         35                  40                  45

Ala Pro Trp Ile Glu Gln Glu Gly Pro Glu Tyr Trp Asp Gln Glu Thr
     50                  55                  60

Arg Asn Val Lys Ala Gln Ser Gln Thr Asp Arg Val Asp Leu Gly Thr
 65                  70                  75                  80

Leu Arg Gly Tyr Tyr Asn Gln Ser Glu Asp Gly Ser His Thr Ile Gln
                 85                  90                  95

Ile Met Tyr Gly Cys Asp Val Gly Pro Asp Gly Arg Phe Leu Arg Gly
             100                 105                 110
```

| Tyr | Arg | Gln | Asp | Ala | Tyr | Asp | Gly | Lys | Asp | Tyr | Ile | Ala | Leu | Asn | Glu |
|-----|-----|-----|-----|-----|-----|-----|-----|-----|-----|-----|-----|-----|-----|-----|-----|
|     |     | 115 |     |     |     | 120 |     |     |     |     |     | 125 |     |     |     |

| Asp | Leu | Arg | Ser | Trp | Thr | Ala | Ala | Asp | Met | Ala | Ala | Gln | Ile | Thr | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Arg | Lys | Trp | Glu | Ala | Ala | His | Ala | Ala | Glu | Gln | Arg | Ala | Tyr | Leu |
|-----|-----|-----|-----|-----|-----|-----|-----|-----|-----|-----|-----|-----|-----|-----|
| 145 |     |     |     |     | 150 |     |     |     |     | 155 |     |     |     | 160 |

| Glu | Gly | Arg | Cys | Val | Glu | Trp | Leu | Arg | Arg | Tyr | Leu | Glu | Asn | Gly | Lys |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Glu | Thr | Leu | Gln | Arg | Thr |
|-----|-----|-----|-----|-----|-----|
|     |     |     | 180 |     |     |

( 2 ) INFORMATION FOR SEQ ID NO:150:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:150:

| Gly | Ser | His | Ser | Met | Arg | Tyr | Phe | Ser | Thr | Ser | Val | Ser | Arg | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Gly | Glu | Pro | Arg | Phe | Ile | Ala | Val | Gly | Tyr | Val | Asp | Asp | Thr | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Phe | Val | Arg | Phe | Asp | Ser | Asp | Ala | Ala | Ser | Gln | Arg | Met | Glu | Pro | Arg |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Pro | Trp | Ile | Glu | Gln | Glu | Gly | Pro | Glu | Tyr | Trp | Asp | Glu | Glu | Thr |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Lys | Val | Lys | Ala | His | Ser | Gln | Thr | Asp | Arg | Glu | Asn | Leu | Arg | Ile |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Leu | Arg | Tyr | Tyr | Asn | Gln | Ser | Glu | Ala | Gly | Ser | His | Thr | Leu | Gln |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Met | Met | Phe | Gly | Cys | Asp | Val | Gly | Ser | Asp | Gly | Arg | Phe | Leu | Arg | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Tyr | His | Gln | Tyr | Ala | Tyr | Asp | Gly | Lys | Asp | Tyr | Ile | Ala | Leu | Lys | Glu |
|-----|-----|-----|-----|-----|-----|-----|-----|-----|-----|-----|-----|-----|-----|-----|-----|
|     |     | 115 |     |     |     | 120 |     |     |     |     |     | 125 |     |     |     |

| Asp | Leu | Arg | Ser | Trp | Thr | Ala | Ala | Asp | Met | Ala | Ala | Gln | Ile | Thr | Gln |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Arg | Lys | Trp | Glu | Ala | Ala | Arg | Val | Ala | Glu | Gln | Leu | Arg | Ala | Tyr | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Glu | Gly | Thr | Cys | Val | Asp | Gly | Leu | Arg | Arg | Tyr | Leu | Glu | Asn | Gly | Lys |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Glu | Thr | Leu | Gln | Arg | Thr |
|-----|-----|-----|-----|-----|-----|
|     |     |     | 180 |     |     |

( 2 ) INFORMATION FOR SEQ ID NO:151:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:151:

| Gly | Ser | His | Ser | Met | Arg | Tyr | Phe | Ser | Thr | Ser | Val | Ser | Arg | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Gly | Glu | Pro | Arg | Phe | Ile | Ala | Val | Gly | Tyr | Val | Asp | Asp | Thr | Gln |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

```
Phe Val Arg Phe Asp Ser Asp Ala Ala Ser Gln Arg Met Glu Pro Arg
        35                      40                  45

Ala Pro Trp Ile Glu Gln Glu Gly Pro Glu Tyr Trp Asp Glu Glu Thr
        50                      55                  60

Gly Lys Val Lys Ala His Ser Gln Thr Asp Arg Glu Asn Leu Arg Ile
65                      70                  75                  80

Ala Leu Arg Tyr Tyr Asn Gln Ser Glu Ala Gly Ser His Thr Leu Gln
                85                      90                  95

Met Met Phe Gly Cys Asp Val Gly Ser Asp Gly Arg Phe Leu Arg Gly
            100                     105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Ile Thr Lys
        130                     135                 140

Arg Lys Trp Glu Ala Ala His Val Ala Glu Gln Gln Arg Ala Tyr Leu
145                     150                 155                 160

Glu Gly Thr Cys Val Asp Gly Leu Arg Arg Tyr Leu Glu Asn Gly Lys
                165                     170                 175

Glu Thr Leu Gln Arg Ala
                180
```

( 2 ) INFORMATION FOR SEQ ID NO:152:

( i ) SEQUENCE CHARACTERISTICS:
( A ) LENGTH: 182 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:152:

```
Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                      40                  45

Ala Pro Trp Ile Glu Gln Glu Gly Pro Glu Tyr Trp Asp Glu Glu Thr
        50                      55                  60

Gly Lys Val Lys Ala His Ser Gln Thr Asp Arg Glu Asn Leu Arg Ile
65                      70                  75                  80

Ala Leu Arg Tyr Tyr Asn Gln Ser Glu Ala Gly Ser His Thr Leu Gln
                85                      90                  95

Met Met Phe Gly Cys Asp Val Gly Ser Asp Gly Arg Phe Leu Arg Gly
            100                     105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Ile Thr Lys
        130                     135                 140

Arg Lys Trp Glu Ala Ala His Val Ala Glu Gln Gln Arg Ala Tyr Leu
145                     150                 155                 160

Glu Gly Thr Cys Val Asp Gly Leu Arg Arg Tyr Leu Glu Asn Gly Lys
                165                     170                 175

Glu Thr Leu Gln Arg Thr
                180
```

( 2 ) INFORMATION FOR SEQ ID NO:153:

(i) SEQUENCE CHARACTERISTICS:
    (A) LENGTH: 182 amino acids
    (B) TYPE: amino acid
    (C) STRANDEDNESS: single
    (D) TOPOLOGY: linear (ii) MOLECULE TYPE: DNA (genomic)

(xi) SEQUENCE DESCRIPTION: SEQ ID NO:153:

```
Gly Ser His Ser Met Arg Tyr Phe Ser Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Glu Glu Thr
        50                  55                  60

Gly Lys Val Lys Ala His Ser Gln Thr Asp Arg Glu Asn Leu Arg Ile
65                  70                  75                  80

Ala Leu Arg Tyr Tyr Asn Gln Ser Glu Ala Gly Ser His Thr Leu Gln
                85                  90                  95

Met Met Phe Gly Cys Asp Val Gly Ser Asp Gly Arg Phe Leu Arg Gly
            100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Ile Thr Lys
        130                 135                 140

Arg Lys Trp Glu Ala Ala His Val Ala Glu Gln Gln Arg Ala Tyr Leu
145                 150                 155                 160

Glu Gly Thr Cys Val Glu Trp Leu Arg Arg Tyr Leu Glu Asn Gly Lys
            165                 170                 175

Glu Thr Leu Gln Arg Thr
            180
```

(2) INFORMATION FOR SEQ ID NO:154:

(i) SEQUENCE CHARACTERISTICS:
    (A) LENGTH: 182 amino acids
    (B) TYPE: amino acid
    (C) STRANDEDNESS: single
    (D) TOPOLOGY: linear (ii) MOLECULE TYPE: DNA (genomic)

(xi) SEQUENCE DESCRIPTION: SEQ ID NO:154:

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Arg Asn Thr
        50                  55                  60

Arg Asn Val Lys Ala His Ser Gln Thr Asp Arg Glu Ser Leu Arg Ile
65                  70                  75                  80

Ala Leu Arg Tyr Tyr Asn Gln Ser Glu Asp Gly Ser His Thr Ile Gln
                85                  90                  95

Arg Met Tyr Gly Cys Asp Val Gly Pro Asp Gly Arg Phe Leu Arg Gly
            100                 105                 110

Tyr Gln Gln Asp Ala Tyr Asp Gly Lys Asp Tyr Ile Ala Leu Asn Glu
```

131
132

-continued

|  | 115 |  |  |  | 120 |  |  |  | 125 |  |  |  |
|---|---|---|---|---|---|---|---|---|---|---|---|---|
| Asp | Leu | Arg | Ser | Trp | Thr | Ala | Ala | Asp | Met | Ala | Ala | Gln | Ile | Thr | Gln |
|  | 130 |  |  |  |  | 135 |  |  |  |  | 140 |  |  |  |  |
| Arg | Lys | Trp | Glu | Thr | Ala | His | Glu | Ala | Glu | Gln | Trp | Arg | Ala | Tyr | Leu |
| 145 |  |  |  |  | 150 |  |  |  |  | 155 |  |  |  |  | 160 |
| Glu | Gly | Arg | Cys | Val | Glu | Trp | Leu | Arg | Arg | Tyr | Leu | Glu | Asn | Gly | Lys |
|  |  |  |  | 165 |  |  |  |  | 170 |  |  |  |  | 175 |  |
| Glu | Thr | Leu | Gln | Arg | Thr |
|  |  |  | 180 |  |  |

( 2 ) INFORMATION FOR SEQ ID NO:155:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:155:

| Gly | Ser | His | Ser | Met | Arg | Tyr | Phe | Tyr | Thr | Ser | Val | Ser | Arg | Pro | Gly |
|---|---|---|---|---|---|---|---|---|---|---|---|---|---|---|---|
| 1 |  |  |  | 5 |  |  |  |  | 10 |  |  |  |  | 15 |  |
| Arg | Gly | Glu | Pro | Arg | Phe | Ile | Ala | Val | Gly | Tyr | Val | Asp | Asp | Thr | Gln |
|  |  |  | 20 |  |  |  |  | 25 |  |  |  |  | 30 |  |  |
| Phe | Val | Arg | Phe | Asp | Ser | Asp | Ala | Ala | Ser | Gln | Arg | Met | Glu | Pro | Arg |
|  |  | 35 |  |  |  |  | 40 |  |  |  |  | 45 |  |  |  |
| Ala | Pro | Trp | Ile | Glu | Gln | Glu | Gly | Pro | Glu | Tyr | Trp | Asp | Arg | Asn | Thr |
|  | 50 |  |  |  |  | 55 |  |  |  |  | 60 |  |  |  |  |
| Arg | Asn | Val | Lys | Ala | His | Ser | Gln | Thr | Asp | Arg | Ala | Asn | Leu | Gly | Thr |
| 65 |  |  |  |  | 70 |  |  |  |  | 75 |  |  |  |  | 80 |
| Leu | Arg | Gly | Tyr | Tyr | Asn | Gln | Ser | Glu | Asp | Gly | Ser | His | Thr | Ile | Gln |
|  |  |  |  | 85 |  |  |  |  | 90 |  |  |  |  | 95 |  |
| Arg | Met | Tyr | Gly | Cys | Asp | Val | Gly | Pro | Asp | Gly | Arg | Phe | Leu | Arg | Gly |
|  |  |  | 100 |  |  |  |  | 105 |  |  |  |  | 110 |  |  |
| Tyr | Gln | Gln | Asp | Ala | Tyr | Asp | Gly | Lys | Asp | Tyr | Ile | Ala | Leu | Asn | Glu |
|  |  |  | 115 |  |  |  |  | 120 |  |  |  |  | 125 |  |  |
| Asp | Leu | Arg | Ser | Trp | Thr | Ala | Ala | Asp | Met | Ala | Ala | Gln | Ile | Thr | Gln |
|  | 130 |  |  |  |  | 135 |  |  |  |  | 140 |  |  |  |  |
| Arg | Lys | Trp | Glu | Thr | Ala | His | Glu | Ala | Glu | Gln | Trp | Arg | Ala | Tyr | Leu |
| 145 |  |  |  |  | 150 |  |  |  |  | 155 |  |  |  |  | 160 |
| Glu | Gly | Arg | Cys | Val | Glu | Trp | Leu | Arg | Arg | Tyr | Leu | Glu | Asn | Gly | Lys |
|  |  |  |  | 165 |  |  |  |  | 170 |  |  |  |  | 175 |  |
| Glu | Thr | Leu | Gln | Arg | Thr |
|  |  |  | 180 |  |  |

( 2 ) INFORMATION FOR SEQ ID NO:156:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:156:

| Gly | Ser | His | Ser | Met | Arg | Tyr | Phe | Thr | Thr | Ser | Val | Ser | Arg | Pro | Gly |
|---|---|---|---|---|---|---|---|---|---|---|---|---|---|---|---|
| 1 |  |  |  | 5 |  |  |  |  | 10 |  |  |  |  | 15 |  |
| Arg | Gly | Glu | Pro | Arg | Phe | Ile | Ala | Val | Gly | Tyr | Val | Asp | Asp | Thr | Gln |
|  |  |  | 20 |  |  |  |  | 25 |  |  |  |  | 30 |  |  |

-continued

```
Phe Val Arg Phe Asp Ser Asp Ala Ala Ser Gln Arg Met Glu Pro Arg
        35                  40                  45
Ala Pro Trp Ile Glu Gln Glu Gly Pro Glu Tyr Trp Asp Leu Gln Thr
    50                  55                  60
Arg Asn Val Lys Ala Gln Ser Gln Thr Asp Arg Ala Asn Leu Gly Thr
65                  70                  75                  80
Leu Arg Gly Tyr Tyr Asn Gln Ser Glu Ala Gly Ser His Thr Ile Gln
                85                  90                  95
Met Met Tyr Gly Cys His Val Gly Ser Asp Gly Arg Phe Leu Arg Gly
                100                 105                 110
Tyr Arg Gln Asp Ala Tyr Asp Gly Lys Asp Tyr Ile Ala Leu Asn Glu
            115                 120                 125
Asp Leu Arg Ser Trp Thr Ala Ala Asp Met Ala Ala Gln Ile Thr Gln
        130                 135                 140
Arg Lys Trp Glu Ala Ala Arg Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Thr
                180
```

( 2 ) INFORMATION FOR SEQ ID NO:157:

( i ) SEQUENCE CHARACTERISTICS:
       ( A ) LENGTH: 182 amino acids
       ( B ) TYPE: amino acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:157:

```
Gly Ser His Ser Met Arg Tyr Phe Thr Thr Ser Val Ser Arg Pro Gly
1               5                   10                  15
Arg Gly Glu Pro Arg Phe Ile Ala Val Gly Tyr Val Asp Asp Thr Gln
                20                  25                  30
Phe Val Arg Phe Asp Ser Asp Ala Ala Ser Gln Arg Met Glu Pro Arg
        35                  40                  45
Ala Pro Trp Ile Glu Gln Glu Gly Pro Glu Tyr Trp Asp Leu Gln Thr
    50                  55                  60
Arg Asn Val Lys Ala Gln Ser Gln Thr Asp Arg Ala Asn Leu Gly Thr
65                  70                  75                  80
Leu Arg Gly Tyr Tyr Asn Gln Ser Glu Ala Gly Ser His Thr Ile Gln
                85                  90                  95
Met Met Tyr Gly Cys Asp Val Gly Ser Asp Gly Arg Phe Leu Arg Gly
                100                 105                 110
Tyr Arg Gln Asp Ala Tyr Asp Gly Lys Asp Tyr Ile Ala Leu Asn Glu
            115                 120                 125
Asp Leu Arg Ser Trp Thr Ala Ala Asp Met Ala Ala Gln Ile Thr Gln
        130                 135                 140
Arg Lys Trp Glu Ala Ala Arg Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Thr
                180
```

( 2 ) INFORMATION FOR SEQ ID NO:158:

( i ) SEQUENCE CHARACTERISTICS:
  ( A ) LENGTH: 182 amino acids
  ( B ) TYPE: amino acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:158:

| Gly | Ser | His | Ser | Met | Arg | Tyr | Phe | Phe | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |

| Ser | Gly | Glu | Pro | Arg | Phe | Ile | Ala | Val | Gly | Tyr | Val | Asp | Asp | Thr | Gln |
|---|---|---|---|---|---|---|---|---|---|---|---|---|---|---|---|
| | | | 20 | | | | | 25 | | | | | 30 | | |

| Phe | Val | Arg | Phe | Asp | Ser | Asp | Ala | Ala | Ser | Gln | Arg | Met | Glu | Pro | Arg |
|---|---|---|---|---|---|---|---|---|---|---|---|---|---|---|---|
| | | 35 | | | | | 40 | | | | | 45 | | | |

| Ala | Pro | Trp | Ile | Glu | Gln | Glu | Arg | Pro | Glu | Tyr | Trp | Asp | Gln | Glu | Thr |
|---|---|---|---|---|---|---|---|---|---|---|---|---|---|---|---|
| | 50 | | | | | 55 | | | | | 60 | | | | |

| Arg | Asn | Val | Lys | Ala | Gln | Ser | Gln | Thr | Asp | Arg | Val | Asp | Leu | Gly | Thr |
|---|---|---|---|---|---|---|---|---|---|---|---|---|---|---|---|
| 65 | | | | 70 | | | | | 75 | | | | | 80 | |

| Leu | Arg | Gly | Tyr | Tyr | Asn | Gln | Ser | Glu | Ala | Gly | Ser | His | Thr | Ile | Gln |
|---|---|---|---|---|---|---|---|---|---|---|---|---|---|---|---|
| | | | | 85 | | | | | 90 | | | | | 95 | |

| Ile | Met | Tyr | Gly | Cys | Asp | Val | Gly | Ser | Asp | Gly | Arg | Phe | Leu | Arg | Gly |
|---|---|---|---|---|---|---|---|---|---|---|---|---|---|---|---|
| | | | 100 | | | | | 105 | | | | | 110 | | |

| Tyr | Glu | Gln | His | Ala | Tyr | Asp | Gly | Lys | Asp | Tyr | Ile | Ala | Leu | Asn | Glu |
|---|---|---|---|---|---|---|---|---|---|---|---|---|---|---|---|
| | | | 115 | | | | | 120 | | | | | 125 | | |

| Asp | Leu | Arg | Ser | Trp | Thr | Ala | Ala | Asp | Met | Ala | Ala | Gln | Ile | Thr | Gln |
|---|---|---|---|---|---|---|---|---|---|---|---|---|---|---|---|
| | 130 | | | | | 135 | | | | | 140 | | | | |

| Arg | Lys | Trp | Glu | Ala | Ala | Arg | Trp | Ala | Glu | Gln | Leu | Arg | Ala | Tyr | Leu |
|---|---|---|---|---|---|---|---|---|---|---|---|---|---|---|---|
| 145 | | | | | 150 | | | | | 155 | | | | | 160 |

| Glu | Gly | Thr | Cys | Val | Glu | Trp | Leu | Arg | Arg | Tyr | Leu | Glu | Asn | Gly | Lys |
|---|---|---|---|---|---|---|---|---|---|---|---|---|---|---|---|
| | | | | 165 | | | | | 170 | | | | | 175 | |

| Glu | Thr | Leu | Gln | Arg | Thr |
|---|---|---|---|---|---|
| | | | 180 | | |

( 2 ) INFORMATION FOR SEQ ID NO:159:

( i ) SEQUENCE CHARACTERISTICS:
  ( A ) LENGTH: 182 amino acids
  ( B ) TYPE: amino acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:159:

| Gly | Ser | His | Ser | Met | Arg | Tyr | Phe | Ser | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |

| Ser | Gly | Glu | Pro | Arg | Phe | Ile | Ala | Val | Gly | Tyr | Val | Asp | Asp | Thr | Gln |
|---|---|---|---|---|---|---|---|---|---|---|---|---|---|---|---|
| | | | 20 | | | | | 25 | | | | | 30 | | |

| Phe | Val | Arg | Phe | Asp | Ser | Asp | Ala | Ala | Ser | Gln | Arg | Met | Glu | Pro | Arg |
|---|---|---|---|---|---|---|---|---|---|---|---|---|---|---|---|
| | | 35 | | | | | 40 | | | | | 45 | | | |

| Ala | Pro | Trp | Ile | Glu | Gln | Glu | Arg | Pro | Glu | Tyr | Trp | Asp | Gln | Glu | Thr |
|---|---|---|---|---|---|---|---|---|---|---|---|---|---|---|---|
| | 50 | | | | | 55 | | | | | 60 | | | | |

| Arg | Asn | Val | Lys | Ala | His | Ser | Gln | Thr | Asp | Arg | Glu | Asn | Leu | Gly | Thr |
|---|---|---|---|---|---|---|---|---|---|---|---|---|---|---|---|
| 65 | | | | 70 | | | | | 75 | | | | | 80 | |

| Leu | Arg | Gly | Tyr | Tyr | Asn | Gln | Ser | Glu | Ala | Gly | Ser | His | Thr | Ile | Gln |
|---|---|---|---|---|---|---|---|---|---|---|---|---|---|---|---|
| | | | | 85 | | | | | 90 | | | | | 95 | |

| Ile | Met | Tyr | Gly | Cys | Asp | Val | Gly | Ser | Asp | Gly | Arg | Phe | Leu | Arg | Gly |
|---|---|---|---|---|---|---|---|---|---|---|---|---|---|---|---|
| | | | 100 | | | | | 105 | | | | | 110 | | |

| Tyr | Glu | Gln | His | Ala | Tyr | Asp | Gly | Lys | Asp | Tyr | Ile | Ala | Leu | Asn | Glu |
|---|---|---|---|---|---|---|---|---|---|---|---|---|---|---|---|
| | | | 115 | | | | | 120 | | | | | 125 | | |

```
Asp  Leu  Arg  Ser  Trp  Thr  Ala  Ala  Asp  Met  Ala  Ala  Gln  Ile  Thr  Gln
     130                      135                 140

Arg  Lys  Trp  Glu  Ala  Ala  Arg  Arg  Ala  Glu  Gln  Leu  Arg  Ala  Tyr  Leu
145                      150                      155                          160

Glu  Gly  Thr  Cys  Val  Glu  Trp  Leu  Arg  Arg  Tyr  Leu  Glu  Asn  Gly  Lys
               165                      170                           175

Glu  Thr  Leu  Gln  Arg  Thr
               180
```

( 2 ) INFORMATION FOR SEQ ID NO:160:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:160:

```
Gly  Ser  His  Ser  Met  Arg  Tyr  Phe  Ser  Thr  Ser  Val  Ser  Arg  Pro  Gly
1                   5                        10                      15

Ser  Gly  Glu  Pro  Arg  Phe  Ile  Ala  Val  Gly  Tyr  Val  Asp  Asp  Thr  Gln
               20                       25                           30

Phe  Val  Arg  Phe  Asp  Ser  Asp  Ala  Ala  Ser  Gln  Arg  Met  Glu  Pro  Arg
          35                      40                      45

Ala  Pro  Trp  Ile  Glu  Gln  Glu  Gly  Pro  Glu  Tyr  Trp  Asp  Gln  Glu  Thr
     50                      55                      60

Arg  Asn  Val  Lys  Ala  His  Ser  Gln  Thr  Asp  Arg  Glu  Asn  Leu  Gly  Thr
65                       70                  75                           80

Leu  Arg  Gly  Tyr  Tyr  Asn  Gln  Ser  Glu  Ala  Gly  Ser  His  Thr  Ile  Gln
               85                       90                           95

Ile  Met  Tyr  Gly  Cys  Asp  Val  Gly  Ser  Asp  Gly  Arg  Phe  Leu  Arg  Gly
               100                      105                     110

Tyr  Glu  Gln  His  Ala  Tyr  Asp  Gly  Lys  Asp  Tyr  Ile  Ala  Leu  Asn  Glu
          115                      120                      125

Asp  Leu  Arg  Ser  Trp  Thr  Ala  Ala  Asp  Met  Ala  Ala  Gln  Ile  Thr  Gln
     130                      135                 140

Arg  Lys  Trp  Glu  Ala  Ala  Arg  Arg  Ala  Glu  Gln  Leu  Arg  Ala  Tyr  Leu
145                      150                      155                          160

Glu  Gly  Thr  Cys  Val  Glu  Trp  Leu  Arg  Arg  Tyr  Leu  Glu  Asn  Gly  Lys
               165                      170                           175

Glu  Thr  Leu  Gln  Arg  Thr
               180
```

( 2 ) INFORMATION FOR SEQ ID NO:161:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:161:

```
Gly  Ser  His  Ser  Met  Arg  Tyr  Phe  Thr  Thr  Ser  Val  Ser  Arg  Pro  Gly
1                   5                        10                      15

Arg  Gly  Glu  Pro  Arg  Phe  Ile  Ala  Val  Gly  Tyr  Val  Asp  Asp  Thr  Gln
               20                       25                           30

Phe  Val  Arg  Phe  Asp  Ser  Asp  Ala  Ala  Ser  Gln  Arg  Met  Glu  Pro  Arg
```

|          |          |          |           | 3 5       |          |          |          | 4 0       |          |          |          | 4 5       |          |          |
|----------|----------|----------|-----------|-----------|----------|----------|----------|-----------|----------|----------|----------|-----------|----------|----------|
| Ala      | Pro      | Trp      | Ile       | Glu       | Gln      | Glu      | Arg      | Pro       | Glu      | Tyr      | Trp      | Asp       | Gln      | Glu      | Thr
|          |          |          | 50        |           |          |          |          | 55        |          |          |          | 60        |          |          |
| Arg      | Asn      | Val      | Lys       | Ala       | His      | Ser      | Gln      | Ile       | Asp      | Arg      | Val      | Asp       | Leu      | Gly      | Thr
| 65       |          |          |           | 70        |          |          |          |           | 75       |          |          |           |          |          | 80
| Leu      | Arg      | Gly      | Tyr       | Tyr       | Asn      | Gln      | Ser      | Glu       | Ala      | Gly      | Ser      | His       | Thr      | Ile      | Gln
|          |          |          |           | 85        |          |          |          | 90        |          |          |          |           | 95       |          |
| Met      | Met      | Tyr      | Gly       | Cys       | Asp      | Val      | Gly      | Ser       | Asp      | Gly      | Arg      | Phe       | Leu      | Arg      | Gly
|          |          |          | 100       |           |          |          |          | 105       |          |          |          | 110       |          |          |
| Tyr      | Gln      | Gln      | Asp       | Ala       | Tyr      | Asp      | Gly      | Lys       | Asp      | Tyr      | Ile      | Ala       | Leu      | Asn      | Glu
|          |          | 115      |           |           |          |          | 120      |           |          |          |          | 125       |          |          |
| Asp      | Leu      | Arg      | Ser       | Trp       | Thr      | Ala      | Ala      | Asp       | Met      | Ala      | Ala      | Gln       | Ile      | Thr      | Gln
|          |          | 130      |           |           |          | 135      |          |           |          |          |          | 140       |          |          |
| Arg      | Lys      | Trp      | Glu       | Ala       | Ala      | Arg      | Val      | Ala       | Glu      | Gln      | Leu      | Arg       | Ala      | Tyr      | Leu
| 145      |          |          |           |           | 150      |          |          |           |          | 155      |          |           |          |          | 160
| Glu      | Gly      | Thr      | Cys       | Val       | Glu      | Trp      | Leu      | Arg       | Arg      | Tyr      | Leu      | Glu       | Asn      | Gly      | Lys
|          |          |          |           | 165       |          |          |          | 170       |          |          |          |           | 175      |          |
| Glu      | Thr      | Leu      | Gln       | Arg       | Thr      |          |          |           |          |          |          |           |          |          |
|          |          |          | 180       |           |          |          |          |           |          |          |          |           |          |          |

( 2 ) INFORMATION FOR SEQ ID NO:162:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:162:

| Gly | Ser | His | Ser | Met | Arg | Tyr | Phe | Phe | Thr | Ser | Val | Ser | Arg | Pro | Gly |
| 1   |     |     |     | 5   |     |     |     |     | 10  |     |     |     |     | 15  |     |
| Arg | Gly | Glu | Pro | Arg | Phe | Ile | Ala | Val | Gly | Tyr | Val | Asp | Asp | Thr | Gln |
|     |     |     | 20  |     |     |     |     | 25  |     |     |     | 30  |     |     |     |
| Phe | Val | Arg | Phe | Asp | Ser | Asp | Ala | Ala | Ser | Gln | Arg | Met | Glu | Pro | Arg |
|     |     | 35  |     |     |     |     | 40  |     |     |     |     | 45  |     |     |     |
| Ala | Pro | Trp | Ile | Glu | Gln | Glu | Gly | Pro | Glu | Tyr | Trp | Asp | Gln | Glu | Thr |
|     |     |     | 50  |     |     |     |     | 55  |     |     |     | 60  |     |     |     |
| Arg | Asn | Val | Lys | Ala | His | Ser | Gln | Thr | Asp | Arg | Glu | Ser | Leu | Arg | Ile |
| 65  |     |     |     |     | 70  |     |     |     |     | 75  |     |     |     |     | 80  |
| Ala | Leu | Arg | Tyr | Tyr | Asn | Gln | Ser | Glu | Ala | Gly | Ser | His | Thr | Ile | Gln |
|     |     |     |     | 85  |     |     |     |     | 90  |     |     |     |     | 95  |     |
| Met | Met | Tyr | Gly | Cys | Asp | Val | Gly | Pro | Asp | Gly | Arg | Leu | Leu | Arg | Gly |
|     |     |     | 100 |     |     |     |     | 105 |     |     |     | 110 |     |     |     |
| Tyr | Gln | Gln | Asp | Ala | Tyr | Asp | Gly | Lys | Asp | Tyr | Ile | Ala | Leu | Asn | Glu |
|     |     | 115 |     |     |     |     | 120 |     |     |     |     | 125 |     |     |     |
| Asp | Leu | Arg | Ser | Trp | Thr | Ala | Ala | Asp | Met | Ala | Ala | Gln | Ile | Thr | Gln |
|     |     | 130 |     |     |     | 135 |     |     |     |     |     | 140 |     |     |     |
| Arg | Lys | Trp | Glu | Ala | Ala | Arg | Val | Ala | Glu | Gln | Leu | Arg | Ala | Tyr | Leu |
| 145 |     |     |     |     | 150 |     |     |     |     | 155 |     |     |     |     | 160 |
| Glu | Gly | Thr | Cys | Val | Glu | Trp | Leu | Arg | Arg | Tyr | Leu | Glu | Asn | Gly | Lys |
|     |     |     |     | 165 |     |     |     | 170 |     |     |     |     | 175 |     |     |
| Glu | Thr | Leu | Gln | Arg | Thr |     |     |     |     |     |     |     |     |     |     |
|     |     |     | 180 |     |     |     |     |     |     |     |     |     |     |     |     |

( 2 ) INFORMATION FOR SEQ ID NO:163:

( i ) SEQUENCE CHARACTERISTICS:

(A) LENGTH: 182 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:163:

| Gly | Ser | His | Ser | Met | Arg | Tyr | Phe | Thr | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |
| Arg | Gly | Glu | Pro | Arg | Phe | Ile | Ala | Val | Gly | Tyr | Val | Asp | Asp | Thr | Gln |
| | | | 20 | | | | | 25 | | | | | 30 | | |
| Phe | Val | Arg | Phe | Asp | Ser | Asp | Ala | Ala | Ser | Gln | Arg | Met | Glu | Pro | Arg |
| | | 35 | | | | | 40 | | | | | 45 | | | |
| Ala | Pro | Trp | Ile | Glu | Gln | Glu | Gly | Pro | Glu | Tyr | Trp | Asp | Arg | Asn | Thr |
| | | 50 | | | | | 55 | | | | | 60 | | | |
| Arg | Asn | Val | Lys | Ala | His | Ser | Gln | Ile | Asp | Arg | Val | Asp | Leu | Gly | Thr |
| 65 | | | | | 70 | | | | | 75 | | | | | 80 |
| Leu | Arg | Gly | Tyr | Tyr | Asn | Gln | Ser | Glu | Ala | Gly | Ser | His | Thr | Ile | Gln |
| | | | | 85 | | | | | 90 | | | | | 95 | |
| Met | Met | Tyr | Gly | Cys | Asp | Val | Gly | Ser | Asp | Gly | Arg | Phe | Leu | Arg | Gly |
| | | | 100 | | | | | 105 | | | | | 110 | | |
| Tyr | Gln | Gln | Asp | Ala | Tyr | Asp | Gly | Lys | Asp | Tyr | Ile | Ala | Leu | Asn | Glu |
| | | 115 | | | | | 120 | | | | | 125 | | | |
| Asp | Leu | Arg | Ser | Trp | Thr | Ala | Ala | Asp | Met | Ala | Ala | Gln | Ile | Thr | Gln |
| | 130 | | | | | 135 | | | | | 140 | | | | |
| Arg | Lys | Trp | Glu | Ala | Ala | Arg | Val | Ala | Asp | Glu | Leu | Arg | Ala | Tyr | Leu |
| 145 | | | | | 150 | | | | | 155 | | | | | 160 |
| Glu | Gly | Thr | Cys | Val | Glu | Trp | Leu | Arg | Arg | His | Leu | Glu | Asn | Gly | Lys |
| | | | | 165 | | | | | 170 | | | | | 175 | |
| Glu | Thr | Leu | Gln | Arg | Thr | | | | | | | | | | |
| | | | 180 | | | | | | | | | | | | |

(2) INFORMATION FOR SEQ ID NO:164:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:164:

| Gly | Ser | His | Ser | Met | Arg | Tyr | Phe | Tyr | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |
| Arg | Gly | Glu | Pro | Arg | Phe | Ile | Ala | Val | Gly | Tyr | Val | Asp | Asp | Thr | Gln |
| | | | 20 | | | | | 25 | | | | | 30 | | |
| Phe | Val | Arg | Phe | Asp | Ser | Asp | Ala | Ala | Ser | Gln | Arg | Met | Glu | Pro | Arg |
| | | 35 | | | | | 40 | | | | | 45 | | | |
| Ala | Pro | Trp | Ile | Glu | Gln | Glu | Gly | Pro | Glu | Tyr | Trp | Asp | Arg | Asn | Thr |
| | | 50 | | | | | 55 | | | | | 60 | | | |
| Arg | Lys | Val | Lys | Ala | Gln | Ser | Gln | Thr | Asp | Arg | Val | Asp | Leu | Gly | Thr |
| 65 | | | | | 70 | | | | | 75 | | | | | 80 |
| Leu | Arg | Gly | Tyr | Tyr | Asn | Gln | Ser | Glu | Asp | Gly | Ser | His | Thr | Ile | Gln |
| | | | | 85 | | | | | 90 | | | | | 95 | |
| Arg | Met | Tyr | Gly | Cys | Asp | Val | Gly | Pro | Asp | Gly | Arg | Phe | Leu | Arg | Gly |
| | | | 100 | | | | | 105 | | | | | 110 | | |
| Tyr | Gln | Gln | Asp | Ala | Tyr | Asp | Gly | Lys | Asp | Tyr | Ile | Ala | Leu | Asn | Glu |
| | | 115 | | | | | 120 | | | | | 125 | | | |

```
Asp  Leu  Arg  Ser  Trp  Thr  Ala  Ala  Asp  Met  Ala  Ala  Gln  Ile  Thr  Gln
     130                 135                      140

Arg  Lys  Trp  Glu  Thr  Ala  His  Glu  Ala  Glu  Gln  Trp  Arg  Ala  Tyr  Leu
145                      150                      155                      160

Glu  Gly  Thr  Cys  Val  Glu  Trp  Leu  Arg  Arg  Tyr  Leu  Glu  Asn  Gly  Lys
                    165                      170                      175

Glu  Thr  Leu  Gln  Arg  Thr
               180
```

( 2 ) INFORMATION FOR SEQ ID NO:165:

( i ) SEQUENCE CHARACTERISTICS:
      ( A ) LENGTH: 182 amino acids
      ( B ) TYPE: amino acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:165:

```
Gly  Ser  His  Ser  Met  Arg  Tyr  Phe  Tyr  Thr  Ser  Val  Ser  Arg  Pro  Gly
1                   5                   10                      15

Arg  Gly  Glu  Pro  Arg  Phe  Ile  Ala  Val  Gly  Tyr  Val  Asp  Asp  Thr  Gln
               20                       25                      30

Phe  Val  Arg  Phe  Asp  Ser  Asp  Ala  Ala  Ser  Gln  Arg  Met  Glu  Pro  Arg
               35                       40                      45

Ala  Pro  Trp  Ile  Glu  Gln  Glu  Gly  Pro  Glu  Tyr  Trp  Asp  Arg  Asn  Thr
     50                       55                      60

Arg  Asn  Val  Lys  Ala  Gln  Ser  Gln  Thr  Asp  Arg  Val  Asp  Leu  Gly  Thr
65                       70                      75                      80

Leu  Arg  Gly  Tyr  Tyr  Asn  Gln  Ser  Glu  Asp  Gly  Ser  His  Thr  Ile  Gln
                    85                      90                      95

Ile  Met  Tyr  Gly  Cys  Asp  Val  Gly  Ser  Asp  Gly  Arg  Phe  Leu  Arg  Gly
                    100                     105                     110

Tyr  Arg  Gln  Asp  Ala  Tyr  Asp  Gly  Lys  Asp  Tyr  Ile  Ala  Leu  Asn  Glu
          115                      120                     125

Asp  Leu  Arg  Ser  Trp  Thr  Ala  Ala  Asp  Met  Ala  Ala  Gln  Ile  Thr  Gln
     130                 135                      140

Arg  Lys  Trp  Glu  Thr  Ala  His  Glu  Ala  Glu  Gln  Leu  Arg  Ala  Tyr  Leu
145                      150                      155                      160

Glu  Gly  Thr  Cys  Val  Glu  Trp  Leu  Arg  Arg  Tyr  Leu  Glu  Asn  Gly  Lys
                    165                      170                      175

Glu  Thr  Leu  Gln  Arg  Thr
               180
```

( 2 ) INFORMATION FOR SEQ ID NO:166:

( i ) SEQUENCE CHARACTERISTICS:
      ( A ) LENGTH: 182 amino acids
      ( B ) TYPE: amino acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:166:

```
Gly  Ser  His  Ser  Met  Arg  Tyr  Phe  Phe  Thr  Ser  Val  Ser  Arg  Pro  Gly
1                   5                   10                      15

Arg  Gly  Glu  Pro  Arg  Phe  Ile  Ala  Val  Gly  Tyr  Val  Asp  Asp  Thr  Gln
               20                       25                      30

Phe  Val  Arg  Phe  Asp  Ser  Asp  Ala  Ala  Ser  Gln  Lys  Met  Glu  Pro  Arg
               35                       40                      45
```

```
Ala  Pro  Trp  Ile  Glu  Gln  Glu  Gly  Pro  Glu  Tyr  Trp  Asp  Gln  Glu  Thr
     50                       55                      60

Arg  Asn  Met  Lys  Ala  His  Ser  Gln  Thr  Asp  Arg  Ala  Asn  Leu  Gly  Thr
65                            70                 75                           80

Leu  Arg  Gly  Tyr  Tyr  Asn  Gln  Ser  Glu  Asp  Gly  Ser  His  Thr  Ile  Gln
                    85                      90                             95

Ile  Met  Tyr  Gly  Cys  Asp  Val  Gly  Pro  Asp  Gly  Arg  Phe  Leu  Arg  Gly
               100                 105                          110

Tyr  Arg  Gln  Asp  Ala  Tyr  Asp  Gly  Lys  Asp  Tyr  Ile  Ala  Leu  Asn  Glu
          115                      120                      125

Asp  Leu  Arg  Ser  Trp  Thr  Ala  Ala  Asp  Met  Ala  Ala  Gln  Ile  Thr  Lys
     130                      135                 140

Arg  Lys  Trp  Glu  Ala  Val  His  Ala  Ala  Glu  Gln  Arg  Arg  Val  Tyr  Leu
145                      150                      155                          160

Glu  Gly  Thr  Cys  Val  Glu  Trp  Leu  Arg  Arg  Tyr  Leu  Glu  Asn  Gly  Lys
               165                      170                      175

Glu  Thr  Leu  Gln  Arg  Thr
               180
```

(2) INFORMATION FOR SEQ ID NO:167:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:167:

```
Gly  Ser  His  Ser  Met  Arg  Tyr  Phe  Tyr  Thr  Ser  Val  Ser  Arg  Pro  Gly
1                   5                   10                      15

Arg  Gly  Glu  Pro  Arg  Phe  Ile  Ala  Val  Gly  Tyr  Val  Asp  Asp  Thr  Gln
          20                      25                      30

Phe  Val  Arg  Phe  Asp  Ser  Asp  Ala  Ala  Ser  Gln  Arg  Met  Glu  Pro  Arg
          35                      40                 45

Ala  Pro  Trp  Ile  Glu  Gln  Glu  Gly  Pro  Glu  Tyr  Trp  Asp  Leu  Gln  Thr
     50                       55                      60

Arg  Asn  Val  Lys  Ala  His  Ser  Gln  Thr  Asp  Arg  Ala  Asn  Leu  Gly  Thr
65                            70                 75                           80

Leu  Arg  Gly  Tyr  Tyr  Asn  Gln  Ser  Glu  Asp  Gly  Ser  His  Thr  Ile  Gln
                    85                      90                             95

Arg  Met  Tyr  Gly  Cys  Asp  Val  Gly  Pro  Asp  Gly  Arg  Phe  Leu  Arg  Gly
               100                 105                          110

Tyr  Gln  Gln  Asp  Ala  Tyr  Asp  Gly  Lys  Asp  Tyr  Ile  Ala  Leu  Asn  Glu
          115                      120                      125

Asp  Leu  Arg  Ser  Trp  Thr  Ala  Ala  Asp  Met  Ala  Ala  Gln  Ile  Thr  Gln
     130                      135                 140

Arg  Lys  Trp  Glu  Thr  Ala  His  Glu  Ala  Glu  Gln  Trp  Arg  Ala  Tyr  Leu
145                      150                      155                          160

Glu  Gly  Arg  Cys  Val  Glu  Trp  Leu  Arg  Arg  Tyr  Leu  Glu  Asn  Gly  Lys
               165                      170                      175

Glu  Thr  Leu  Gln  Arg  Thr
               180
```

(2) INFORMATION FOR SEQ ID NO:168:

(i) SEQUENCE CHARACTERISTICS:
(A) LENGTH: 182 amino acids (B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:168:

| Gly | Ser | His | Ser | Met | Arg | Tyr | Phe | Tyr | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |
| Arg | Gly | Glu | Pro | Arg | Phe | Ile | Ala | Val | Gly | Tyr | Val | Asp | Asp | Thr | Gln |
| | | | 20 | | | | | 25 | | | | | 30 | | |
| Phe | Val | Arg | Phe | Asp | Ser | Asp | Ala | Ala | Ser | Gln | Arg | Met | Glu | Pro | Arg |
| | | 35 | | | | | 40 | | | | | 45 | | | |
| Ala | Pro | Trp | Ile | Glu | Gln | Glu | Gly | Pro | Glu | Tyr | Trp | Asp | Arg | Asn | Thr |
| | 50 | | | | | 55 | | | | | 60 | | | | |
| Arg | Asn | Val | Lys | Ala | Gln | Ser | Gln | Thr | Asp | Arg | Val | Asp | Leu | Gly | Thr |
| 65 | | | | | 70 | | | | | 75 | | | | | 80 |
| Leu | Arg | Gly | Tyr | Tyr | Asn | Gln | Ser | Glu | Asp | Gly | Ser | His | Thr | Ile | Gln |
| | | | | 85 | | | | | 90 | | | | | 95 | |
| Arg | Met | Tyr | Gly | Cys | Asp | Val | Gly | Pro | Asp | Gly | Arg | Phe | Leu | Arg | Gly |
| | | | 100 | | | | | 105 | | | | | 110 | | |
| Tyr | Gln | Gln | Asp | Ala | Tyr | Asp | Gly | Lys | Asp | Tyr | Ile | Ala | Leu | Asn | Glu |
| | | | 115 | | | | | 120 | | | | | 125 | | |
| Asp | Leu | Arg | Ser | Trp | Thr | Ala | Ala | Asp | Met | Ala | Ala | Gln | Ile | Thr | Gln |
| | | 130 | | | | | 135 | | | | | 140 | | | |
| Arg | Lys | Trp | Glu | Thr | Ala | His | Glu | Ala | Glu | Gln | Trp | Arg | Ala | Tyr | Leu |
| 145 | | | | | 150 | | | | | 155 | | | | | 160 |
| Glu | Gly | Arg | Cys | Val | Glu | Trp | Leu | Arg | Arg | Tyr | Leu | Glu | Asn | Gly | Lys |
| | | | | 165 | | | | | 170 | | | | | 175 | |
| Glu | Thr | Leu | Gln | Arg | Thr |
| | | | 180 | | |

(2) INFORMATION FOR SEQ ID NO:169:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:169:

| Gly | Ser | His | Ser | Met | Arg | Tyr | Phe | Tyr | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |
| Arg | Gly | Glu | Pro | Arg | Phe | Ile | Ala | Val | Gly | Tyr | Val | Asp | Asp | Thr | Gln |
| | | | 20 | | | | | 25 | | | | | 30 | | |
| Phe | Val | Arg | Phe | Asp | Ser | Asp | Ala | Ala | Ser | Gln | Arg | Met | Glu | Pro | Arg |
| | | 35 | | | | | 40 | | | | | 45 | | | |
| Ala | Pro | Trp | Ile | Glu | Gln | Glu | Gly | Pro | Glu | Tyr | Trp | Asp | Arg | Asn | Thr |
| | 50 | | | | | 55 | | | | | 60 | | | | |
| Arg | Asn | Val | Lys | Ala | Gln | Ser | Gln | Thr | Asp | Arg | Val | Asp | Leu | Gly | Thr |
| 65 | | | | | 70 | | | | | 75 | | | | | 80 |
| Leu | Arg | Gly | Tyr | Tyr | Asn | Gln | Ser | Glu | Ala | Gly | Ser | His | Thr | Ile | Gln |
| | | | | 85 | | | | | 90 | | | | | 95 | |
| Arg | Met | Tyr | Gly | Cys | Asp | Val | Gly | Pro | Asp | Gly | Arg | Phe | Leu | Arg | Gly |
| | | | 100 | | | | | 105 | | | | | 110 | | |
| Tyr | Gln | Gln | Asp | Ala | Tyr | Asp | Gly | Lys | Asp | Tyr | Ile | Ala | Leu | Asn | Glu |
| | | | 115 | | | | | 120 | | | | | 125 | | |
| Asp | Leu | Arg | Ser | Trp | Thr | Ala | Ala | Asp | Met | Ala | Ala | Gln | Ile | Thr | Gln |

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |
| Arg | Lys | Trp | Glu | Thr | Ala | His | Glu | Ala | Glu | Gln | Trp | Arg | Ala | Tyr | Leu |
| 145 |     |     |     |     | 150 |     |     |     |     | 155 |     |     |     |     | 160 |
| Glu | Gly | Glu | Cys | Val | Glu | Trp | Leu | Arg | Arg | Tyr | Leu | Glu | Asn | Gly | Lys |
|     |     |     |     | 165 |     |     |     |     | 170 |     |     |     |     | 175 |     |
| Glu | Thr | Leu | Gln | Arg | Thr |     |     |     |     |     |     |     |     |     |     |
|     |     |     |     | 180 |     |     |     |     |     |     |     |     |     |     |     |

( 2 ) INFORMATION FOR SEQ ID NO:170:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:170:

| Gly | Ser | His | Ser | Met | Arg | Tyr | Phe | Tyr | Thr | Ser | Val | Ser | Arg | Pro | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Arg | Gly | Glu | Pro | Arg | Phe | Ile | Ala | Val | Gly | Tyr | Val | Asp | Asp | Thr | Gln |
|     |     |     |     | 20  |     |     |     |     | 25  |     |     |     |     | 30  |     |
| Phe | Val | Arg | Phe | Asp | Ser | Asp | Ala | Ala | Ser | Gln | Arg | Met | Glu | Pro | Arg |
|     |     |     |     | 35  |     |     |     |     | 40  |     |     |     |     | 45  |     |
| Ala | Pro | Trp | Ile | Glu | Gln | Glu | Gly | Pro | Glu | Tyr | Trp | Asp | Arg | Asn | Thr |
|     |     |     |     | 50  |     |     |     |     | 55  |     |     |     |     | 60  |     |
| Arg | Asn | Val | Lys | Ala | Gln | Ser | Gln | Thr | Asp | Arg | Val | Asp | Leu | Gly | Thr |
| 65  |     |     |     |     | 70  |     |     |     |     | 75  |     |     |     |     | 80  |
| Leu | Arg | Gly | Tyr | Tyr | Asn | Gln | Ser | Glu | Ala | Gly | Ser | His | Thr | Ile | Gln |
|     |     |     |     | 85  |     |     |     |     | 90  |     |     |     |     | 95  |     |
| Met | Met | Tyr | Gly | Cys | Asp | Val | Gly | Ser | Asp | Gly | Arg | Phe | Leu | Arg | Gly |
|     |     |     |     | 100 |     |     |     |     | 105 |     |     |     |     | 110 |     |
| Tyr | Arg | Gln | Asp | Ala | Tyr | Asp | Gly | Lys | Asp | Tyr | Ile | Ala | Leu | Lys | Glu |
|     |     |     |     | 115 |     |     |     |     | 120 |     |     |     |     | 125 |     |
| Asp | Leu | Arg | Ser | Trp | Thr | Ala | Ala | Asp | Met | Ala | Ala | Gln | Thr | Thr | Lys |
|     |     |     |     | 130 |     |     |     |     | 135 |     |     |     |     | 140 |     |
| His | Lys | Trp | Glu | Ala | Ala | His | Val | Ala | Glu | Gln | Trp | Arg | Ala | Tyr | Leu |
| 145 |     |     |     |     | 150 |     |     |     |     | 155 |     |     |     |     | 160 |
| Glu | Gly | Thr | Cys | Val | Glu | Trp | Leu | Arg | Arg | Tyr | Leu | Glu | Asn | Gly | Lys |
|     |     |     |     | 165 |     |     |     |     | 170 |     |     |     |     | 175 |     |
| Glu | Thr | Leu | Gln | Arg | Thr |     |     |     |     |     |     |     |     |     |     |
|     |     |     |     | 180 |     |     |     |     |     |     |     |     |     |     |     |

( 2 ) INFORMATION FOR SEQ ID NO:171:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:171:

| Gly | Ser | His | Ser | Met | Arg | Tyr | Phe | Tyr | Thr | Ser | Met | Ser | Arg | Pro | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Arg | Gly | Glu | Pro | Arg | Phe | Ile | Ala | Val | Gly | Tyr | Val | Asp | Asp | Thr | Gln |
|     |     |     |     | 20  |     |     |     |     | 25  |     |     |     |     | 30  |     |
| Phe | Val | Arg | Phe | Asp | Ser | Asp | Ala | Ala | Ser | Gln | Arg | Met | Glu | Pro | Arg |
|     |     |     |     | 35  |     |     |     |     | 40  |     |     |     |     | 45  |     |

| Ala | Pro | Trp | Ile | Glu | Gln | Glu | Gly | Pro | Glu | Tyr | Trp | Asp | Arg | Asn | Thr |
|---|---|---|---|---|---|---|---|---|---|---|---|---|---|---|---|
| | 50 | | | | | 55 | | | | | 60 | | | | |

| Arg | Asn | Val | Lys | Ala | Gln | Ser | Gln | Thr | Asp | Arg | Val | Asp | Leu | Gly | Thr |
|---|---|---|---|---|---|---|---|---|---|---|---|---|---|---|---|
| 65 | | | | | 70 | | | | 75 | | | | | | 80 |

| Leu | Arg | Gly | Tyr | Tyr | Asn | Gln | Ser | Glu | Ala | Gly | Ser | His | Thr | Ile | Gln |
|---|---|---|---|---|---|---|---|---|---|---|---|---|---|---|---|
| | | | | 85 | | | | | 90 | | | | | 95 | |

| Arg | Met | Tyr | Gly | Cys | Asp | Val | Gly | Pro | Asp | Gly | Arg | Phe | Leu | Arg | Gly |
|---|---|---|---|---|---|---|---|---|---|---|---|---|---|---|---|
| | | | 100 | | | | | 105 | | | | | 110 | | |

| Tyr | His | Gln | Tyr | Ala | Tyr | Asp | Gly | Lys | Asp | Tyr | Ile | Ala | Leu | Lys | Glu |
|---|---|---|---|---|---|---|---|---|---|---|---|---|---|---|---|
| | | 115 | | | | | 120 | | | | | 125 | | | |

| Asp | Leu | Arg | Ser | Trp | Thr | Ala | Ala | Asp | Met | Ala | Ala | Gln | Thr | Thr | Lys |
|---|---|---|---|---|---|---|---|---|---|---|---|---|---|---|---|
| | 130 | | | | | 135 | | | | | 140 | | | | |

| His | Lys | Trp | Glu | Ala | Ala | His | Val | Ala | Glu | Gln | Trp | Arg | Ala | Tyr | Leu |
|---|---|---|---|---|---|---|---|---|---|---|---|---|---|---|---|
| 145 | | | | | 150 | | | | | 155 | | | | | 160 |

| Glu | Gly | Thr | Cys | Val | Glu | Trp | Leu | Arg | Arg | Tyr | Leu | Glu | Asn | Gly | Lys |
|---|---|---|---|---|---|---|---|---|---|---|---|---|---|---|---|
| | | | | 165 | | | | | 170 | | | | | 175 | |

| Glu | Thr | Leu | Gln | Arg | Thr |
|---|---|---|---|---|---|
| | | | 180 | | |

( 2 ) INFORMATION FOR SEQ ID NO:172:

( i ) SEQUENCE CHARACTERISTICS:
( A ) LENGTH: 182 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:172:

| Gly | Ser | His | Ser | Met | Arg | Tyr | Phe | Tyr | Thr | Ser | Val | Ser | Arg | Pro | Gly |
|---|---|---|---|---|---|---|---|---|---|---|---|---|---|---|---|
| 1 | | | | 5 | | | | | 10 | | | | | 15 | |

| Arg | Gly | Glu | Pro | Arg | Phe | Ile | Ala | Val | Gly | Tyr | Val | Asp | Asp | Thr | Gln |
|---|---|---|---|---|---|---|---|---|---|---|---|---|---|---|---|
| | | | 20 | | | | | 25 | | | | | 30 | | |

| Phe | Val | Arg | Phe | Asp | Ser | Asp | Ala | Ala | Ser | Gln | Arg | Met | Glu | Pro | Arg |
|---|---|---|---|---|---|---|---|---|---|---|---|---|---|---|---|
| | | | 35 | | | | | 40 | | | | | 45 | | |

| Ala | Pro | Trp | Ile | Glu | Gln | Glu | Gly | Pro | Glu | Tyr | Trp | Asp | Arg | Asn | Thr |
|---|---|---|---|---|---|---|---|---|---|---|---|---|---|---|---|
| | 50 | | | | | 55 | | | | | 60 | | | | |

| Arg | Asn | Val | Lys | Ala | Gln | Ser | Gln | Thr | Asp | Arg | Val | Asp | Leu | Gly | Thr |
|---|---|---|---|---|---|---|---|---|---|---|---|---|---|---|---|
| 65 | | | | | 70 | | | | 75 | | | | | | 80 |

| Leu | Arg | Gly | Tyr | Tyr | Asn | Gln | Ser | Glu | Ala | Gly | Ser | His | Thr | Val | Gln |
|---|---|---|---|---|---|---|---|---|---|---|---|---|---|---|---|
| | | | | 85 | | | | | 90 | | | | | 95 | |

| Arg | Met | Tyr | Gly | Cys | Asp | Val | Gly | Ser | Asp | Trp | Arg | Phe | Leu | Arg | Gly |
|---|---|---|---|---|---|---|---|---|---|---|---|---|---|---|---|
| | | | 100 | | | | | 105 | | | | | 110 | | |

| Tyr | His | Gln | Tyr | Ala | Tyr | Asp | Gly | Lys | Asp | Tyr | Ile | Ala | Leu | Lys | Glu |
|---|---|---|---|---|---|---|---|---|---|---|---|---|---|---|---|
| | | 115 | | | | | 120 | | | | | 125 | | | |

| Asp | Leu | Arg | Ser | Trp | Thr | Ala | Ala | Asp | Met | Ala | Ala | Gln | Thr | Thr | Lys |
|---|---|---|---|---|---|---|---|---|---|---|---|---|---|---|---|
| | 130 | | | | | 135 | | | | | 140 | | | | |

| His | Lys | Trp | Glu | Ala | Ala | His | Val | Ala | Glu | Gln | Leu | Arg | Ala | Tyr | Leu |
|---|---|---|---|---|---|---|---|---|---|---|---|---|---|---|---|
| 145 | | | | | 150 | | | | | 155 | | | | | 160 |

| Glu | Gly | Thr | Cys | Val | Glu | Trp | Leu | Arg | Arg | Tyr | Leu | Glu | Asn | Gly | Lys |
|---|---|---|---|---|---|---|---|---|---|---|---|---|---|---|---|
| | | | | 165 | | | | | 170 | | | | | 175 | |

| Glu | Thr | Leu | Gln | Arg | Thr |
|---|---|---|---|---|---|
| | | | 180 | | |

( 2 ) INFORMATION FOR SEQ ID NO:173:

( i ) SEQUENCE CHARACTERISTICS:
( A ) LENGTH: 182 amino acids
( B ) TYPE: amino acid (C) STRANDEDNESS: single
(D) TOPOLOGY: linear (ii) MOLECULE TYPE: DNA (genomic)

(xi) SEQUENCE DESCRIPTION: SEQ ID NO:173:

```
Gly Ser His Ser Met Arg Tyr Phe Phe Thr Ser Val Ser Arg Pro Gly
 1           5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gln Glu Thr
    50                  55                  60

Arg Asn Val Lys Ala His Ser Gln Thr Asp Arg Val Asp Leu Gly Thr
65                  70                  75                  80

Leu Arg Gly Tyr Tyr Asn Gln Ser Glu Ala Gly Ser His Thr Ile Gln
                85                  90                  95

Met Met Tyr Gly Cys Asp Val Gly Pro Asp Gly Arg Leu Leu Arg Gly
            100                 105                 110

Tyr Gln Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr
            180
```

METHODS AND REAGENTS FOR HLA CLASS I A LOCUS DNA TYPING

This application is continuation-in-part of U.S. Ser. No. 07/788,113, filed Nov. 5, 1991 which is now abandoned.

BACKGROUND OF THE INVENTION

1. Field of the Invention

The present invention relates to the field of molecular biology and nucleic acid chemistry. More specifically, it relates to methods and reagents for genotyping at the HLA Class I A locus. The invention therefore has applications in the fields of medicine generally, medical research and diagnostics specifically, transplantation biology, forensic science, and molecular biology.

2. Description of Related Art

The major histocompatibility complex (MHC) includes a number of genes that encode glycoproteins that, together with the T cell receptor (TCR), are the key elements of specificity in the T cell response to foreign and self antigens. There are two structurally distinct, but related, families of MHC molecules that present antigens to two subsets of T cells: Class 1 MHC molecules present antigens to T cells that express the CD8 cell surface glycoprotein, and Class II MHC molecules present antigens to T cells that express the CD4 cell surface glycoprotein. See Bjorkman and Parham, 1990, *Ann. Rev. Biochem.* 59:253-288, incorporated herein by reference. For a general review of the HLA Class II genes and proteins, see Trowsdale et al., 1985, *Immunol. Rev.* 85:5; and Giles and Capra, 1985, *Adv. Immunol.* 37:1, both incorporated herein by reference.

The Class I gene products function as restriction elements in the presentation of mainly endogenous peptides to cytotexic T lymphocytes and are a major barrier for allogeneic tissue transplantation. Accurate determination of allelic subtypes is essential for typing potential transplantation donors, where very precise HLA matching of the donor and the transplant recipient appears to be critical in minimizing risk of rejection or graft versus host disease.

Significant advances have been made in developing DNA based typing methods for determining the HLA Class II genotype of an individual. The polymerase chain reaction is used to amplify a region nucleic acid encompassing a polymorphism and alleles are detected using sequence-specific oligonucleotide probes. For example, see Saiki et al., 1986, *Nature* 324:163; and Bugawan et al, 1988, *J. Immunol.* 141:4024-4030, both incorporated herein by reference. Some of these DNA based typing methods are now commercially available for forensic, research and clinical use.

In contrast to the advances made in the field of Class H HLA DNA typing, very little progress has been made in developing methods for Class I HLA DNA typing. One reason for this lack of progress is the complexity of the HLA Class I genes. The Class I genes encode the A, B, C, D, E, F, and G proteins, as well as other less well characterized products. The A, B, C, and E loci are known to encode approximately 41, 76, 18 and 4 different alleles, respectively. The F and G loci are currently not believed to be polymorphic. The currently known differences are primarily in the second and third exons of these genes (see Zemmour and Parham, 1991, *Immunogenetics* 33:310-320, incorporated herein by reference), although sequence variation in the fourth exon of these Class I genes is also known. See also Malissen et al., February, 1982, *Proc. Natl. Acad. Sci USA* 79:893-897, incorporated herein by reference.

Fernandez-Vina et al, 1992, *Human Immunol.* 33:163-173 describe a DNA typing system that uses sequence-specific amplification and detection by probe hybridization to distinguish 11 alleles of the HLA A2 and A28 groups. Browning et al., 1993, *Proc. Natl. Acad. Sci USA* 90:2842-2845 describe an HLA-A typing method which relies solely on sequence-specific amplification with a panel of primers. Oh et al, 1993, *Tissue Antigens* 41:135-142 describe an HLA-A typing system that includes amplification of part of the second and the third exon of the HLA-A locus (a region of HLA-H was co-amplified) and allele detection by hybridization with a panel of 28 probes. A number of isotypes previously defined by serology and isoelectric focusing could be defined by the patterns of hybridization. Each of these typing system is limited in the number of types that can be identified.

There is a need for a simple and rapid HLA-A typing system that can distinguish a greater number of alleles and genotypes.

SUMMARY OF THE INVENTION

The present invention provides methods and reagents for typing HLA Class I A Locus nucleic acids. The invention enables one to type homozygous or heterozygous samples from a variety of sources, including samples comprising RNA or cDNA templates, and to detect allelic variants not distinguishable by present serological, cellular, or biochemical methods. The present typing system facilitates typing tissue for transplantation, determining individual identity, and identifying disease susceptible individuals.

In one aspect, the present invention provides a method for determining the HLA-A alleles present in a sample containing HLA-A nucleic acid, which method comprises:

(a) hybridizing the nucleic acid to a panel of oligonucleotide probes under conditions such that the probes hybridize only to exactly complementary sequences, wherein said panel consists of probes which hybridize to second and third exon nucleic acid, and wherein said probes are capable of detecting at least 31 out of the 36 homozygous genotypes and 602 out of the 630 heterozygous genotypes that are possible from the 36 alleles consisting of the HLA alleles:

0101 (Seq ID Nos. 53 and 94), 0201 (Seq ID Nos. 54 and 95), 0202 (Seq ID Nos. 55 and 96), 0203 (Seq ID Nos. 56 and 97), 0204 (Seq ID Nos. 57 and 98), 0205 (Seq ID Nos. 58 and 99), 0206 (Seq ID Nos. 59 and 100), 0210 (Seq ID Nos. 60 and 101), 0211 (Seq ID Nos. 61 and 102), 0212 (Seq ID Nos. 62 and 103), 0301 (Seq ID Nos. 63 and 104), 0302 (Seq ID Nos. 64 and 105), 1101 (Seq ID Nos. 65 and 106), 1102 (Seq ID Nos. 66 and 107), 2301 (seq ID Nos. 67 and 108), 2401/02 (Seq ID Nos. 68 and 109/

Seq ID Nos. 69 and 110), 2403 (Seq ID Nos. 70 and 111 ), 2501 (Seq ID Nos. 71 and 112), 2601 (Seq ID Nos. 72 and 113), 2901/02 (Seq ID Nos. 73 and 114/Seq ID Nos. 74 and 115), 3001 (Seq ID Nos. 75 and 116), 3002 (Seq ID Nos. 76 and 117), 3003 (Seq ID Nos. 77 and 118), 3101 (Seq ID Nos. 78, 79, 119, and 120), 3201 (Seq ID Nos. 80 and 121), 3301 (Seq ID Nos. 81 and 122), 3401 (Seq ID Nos. 82 and 123), 3402 (Seq ID Nos. 83 and 124), 3601 (Seq ID Nos. 84 and 125), 4301 (Seq ID Nos. 85 and 126), 6601 (Seq ID Nos. 86 and 127), 6602 (Seq ID Nos. 87 and 128), 6801 (Seq ID Nos. 88, 89, 129, and 130), 6802 (Seq ID Nos. 90 and 131), 6901 (Seq ID Nos. 91 and 132), 7401 (Seq ID Nos. 92 and 133); and (b) determining the HLA-A alleles present in the sample from the patterns of probe hybridization in step (a).

In one embodiment of the invention, a reverse dot blot hybridization format is used in step (b) in which 50 sequence-specific oligonucleotide probes are immobilized on a nylon membrane.

In a preferred embodiment, the second and third exons of the HLA-A locus are amplified using the polymerase chain reaction (PCR).

Another aspect of the invention relates to oligonucleotide primers which enable the PCR amplification of the second and third exons of the HLA-A locus and do not coamplify regions of other HLA Class I loci.

Another aspect of the invention relates to a panel of sequence-specific oligonucleotide probes, wherein said probes are capable of detecting at least 31 out of the 36 homozygous genotypes and 602 out of the 630 heterozygous genotypes that are possible from the 36 alleles consisting of the HLA alleles:

0101 (Seq ID Nos. 53 and 94), 0201 (Seq ID Nos. 54 and 95), 0202 (Seq ID Nos. 55 and 96), 0203 (Seq ID Nos. 56 and 97), 0204 (Seq ID Nos. 57 and 98), 0205 (Seq ID Nos. 58 and 99), 0206 (Seq ID Nos. 59 and 100), 0210 (Seq ID Nos. 60 and 101), 0211 (Seq ID Nos. 61 and 102), 0212 (Seq ID Nos. 62 and 103), 0301 (Seq ID Nos. 63 and 104), 0302 (Seq ID Nos. 64 and 105), 1101 (Seq ID Nos. 65 and 106), 1102 (Seq ID Nos. 66 and 107), 2301 (seq ID Nos. 67 and 108), 2401/02 (Seq ID Nos. 68 and 109/

Seq ID Nos. 69 and 1 10), 2403 (Seq ID Nos. 70 and 111), 2501 (Seq ID Nos. 71 and 112), 2601 (Seq ID Nos. 72 and 113), 2901/02 (Seq ID Nos. 73 and 114/Seq ID Nos. 74 and 115), 3001 (Seq ID Nos. 75 and 116), 3002 (Seq ID Nos. 76 and 117), 3003 (Seq ID Nos. 77 and 118), 3101 (Seq ID Nos. 78, 79, 119, and 120), 3201 (Seq ID Nos. 80 and 121), 3301 (Seq ID Nos. 81 and 122), 3401 (Seq ID Nos. 82 and 123), 3402 (Seq ID Nos. 83 and 124), 3601 (Seq ID Nos. 84 and 125), 4301 (Seq ID Nos. 85 and 126), 6601 (Seq ID Nos. 86 and 127), 6602 (Seq ID Nos. 87 and 128), 6801 (Seq ID Nos. 88, 89, 129, and 130), 6802 (Seq ID Nos. 90 and 131), 6901 (Seq ID Nos. 91 and 132), 7401 (Seq ID Nos. 92 and 133)

Another aspect of the invention relates to kits for practicing the methods, that together provide a rapid, simple and precise system for typing the alleles of the HLA-A locus, including those that cannot be distinguished by serological methods. These kits take a variety of forms and comprise one or more probes and, in one embodiment, comprise a panel of probes sufficient to determine the HLA-A genotype. The kits can also comprise one or more amplification reagents, e.g., primers, polymerase, buffers, and nucleoside triphosphates.

BRIEF DESCRIPTION OF THE FIGURES

FIG. 1 provides the pattern of probe hybridization for each HLA-A allele with the probes of Table 2A.

FIG. 2 provides the pattern of probe hybridization for each HLA-A allele with the probes of Table 2B.

DETAILED DESCRIPTION OF THE INVENTION

To aid in understanding the invention, several terms are defined below.

The terms "HLA-A gene" and "HLA-A locus" refer to a transcribed region of DNA that contains the coding sequence for the HLA Class I A protein and the untranslated intervening sequences.

The term "alleles" refers to variants of the nucleotide sequence of a gene. An allele is defined by the presence of a specific subsequence, which may not include the entire gene. Alleles are defined herein by the variation in the second and third exons only.

The term "genotype" refers to a description of the alleles of a gene contained in an individual or a sample.

The terms "polymorphic" and "polymorphism," as used herein, refer to the condition in which two or more variants of a specific DNA sequence can be found in a population.

The terms "polymorphic gene" and "polymorphic region" refer to that region of the DNA where a polymorphism occurs.

The term "epitope," as used herein, refers to an amino acid subsequence of the HLA-A protein.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide," and these terms will be used interchangeably. These terms refer only to the primary structure of the molecule. Thus, these terms include double- and single-stranded DNA, as well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "hybridization" refers to the formation of a duplex structure by two single stranded nucleic acids due to complementary base pairing. Hybridization can occur between complementary nucleic acid strands or between nucleic acid strands that contain minor regions of mismatch. Conditions under which only complementary nucleic acid strands will hybridize are referred to as "stringent hybridization conditions." Two single-stranded nucleic acids that are complementary except for minor regions of mismatch am referred to as "substantially complementary." Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs.

The term "probe" refers to a oligonucleotide which forms a duplex structure with a sequence of a target nucleic acid due to complementary base pairing. The probe will contain a "hybridizing region," which is a region of the oligonucleotide preferably consisting of 10 to 50 nucleotides, more preferably from 15 to 30 nucleotides, corresponding to a region of the target sequence. "Corresponding" means identical to or complementary to the designated nucleic acid. A probe oligonucleotide can either consist entirely of the hybridizing region or can contain additional features which allow for the detection or immobilization of the probe but do not alter the hybridization characteristics of the hybridizing region.

The terms "sequence-specific oligonucleotide" and "SSO" refer to oligonucleotide probes wherein the hybridizing region is exactly complementary to the sequence to be detected. The use of stringent hybridization conditions under which the probe will hybridize only to that exactly complementary target sequence allows the detection of the specific target sequence. Stringent hybridization conditions are well known in the art (see, e.g., Sambrook et al., 1985, *Molecular Cloning—A Laboratory Manual,* Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Typically, stringent conditions will be those in which the salt concentration is at least about 0.2 molar at pH 7 and the temperature is at least 55° C. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis.

The term "target region" refers to a region of a nucleic acid which is to be analyzed and usually includes a polymorphic region.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. A purified thermostable polymerase enzyme is described more fully in U.S. Pat. No. 4,889,818, incorporated herein by reference, and is commercially available from Perkin-Elmer, Norwalk, Conn.

The present invention provides a Class I HLA-A DNA typing system and sequence-specific oligonucleotide probes (SSOs) for analyzing HLA-A alleles. The invention can be used to type DNA containing samples from a variety of sources, including cDNA templates, and can be used to detect allelic variants not distinguishable by serological methods. This typing system can utilize a dot-blot format that is simple and rapid to perform, produces detectable signals in minutes, and will prove valuable for tissue typing and determining individual identity and disease susceptibility.

In one embodiment, the invention provides a method for detecting and distinguishing among most of the alleles of the HLA-A gene that have been sequenced at the DNA level that might be present in a sample. The present invention enables detection of new alleles and, after the invention becomes widely practiced, new alleles will most likely be discovered. In a preferred embodiment, two PCR primers and a large number of oligonucleotide probes provide for the identification of many different HLA-A second and third exon sequence variants that are uniquely characteristic of the HLA-A alleles. The pattern of probe hybridization can be scanned and analyzed with computer assistance, facilitating the identification of the HLA-A alleles.

The diversity of the Class I HLA genes and the large number of alleles of these genes in the population make difficult the process of identifying the particular HLA-A alleles present in a human nucleic acid sample. The present invention enables type determination with great specificity. The invention can be used to identify the particular individual from whom a sample originated. This discrimination power in turn leads to the applications of the invention in the field of forensic science.

Because PCR can be used to amplify very small amounts of DNA, the present invention can be used to type HLA-A DNA from a wide variety of sources including buccal swabs, and single hairs.

HLA-A Alleles

Currently, there are 41 HLA-A alleles known as defined by nucleic acid sequence variation. The nucleic acid sequence variation defining 3 of the alleles consists entirely of silent mutations; only 38 alleles are known as defined by amino acid sequence variation. Nucleotide sequence alleles 31011 (Seq ID Nos. 78 and 119) and 31012 (Seq ID Nos. 79 and 120) both encode the same amino acid sequence allele, 3101 (Seq ID Nos. 16 1 and 200). Similarly, nucleotide sequence alleles 68011 (Seq ID Nos. 88 and 129) and 68012 (Seq ID Nos. 89 and 130) both encode the 6801 (Seq ID Nos. 170 and 209) amino acid sequence allele. The exemplified system is designed to discriminate among those 38 alleles which encode amino acid sequence variations.

The nucleotide variation that distinguishes alleles 2401 (Seq ID Nos. 68 and 109) and 2402 (Seq ID Nos. 69 and 110) occurs in the primer binding region when the alleles are amplified with the exemplified primers; the allele sequences are identical in the intervening region. Because alleles are herein defined by their second and third exon sequences, alleles 2401 (Seq ID Nos. 68 and 109) and 2402 (Seq ID Nos. 69 and 110) cannot be distinguished and are considered to be the same allele.

Sequence alignment of the nucleotide sequences, shown 5' to 3', and the corresponding amino acid sequences of a region of the HLA-A allele is provided below.

TABLE 1A

Exon 2

| Seq ID No. | 1 | 20 | 40 |
|---|---|---|---|
| A*0101 | 53 | ---------------------------------------- |
| A*0201 | 54 | --------T----------A------------------- |
| A*0202 | 55 | --------T----------A------------------- |
| A*0203 | 56 | --------T----------A------------------- |
| A*0204 | 57 | --------T----------A------------------- |
| A*0205 | 58 | --------T----------A------------------- |
| A*0206 | 59 | --------T----------A------------------- |
| A*0210 | 60 | ---------------------------------------- |
| A*0211 | 61 | --------T----------A------------------- |
| A*0212 | 62 | --------T----------A------------------- |
| A*0301 | 63 | --------T----------A------------------- |
| A*0302 | 64 | --------T----------A------------------- |
| A*1101 | 65 | ---------------------------------------- |
| A*1102 | 66 | ---------------------------------------- |
| A*2301 | 67 | ------------------C-A------------------- |
| A*2401 | 68 | ------------------C-A------------------- |
| A*2402 | 69 | ------------------C-A------------------- |
| A*2403 | 70 | ------------------C-A------------------- |
| A*2501 | 71 | ---------------------------------------- |
| A*2601 | 72 | ---------------------------------------- |
| A*2901 | 73 | -----------------AC--A------------------- |
| A*2902 | 74 | -----------------AC--A------------------- |
| A*3001 | 75 | --------T---------T--A------------------- |
| A*3002 | 76 | ------------------C--A------------------- |
| A*3003 | 77 | ------------------C--A------------------- |
| A*31011 | 78 | -----------------AC--A------------------- |
| A*31012 | 79 | -----------------AC--A------------------- |
| A*3201 | 80 | -----------------AC--A------------------- |
| A*3301 | 81 | -----------------T---A------------------- |
| A*3401 | 82 | -----------------AC--A------------------- |
| A*3402 | 83 | -----------------AC--A------------------- |
| A*3601 | 84 | --------T---------T--A------------------- |
| A*4301 | 85 | ---------------------------------------- |
| A*6601 | 86 | ---------------------------------------- |
| A*6602 | 87 | ---------------------------------------- |
| A*68011 | 88 | ---------------------------------------- |
| A*68012 | 89 | ---------------------------------------- |
| A*6802 | 90 | ---------------------------------------- |
| A*6901 | 91 | ------------------------------------T--- |
| A*7401 | 92 | -----------------T---A------------------- |
| * | 93 | GCTCCCACTCCATGAGGTATTTCTACACCTCCGTGTCCCGGCCCG |

| Seq ID No. | 60 | 80 |
|---|---|---|
| A*0101 | 53 | ------------------------------------- |
| A*0201 | 54 | ------------C------------------------- |
| A*0202 | 55 | --------------------------------------- |
| A*0203 | 56 | --------------------------------------- |
| A*0204 | 57 | --------------------------------------- |
| A*0205 | 58 | --------------------------------------- |
| A*0206 | 59 | --------------------------------------- |

TABLE 1A-continued

Exon 2

| | | | | |
|---|---|---|---|---|
| A*0210 | 60 | ------------------------------ | ------------------------------ | |
| A*0211 | 61 | ------------------------------ | ------------------------------ | |
| A*0212 | 62 | ------------------------------ | ------------------------------ | |
| A*0301 | 63 | ------------------------------ | ------------------------------ | |
| A*0302 | 64 | ------------------------------ | ------------------------------ | |
| A*1101 | 65 | ------------------------------ | ------------------------------ | |
| A*1102 | 66 | --------------A--------------- | ------------------------------ | |
| A*2301 | 67 | ------------C----------------- | ------------------------------ | |
| A*2401 | 68 | ------------C----------------- | ------------------------------ | |
| A*2402 | 69 | ------------C----------------- | ------------------------------ | |
| A*2403 | 70 | ------------C----------------- | ------------------------------ | |
| A*2501 | 71 | ------------C----------------- | ------------------------------ | |
| A*2601 | 72 | ------------------------------ | ------------------------------ | |
| A*2901 | 73 | ------------C----------------- | ------------------------------ | |
| A*2902 | 74 | ------------C----------------- | ------------------------------ | |
| A*3001 | 75 | --A--T--A-------------------- | ------------------------------ | |
| A*3002 | 76 | --A--T--A-------------------- | ------------------------------ | |
| A*3003 | 77 | --A--T--A-------------------- | ------------------------------ | |
| A*31011 | 78 | ------------------------------ | ------------------------------ | |
| A*31012 | 79 | ------------C----------------- | ------------------------------ | |
| A*3201 | 80 | ------------C----------------- | ------------------------------ | |
| A*3301 | 81 | ------------C----------------- | ------------------------------ | |
| A*3401 | 82 | ------------C----------------- | ------------------------------ | |
| A*3402 | 83 | ------------C----------------- | ------------------------------ | |
| A*3601 | 84 | ------------C----------------- | ------------------------------ | |
| A*4301 | 85 | ------------C----------------- | ------------------------------ | |
| A*6601 | 86 | ------------C----------------- | ------------------------------ | |
| A*6602 | 87 | ------------C----------------- | ------------------------------ | |
| A*68011 | 88 | ------------C----------------- | ------------------------------ | |
| A*68012 | 89 | ------------C----------------- | ------------------------------ | |
| A*6802 | 90 | ------------C----------------- | ------------------------------ | |
| A*6901 | 91 | ------------C----------------- | ------------------------------ | |
| A*7401 | 92 | ------------C----------------- | ------------------------------ | |
| * | 93 | GCCGCGGGGAGCCCCGCTTCATCGCGGACA | GTGGGCTACGTGGACGACA | |
| | | 100 | 120 | |

| | Seq ID No. | | |
|---|---|---|---|
| A*0101 | 53 | ------------------------------ | |
| A*0201 | 54 | ----------------------C---A-- | |
| A*0202 | 55 | ----------------------C---A-- | |
| A*0203 | 56 | ----------------------C---A-- | |
| A*0204 | 57 | ----------------------C---A-- | |
| A*0205 | 58 | ----------------------C---G-- | |
| A*0206 | 59 | ----------------------C---A-- | |
| A*0210 | 60 | ----------------------C---A-- | |
| A*0211 | 61 | ----------------------C---A-- | |
| A*0212 | 62 | ----------------------C---A-- | |
| A*0301 | 63 | ----------------------C---A-- | |
| A*0302 | 64 | ----------------------C---A-- | |
| A*1101 | 65 | ----------------------C---A-- | |
| A*1102 | 66 | ----------------------C---A-- | |
| A*2301 | 67 | ----------------------C---A-- | |
| A*2401 | 68 | ----------------------C---A-- | |

TABLE 1A-continued

Exon 2

| | Seq ID No. | | | | | |
|---|---|---|---|---|---|---|
| | | CGCAGTTCGTGCGGTTCGACACAGGAC | GCGCCGAGTCCGAGGATGG | | | |
| | | 140 | 160 | 180 | | |
| A*2402 | 69 | --------------------------- | ------------------- | --C--A------------- | | |
| A*2403 | 70 | --------------------------- | ------------------- | --C--A------------- | | |
| A*2501 | 71 | --------------------------- | ------------------- | --C--A------------- | | |
| A*2601 | 72 | --------------------------- | ------------------- | --C--A------------- | | |
| A*2901 | 73 | -------------T------------- | ------------------- | --C--A------------- | | |
| A*2902 | 74 | -------------T------------- | ------------------- | --C--A------------- | | |
| A*3001 | 75 | --------------------------- | ------------------- | --C--A------------- | | |
| A*3002 | 76 | --------------------------- | ------------------- | --C--A------------- | | |
| A*3003 | 77 | --------------------------- | ------------------- | --C--A------------- | | |
| A*31011 | 78 | --------------------------- | ------------------- | --C--A------------- | | |
| A*31012 | 79 | --------------------------- | ------------------- | --C--A------------- | | |
| A*3201 | 80 | -------------T------------- | ------------------- | --C--A------------- | | |
| A*3301 | 81 | --------------------------- | ------------------- | --C--A------------- | | |
| A*3401 | 82 | --------------------------- | ------------------- | --C--A------------- | | |
| A*3402 | 83 | --------------------------- | ------------------- | --C--A------------- | | |
| A*3601 | 84 | --------------------------- | ------------------- | --C--A------------- | | |
| A*4301 | 85 | --------------------------- | ------------------- | --C--A---------A--- | | |
| A*6601 | 86 | --------------------------- | ------------------- | --C--A------------- | | |
| A*6602 | 87 | --------------------------- | ------------------- | --C--A------------- | | |
| A*68011 | 88 | --------------------------- | ------------------- | --C--A------------- | | |
| A*68012 | 89 | --------------------------- | ------------------- | --C--A------------- | | |
| A*6802 | 90 | --------------------------- | ------------------- | --C--A------------- | | |
| A*6901 | 91 | --------------------------- | ------------------- | --C--A------------- | | |
| A*7401 | 92 | -------------T------------- | ------------------- | --C--A------------- | | |
| * | 93 | --------------------------- | ------------------- | --C--A------------- | | |
| A*0101 | 53 | | | | | |
| A*0201 | 54 | | -------T----------- | | | |
| A*0202 | 55 | | -------T----------- | | | |
| A*0203 | 56 | | -------T----------- | | | |
| A*0204 | 57 | | -------T----------- | | | |
| A*0205 | 58 | | -------T----------- | | | |
| A*0206 | 59 | | -------T----------- | | | |
| A*0210 | 60 | | -------T----------- | | | |
| A*0211 | 61 | | -------T----------- | | | |
| A*0212 | 62 | | -------T----------- | | | |
| A*0301 | 63 | | | | | |
| A*1101 | 64 | | | | | |
| A*1102 | 65 | | | | | |
| A*2301 | 66 | | | | | |
| A*2401 | 67 | | | | | |
| A*2402 | 68 | | | | | |
| A*2403 | 69 | | | | | |
| A*2501 | 70 | | | | | |
| A*2601 | 71 | | | | | |
| A*2901 | 72 | | | | | |
| A*2902 | 73 | ----------A---------------- | | | | |
| A*3001 | 74 | ----------A---------------- | | | | |
| A*3002 | 75 | | | ----A----T--------- | | |
| A*3003 | 76 | | | ----A----T--------- | | |

TABLE 1A-continued

Exon 2

| Allele | Seq ID No. | | |
|---|---|---|---|
| | | 200 | 220 |
| A*31011 | 78 | ---A---T--- | --- |
| A*31012 | 79 | ---A---T--- | --- |
| A*3201 | 80 | --- | --- |
| A*3301 | 81 | --- | --- |
| A*3401 | 82 | --- | --- |
| A*3402 | 83 | --- | --- |
| A*3601 | 84 | --- | --- |
| A*4301 | 85 | --- | --- |
| A*6601 | 86 | --- | --- |
| A*6602 | 87 | --- | --- |
| A*68011 | 88 | --- | --- |
| A*68012 | 89 | --- | --- |
| A*6802 | 90 | --- | --- |
| A*6901 | 91 | --- | --- |
| A*7401 | 92 | --- | --- |
| * | 93 | AGCCGCGGGGCCGCCCGTGGATAGAGCAGGAGGGGCCGGAGTATTGGG | |
| A*0101 | 53 | ---A--- | --- |
| A*0201 | 54 | ---G------TA---G--- | ---T--- |
| A*0202 | 55 | ---G------AG---G--- | ---T---C |
| A*0203 | 56 | ---G------AG---G--- | ---T---C |
| A*0204 | 57 | ---G------AG---G--- | ---T---C |
| A*0205 | 58 | ---G------AG---G--- | ---T---C |
| A*0206 | 59 | ---G------AG---G--- | ---T---C |
| A*0210 | 60 | ---G------AG---G--- | ---T---C |
| A*0211 | 61 | ---G------AG---G--- | ---T---C |
| A*0212 | 62 | ---G------TG---G--- | ---T---C |
| A*0301 | 63 | ---A--- | --- |
| A*0302 | 64 | ---A------TG---G--- | ---GT--- |
| A*1101 | 65 | ---A--- | --- |
| A*1102 | 66 | ---A------TG---G--- | ---GT--- |
| A*2301 | 67 | ---GA-----AG---GG--- | ---T--- |
| A*2401 | 68 | ---GA-----AG---GG--- | ---T--- |
| A*2402 | 69 | ---GA-----AG---GG--- | ---T--- |
| A*2403 | 70 | ---GA-----AG---GG--- | ---T--- |
| A*2501 | 71 | ---A--C---TG---G--- | ---T--- |
| A*2601 | 72 | ---A--C---AG---G--- | --- |
| A*2901 | 73 | ---T--C---TG---G--- | ---T--- |
| A*2902 | 74 | ---T--C---TG---G--- | ---T--- |
| A*3001 | 75 | ---A------TG---G--- | ---GT--- |
| A*3002 | 76 | ---A------TG---G--- | ---GT--- |
| A*3003 | 77 | ---A------TG---G--- | ---GT--- |
| A*31011 | 78 | ---A------AG---G--- | ---T--- |
| A*31012 | 79 | ---A------AG---G--- | ---T--- |
| A*3201 | 80 | ---A--C---TG---G--- | ---T--- |
| A*3301 | 81 | ---A--C---TG---G--- | ---T--- |
| A*3401 | 82 | ---A--C---AG---G--- | --- |
| A*3402 | 83 | ---A------TA---G--- | ---T--- |
| A*3601 | 84 | ---T--C---TG---G--- | ---T--- |
| A*4301 | 85 | ---T--C---TG---G--- | ---T--- |
| A*6601 | 86 | ---A------TG---G--- | ---GT--- |

TABLE 1A-continued

Exon 2

| | Seq ID No. | | | 240 | | 260 | |
|---|---|---|---|---|---|---|---|
| A*6602 | 87 | ---- | --A--C | ---- | --G---- | --TG--G | ---GT---- |
| A*68011 | 88 | ---- | --A--C | ---- | --G---- | --TG--G | ---GT---- |
| A*68012 | 89 | ---- | --A--C | ---- | --G---- | --TG--G | ---GT---- |
| A*6802 | 90 | ---- | --A--C | ---- | --G---- | --TG--G | ---GT---- |
| A*6901 | 91 | ---- | --A--C | ---- | --G---- | --TG--G | ---GT---- |
| A*7401 | 92 | ---- | --A---- | ---- | --G---- | --TG--G | ----T---- |
| * | 93 | ACCGGGAGACACAGAACTTCAAGGCCCACACAGACTGACCGAG |

| | Seq ID No. | | | 240 | | 260 | |
|---|---|---|---|---|---|---|---|
| A*0101 | 53 | C---- | ---- | --G---- | --C---- | ---- | ---- |
| A*0201 | 54 | T--G | ---- | --G---- | --C---- | ---- | ---- |
| A*0202 | 55 | T--G | ---- | --G---- | --C---- | ---- | ---- |
| A*0203 | 56 | T--G | ---- | --G---- | --C---- | ---- | ---- |
| A*0204 | 57 | T--G | ---- | --G---- | --C---- | ---- | ---- |
| A*0205 | 58 | T--G | ---- | --G---- | --C---- | ---- | ---- |
| A*0206 | 59 | T--G | ---- | --G---- | --C---- | ---- | ---- |
| A*0210 | 60 | T--G | ---- | --G---- | --C---- | ---- | ---- |
| A*0211 | 61 | T--G | ---- | --G---- | --C---- | ---- | ---- |
| A*0212 | 62 | T--G | ---- | --G---- | --C---- | ---- | ---- |
| A*0301 | 63 | T--G | ---- | --G---- | --C---- | ---- | ---- |
| A*0302 | 64 | T--G | ---- | --G---- | --C---- | ---- | ---- |
| A*1101 | 65 | T--G | ---- | --G---- | --C---- | ---- | ----A |
| A*1102 | 66 | T---- | ---- | --G---- | --C---- | ---- | ---- |
| A*2301 | 67 | ---- | ---- | ---- | --T--GC | --T--C | ---- |
| A*2401 | 68 | ---- | ---- | ---- | --T--GC | --T--C | ---- |
| A*2402 | 69 | ---- | ---- | ---- | --T--GC | --T--C | ---- |
| A*2403 | 70 | ---- | ---- | ---- | --T--GC | --T--C | ---- |
| A*2501 | 71 | ---- | --G | ---- | --T--GC | --C---- | ---- |
| A*2601 | 72 | C---- | ---- | --G---- | --C---- | ---- | ----A |
| A*2901 | 73 | C---- | ---- | ---- | ---- | ---- | ---- |
| A*2902 | 74 | C---- | ---- | ---- | ---- | ---- | ----A |
| A*3001 | 75 | T--G | ---- | --G---- | --C---- | ---- | ----A |
| A*3002 | 76 | ---- | ---- | --G---- | --C---- | ---- | ---- |
| A*3003 | 77 | ---- | --G | ---- | ---- | ---- | ---- |
| A*31011 | 78 | T--G | ---- | --G---- | --C---- | ---- | ---- |
| A*31012 | 79 | T--G | ---- | --G---- | --C---- | ---- | ---- |
| A*3201 | 80 | ---- | --G | ---- | --T--GC | --T--C | ---- |
| A*3301 | 81 | T--G | ---- | --G---- | --C---- | ---- | ----A |
| A*3401 | 82 | T--G | ---- | --G---- | --C---- | ---- | ----A |
| A*3402 | 83 | T--G | ---- | --G---- | --C---- | ---- | ----A |
| A*3601 | 84 | C---- | ---- | --G---- | --C---- | ---- | ----A |
| A*4301 | 85 | C---- | ---- | --G---- | --C---- | ---- | ----A |
| A*6601 | 86 | T--G | ---- | --G---- | --C---- | ---- | ---- |
| A*6602 | 87 | T--G | ---- | --G---- | --C---- | ---- | ---- |
| A*68011 | 88 | T--G | ---- | --G---- | --C---- | ---- | ---- |
| A*68012 | 89 | T--G | ---- | --G---- | --C---- | ---- | ---- |
| A*6802 | 90 | T--G | ---- | --G---- | --C---- | ---- | ---- |
| A*6901 | 91 | T--G | ---- | --G---- | --C---- | ---- | ---- |
| A*7401 | 92 | T--G | ---- | --G---- | --C---- | ---- | ---- |
| * | 93 | AGAACCTGCGGAACCTGCGCGGCTACTACAACCAGAGCGAGGCCG |

*Consensus Sequence

TABLE 1B

Exon 3

| | Seq ID No. | 1 | | 20 | | 40 | |
|---|---|---|---|---|---|---|---|
| A*0101 | 94 | ------------- | -T-- | ----------A--- | TA--- | --------------- | ------ |
| A*0201 | 95 | ------------- | -T-- | ----------G--- | ----- | --------------- | ------ |
| A*0202 | 96 | ------------- | -T-- | --------------- | ----- | --------------- | ------ |
| A*0203 | 97 | ------------- | -T-- | ----------G--- | --T-- | --------------- | ------ |
| A*0204 | 98 | ------------- | -T-- | ----------G--- | ----- | --------------- | ------T |
| A*0205 | 99 | ------------- | -T-- | --------------- | ----- | --------------- | ------T |
| A*0206 | 100 | ------------- | -T-- | ----------G--- | ----- | --------------- | ------T |
| A*0210 | 101 | ------------- | -T-- | ----------G--- | ----- | --------------- | ------T |
| A*0211 | 102 | ------------- | -T-- | ----------G--- | ----- | --------------- | ------T |
| A*0212 | 103 | ------------- | -T-- | ----------G--- | ----- | --------------- | ------T |
| A*0301 | 104 | ------------- | -T-- | ----------A--- | TA--- | --------------- | ------T |
| A*0302 | 105 | ------------- | -T-- | ----------A--- | TA--- | --------------- | ------T |
| A*1101 | 106 | ------------- | -T-- | ----------A--- | TA--- | --------------- | ------T |
| A*1102 | 107 | ------------- | -T-- | ----------A--- | T---- | --------------- | ------T |
| A*2301 | 108 | ------------- | -T-- | --------------- | --T-- | --------------- | ------T |
| A*2401 | 109 | ------------- | -T-- | --------------- | --T-- | --------------- | ------T |
| A*2402 | 110 | ------------- | -T-- | --------------- | --T-- | --------------- | ------T |
| A*2403 | 111 | ------------- | -T-- | --------------- | --T-- | --------------- | ------T |
| A*2501 | 112 | ------------- | -T-- | ----------A--- | ----- | --------------- | ------ |
| A*2601 | 113 | ------------- | -T-- | ----------A--- | --T-- | --------------- | ------ |
| A*2901 | 114 | ------------- | -T-- | ----------A--- | --T-- | ---------C----- | --T--- |
| A*2902 | 115 | ------------- | -T-- | ----------A--- | --T-- | --------------- | --T--- |
| A*3001 | 116 | ------------- | -T-- | ----------A--- | TA--- | --------------- | --T--- |
| A*3002 | 117 | ------------- | -T-- | ----------A--- | TA--- | --------------- | --T--- |
| A*3003 | 118 | ------------- | -T-- | ----------A--- | TA--- | --------------- | --T--- |
| A*31011 | 119 | ------------- | -T-- | ----------A--- | TA--- | --------------- | --T--- |
| A*31012 | 120 | ------------- | -T-- | ----------A--- | ----- | --------------- | --T--- |
| A*3201 | 121 | ------------- | -T-- | ----------A--- | --T-- | --------------- | --T--- |
| A*3301 | 122 | ------------- | -T-- | ----------A--- | --T-- | --------------- | --T--- |
| A*3401 | 123 | ------------- | -T-- | ----------A--- | TA--- | --------------- | --T--- |
| A*3402 | 124 | ------------- | -T-- | ----------A--- | TA--- | --------------- | --T--- |
| A*3601 | 125 | ------------- | -T-- | ----------A--- | ----- | --------------- | --T--- |
| A*4301 | 126 | ------------- | -T-- | ----------A--- | ----- | --------------- | --T--- |
| A*6601 | 127 | ------------- | -T-- | ----------A--- | ----- | --------------- | --T--- |
| A*6602 | 128 | ------------- | -T-- | ----------A--- | --T-- | --------------- | --T--- |
| A*68011 | 129 | ------------- | -T-- | --------------- | --T-- | --------------- | --T--- |
| A*68012 | 130 | ------------- | -T-- | ----------A--- | --T-- | --------------- | ------- |
| A*6802 | 131 | ------------- | -T-- | ----------A--- | --T-- | --------------- | ------- |
| A*6901 | 132 | ------------- | -T-- | --------------- | ----- | --------------- | --T--- |
| A*7401 | 133 | ------------- | -T-- | ----------G--- | --T-- | --------------- | --T--- |
| * | 134 | GGTCTCACACCCT | CACC | CCTCCAGAGGATG | TATGG | CTGCGACGTGGGG | CCGGA |

| | Seq ID No. | | | 60 | | 80 | |
|---|---|---|---|---|---|---|---|
| A*0101 | 94 | | | | | | |
| A*0201 | 95 | | | ---G--- | | CCGG--- | |
| A*0202 | 96 | | | ------- | | CC----- | |
| A*0203 | 97 | | | ---G--- | | CC----- | |
| A*0204 | 98 | | | ------- | | CC----- | |
| A*0205 | 99 | | | ---G--- | | CC----- | |
| A*0206 | 100 | | | ------- | | CC----- | |

TABLE 1B-continued

| Allele | # | Sequence |
|---|---|---|
| A*0210 | 101 | ---T----------------------------------CC--- |
| A*0211 | 102 | -T--T---------------------------------CC--- |
| A*0212 | 103 | -T--T---------------------------------CC--- |
| A*0301 | 104 | ----T-------------------------------CCGG---G--- |
| A*0302 | 105 | ----T-------------------------------CCGG---G--- |
| A*1101 | 106 | ----T-------------------------------CCGG---G--- |
| A*1102 | 107 | ----T---------------------------------CC------G--- |
| A*2301 | 108 | ----T---------------------------------CC--- |
| A*2401 | 109 | ----T---------------------------------CC--- |
| A*2402 | 110 | ----T---------------------------------CC--- |
| A*2403 | 111 | ----T---------------------------------CC--- |
| A*2501 | 112 | ----T---------------------------------CC---G---T |
| A*2601 | 113 | ----T---------------------------------CC---G---T |
| A*2901 | 114 | ----T-------------------------------CCGG---G--- |
| A*2902 | 115 | ----T-------------------------------CCGG---G--- |
| A*3001 | 116 | ----T---------------------------------CC-A-C--- |
| A*3002 | 117 | ----T---------------------------------G-A---C--- |
| A*3003 | 118 | ----T---------------------------------G-A---C--- |
| A*31011 | 119 | ----T---------------------------------CC---G--- |
| A*31012 | 120 | ----T---------------------------------CC---G--- |
| A*3201 | 121 | ----T---------------------------------CC---G--- |
| A*3301 | 122 | ----T---------------------------------CC---G--- |
| A*3401 | 123 | ----T---------------------------------CC---G---T |
| A*3402 | 124 | ----T-------------------------------CCGG---G--- |
| A*3601 | 125 | ----T---------------------------------CC---G---T |
| A*4301 | 126 | ----T---------------------------------CC---G---T |
| A*6601 | 127 | ----T---------------------------------CC---G---T |
| A*6602 | 128 | ----T-------------------------------CCGG---G--- |
| A*68011 | 129 | ----T---------------------------------CC---G--- |
| A*68012 | 130 | ----T-------------------------------CCGG---G--- |
| A*6802 | 131 | -T--T---------------------------------CC--- |
| A*6901 | 132 | ----T---------------------------------CC--- |
| A*7401 | 133 | ---T----------------------------------CC-G--- |
| * | 134 | CGGGCGCCTCCTCCGCGGGTATAACCAGTAACGCCTACGACGGCAAG |

TABLE 1C

Exon 2

| | Seq ID No. | 1                                             10              20                30              40       |
|---|---|---|
| * | 135 | G S H S M R Y F Y T S V S R P G R G E P R F I A V G Y V D D T Q F V R F D S D A A S P R M |
| A*0101 | 135 | — — — — — — — — — — — — — — — — — — — — — — — — — — — — — — — — — — — — — — — — Q K — |
| A*0201 | 136 | — — — — — — — F — — — — — — — — — — — — — — — — — — — — — — — — — — — — — — — — — Q — |
| A*0202 | 137 | — — — — — — — F — — — — — — — — — — — — — — — — — — — — — — — — — — — — — — — — — — R |
| A*0203 | 138 | — — — — — — — F — — — — — — — — — — — — — — — — — — — — — — — — — — — — — — — — — Q — |
| A*0204 | 139 | — — — — — — — F — — — — — — — — — — — — — — — — — — — — — — — — — — — — — — — — — Q — |
| A*0205 | 140 | — — — — — — — F — — — — — — — — — — — — — — — — — — — — — — — — — — — — — — — — — Q — |
| A*0206 | 141 | — — — — — — — F — — — — — — — — — — — — — — — — — — — — — — — — — — — — — — — — — R — |
| A*0210 | 142 | — — — — — — — — — — — — — — — — — — — — — — — — — — — — — — — — — — — — — — — — — Q — |
| A*0211 | 143 | — — — — — — — — — — — — — — — — — — — — — — — — — — — — — — — — — — — — — — — — — Q — |
| A*0212 | 144 | — — — — — — — — — — — — — — — — — — — — — — — — — — — — — — — — — — — — — — — — — Q — |
| A*0301 | 145 | — — — — — — — F — — — — — — — — — — — — — — — — — — — — — — — — — — — — — — — — — Q — |
| A*0302 | 146 | — — — — — — — F — — — — — — — — — — — — — — — — — — — — — — — — — — — — — — — — — Q — |
| A*1101 | 147 | — — — — — — — — — — — — — — — — — — — — — — — — — — — — — — — — — — — — — — — — — Q — |
| A*1102 | 148 | — — — — — — — — — — — — — — — — — — — K — — — — — — — — — — — — — — — — — — — — — Q — |
| A*2301 | 149 | — — — — — — — — — S — — — — — — — — — — — — — — — — — — — — — — — — — — — — — — — Q — |
| A*2401 | 150 | — — — — — — — — — S — — — — — — — — — — — — — — — — — — — — — — — — — — — — — — — Q — |
| A*2402 | 151 | — — — — — — — — — S — — — — — — — — — — — — — — — — — — — — — — — — — — — — — — — Q — |
| A*2403 | 152 | — — — — — — — — — S — — — — — — — — — — — — — — — — — — — — — — — — — — — — — — — Q — |
| A*2501 | 153 | — — — — — — — — — S — — — — — — — — — — — — — — — — — — — — — — — — — — — — — — — Q — |
| A*2601 | 154 | — — — — — — — — — — — — — — — — — — — — — — — — — — — — — — — — — — — — — — — — — Q — |
| A*2901 | 155 | — — — — — — — — — T — — — — — — — — — — — — — — — — — — — — — — — — — — — — — — — Q — |
| A*2902 | 156 | — — — — — — — — — T — — — — — — — — — — — — — — — — — — — — — — — — — — — — — — — Q — |
| A*3001 | 157 | — — — — — — — — — F — — — — — — — — — — — — — — — — — — — — — — — — — — — — — — — Q — |
| A*3002 | 158 | — — — — — — — — — S — — — — — — — — — — — S — — — — — — — — — — — — — — — — — — — Q — |
| A*3003 | 159 | — — — — — — — — — S — — — — — — — — — — — S — — — — — — — — — — — — — — — — — — — Q — |
| A*3101 | 160 | — — — — — — — — — S — — — — — — — — — — — S — — — — — — — — — — — — — — — — — — — Q — |
| A*3201 | 161 | — — — — — — — — — T — — — — — — — — — — — — — — — — — — — — — — — — — — — — — — — Q — |
| A*3301 | 162 | — — — — — — — — — F — — — — — — M — — — — — — — — — — — — — — — — — — — — — — — — Q — |
| A*3401 | 163 | — — — — — — — — — T — — — — — — — — — — — — — — — — — — — — — — — — — — — — — — — Q — |
| A*3402 | 164 | — — — — — — — — — F — — — — — — — — — — — — — — — — — — — — — — — — — — — — — — — Q — |
| A*3601 | 165 | — — — — — — — — — — — — — — — — — — — — — — — — — — — — — — — — — — — — — — — — Q K — |
| A*4301 | 166 | — — — — — — — — — — — — — — — — — — — — — — — — — — — — — — — — — — — — — — — — — Q — |
| A*6601 | 167 | — — — — — — — — — — — — — — — — — — — — — — — — — — — — — — — — — — — — — — — — — Q — |
| A*6602 | 168 | — — — — — — — — — — — — — — — — — — — — — — — — — — — — — — — — — — — — — — — — — Q — |
| A*6801 | 169 | — — — — — — — — — F — — — — — — — — — — — — — — — — — — — — — — — — — — — — — — — Q — |
| A*6802 | 170 | — — — — — — — — — — — — — — — — — — — — — — — — — — — — — — — — — — — — — — — — — Q — |
| A*6901 | 171 | — — — — — — — — — F — — — — — — — — — — — — — — — — — — — — — — — — — — — — — — — Q — |
| A*7401 | 172 | — — — — — — — — — — — — — — — — — — — — — — — — — — — — — — — — — — — — — — — — — Q — |
| | 173 | — — — — — — — — — — — — — — — — — — — — — — — — — — — — — — — — — — — — — — — — — — — |

| | Seq ID No. | 50                60                70                80                90 |
|---|---|---|
| * | 135 | E P R A P W I E Q E G P E Y W D R E T Q I V K A N T Q T D R E S L R N L R G Y Y N Q S E A |
| A*0101 | 135 | — — — — — — — — — — — — — — — — — — — — — — — — — — — — — — — — — — — — — — — — — — — D |
| A*0201 | 136 | — — — — — — — — — — — — — — — — — — — — — — — — — — — Q — — — — — — — — A N — — — — — G T |
| A*0202 | 137 | — — — — — — — — — — — — — — — — — — — — — R K — — — — — — — — — H S — — — V D — — — G T |
| A*0203 | 138 | — — — — — — — — — — — — — — — — — — — — — R K — — — — — — — — — H S — — — V D — — — G T |
| A*0204 | 139 | — — — — — — — — — — — — — — — — — — — — — R K — — — — — — — — — H S — — — V D — — — G T |
| A*0205 | 140 | — — — — — — — — — — G — — — — — — — — — — R K — — — — — — — — — H S — — — V D — — — G T |
| A*0206 | 141 | — — — — — — — — — — G — — — — — — — — — — R K — — — — — — — — — H S — — — V D — — — G T |
| A*0210 | 142 | — — — — — — — — — — G — — — — — — — — — — R K — — — — — — — — — H S — — — V D — — — G T |

TABLE 1C-continued

| | | Exon 2 | | | | |
|---|---|---|---|---|---|---|
| A*0211 | 144 | — | — | G — — R K — — H S — I — V D — G T — — — | — |
| A*0212 | 145 | — | — | G — — R K — — H S — H — V D — G T — — — | — |
| A*0301 | 146 | — | — | Q — — R N — — Q S — — — V D — G T — — — | — |
| A*0302 | 147 | — | — | Q — — R N — — Q S — — — V D — G T — — — | — |
| A*1101 | 148 | — | — | Q — — R N — — Q S — — — V D — G T — — — | D |
| A*1102 | 149 | — | — | Q — — R N — — Q S — — — V D — G T — — — | D |
| A*2301 | 150 | — | — | E — — G K — — H S — — — N — — — I A L R | — |
| A*2401 | 151 | — | — | E — — G K — — H S — — — N — — — I A L R | — |
| A*2402 | 152 | — | — | E — — G K — — H S — — — N — — — I A L R | — |
| A*2403 | 153 | — | — | E — — G K — — H S — — — N — — — I A L R | — |
| A*2501 | 154 | — | — | — N — R N — — H S — — — A N — G T — — — | D |
| A*2601 | 155 | — | — | — N — R N — — Q S — — — A N — G T — — — | — |
| A*2901 | 156 | — | — | L Q — R N — — Q S — — — A N — G T — — — | — |
| A*2902 | 157 | — | — | L Q — R N — — Q S — — — A N — G T — — — | — |
| A*3001 | 158 | R | — | Q — — R N — — H S — — — V D — G T — — — | — |
| A*3002 | 159 | R | — | Q — — R N — — H S — — — V D — G T — — — | — |
| A*3003 | 160 | — | — | Q — — R N — — H S — — — N — — G T — — — | — |
| A*3101 | 161 | R | — | — Q — R N — — H S — I — V D — G T — — — | — |
| A*3102 | 162 | — | — | — Q — R N — — H S — — — N — — — I A L R | — |
| A*3301 | 163 | — | — | — N — R N — — H S — I — V D — G T — — — | — |
| A*3401 | 164 | — | — | — N — R K — — Q S — — — V D — G T — — — | D |
| A*3402 | 165 | — | — | — N — R N — — Q S — — — V D — G T — — — | D |
| A*3601 | 166 | — | — | Q — — R N M — H S — — — A N — G T — — — | D |
| A*4301 | 167 | — | — | L Q — R N — — H S — — — A N — G T — — — | — |
| A*6601 | 168 | — | — | — N — R N — — Q S — — — V D — G T — — — | D |
| A*6602 | 169 | — | — | — N — R N — — Q S — — — V D — G T — — — | D |
| A*6801 | 170 | — | — | — N — R N — — Q S — — — V D — G T — — — | — |
| A*6802 | 171 | — | — | — N — R N — — Q S — — — V D — G T — — — | — |
| A*6901 | 172 | — | — | — N — R N — — Q S — — — V D — G T — — — | — |
| A*7401 | 173 | — | — | Q — — R N — — H S — — — V D — G T — — — | — |

*Consensus Sequence

TABLE 1D

Exon 3

```
                   90        100       110       120       130
                    |         |         |         |         |
*        GSHTLQRMYGCDVGPDGRLLRGYDQYAYDGKDYIALNEDLRSWTAA
A*0101  174 ------I-------------F------R--D------------
A*0201  175 ------V-------S--W--F------R--D------------
A*0202  176 ------V-------S--W--F------H---------------
A*0203  177 ------V-------S--W--F------H---------------
A*0204  178 ------V-------S--W--F------H---------------
A*0205  179 ------V----M--S--W--F------H---------------
A*0206  180 ------V-------S--W--F------H------------K--
A*0210  181 ------V-------S--W--F------H------------K--
A*0211  182 ------V-------S--W--F------H------------K--
A*0212  183 ------V-------S--W--F------H------------K--
A*0301  184 ------V-------S--W--F------H------------K--
A*0302  185 ------I-------S-----F------R--D---------K--
A*1101  186 ------I-------S-----F------R--D---------K--
A*1102  187 ------I-------S-----F------R--D---------K--
A*2301  188 ------I-------S-----F------R--D------------
A*2401  189 ------M--F----S-----F------H---------------
A*2402  190 ------M--F----S-----F------H---------------
A*2403  191 ------M--F----S-----F------H---------------
A*2501  192 ------M--F----S-----F------Q--D------------
A*2601  193 ------I-------S-----F------Q--D---------K--
A*2901  194 ----M-I----H--S-----F------R--D------------
A*2902  195 ----M-I-------S-----F------R--D------------
A*3001  196 ----M-I-------S-----F------R--D------------
A*3002  197 ----M-I----T--S--HE-F------E--H------------
A*3003  198 ----M-I-------S-----F------E--H------------
A*3101  199 ------I-------S-----F------E--H------------
A*3201  200 ----M-M-------S-----F------Q--D------------
A*3301  201 ----M-M-------S-----F------Q--D------------
A*3401  202 ------M-------S-----F------Q--D------------
A*3402  203 ------I-------S-----F------Q--D------------
A*3601  204 ------I-------S-----F------R--D------------
A*4301  205 ------I-------------F------R--D------------
A*6601  206 ----M-M-------S-----F------Q--D---------K--
A*6602  207 ----M-M-------------F------Q--D---------K--
A*6801  208 ------M-------S-----F------R--D---------K--
A*6802  209 ------I-------S-----F------H------------K--
A*6901  210 ------I-------------F------H---------------
A*7401  211 ----V-M-------S--W--F------H---------------
A*0210  212 ----I-M-------S--W--F------Q--D------------
```

```
                  140       150       160       170       180
                   |         |         |         |         |
*       DTAAQITQRKWEAARVAEQLRAYLEGTCVEWLRRYLENGKETLQRA
A*0101  174 ----------------------------------------------
A*0201  175 --M----K-----VHA-----R-V------R--DR---------T
A*0202  176 --M----T-KH----H-------------------------T
A*0203  177 --M----T-KH----W-------------------------T
A*0204  178 --M----T-KH----W-------------------------T
A*0205  179 --M----T-KH--T-HE------------------------T
A*0206  180 --M----T-KH----H-------------------------T
A*0210  181 --M----T-KH----H-------------------------T
A*0212  182 --M----T-KH----H-------------------------T
```

TABLE 1D-continued

Exon 3

| Allele | # | Sequence |
|---|---|---|
| A*0211 | 183 | -M------T-KH-------H----------------T |
| A*0212 | 184 | -M------T-KH-------H---Q------------T |
| A*0301 | 185 | -M--------K--------HE--------D-------T |
| A*0302 | 186 | -M--------K--------H---------D-------T |
| A*1101 | 187 | -M--------K--------HA----R-----------T |
| A*1102 | 188 | -M--------K--------HA----R-----------T |
| A*1301 | 189 | -M-----------------H---Q----------DG--T |
| A*2401 | 190 | -M--------K--------H---Q----------DG--T |
| A*2402 | 191 | -M--------K--------H---Q----------DG--T |
| A*2403 | 192 | -M--------K--------H---Q-------------T |
| A*2501 | 193 | -M-------------T--HE---W---R---------T |
| A*2601 | 194 | -M-------------T--HE---W---R---------T |
| A*2901 | 195 | -M-----------------------------------T |
| A*2902 | 196 | -M-----------------W------------------T |
| A*3001 | 197 | -M-----------------R------------------T |
| A*3002 | 198 | -M-----------------R-----R-----------T |
| A*3003 | 199 | -M-----------------R------------------T |
| A*3101 | 200 | -M------------------------------------T |
| A*3201 | 201 | -M------------------------------------T |
| A*3301 | 202 | -M----------------DE---W-------------T |
| A*3401 | 203 | -M-------------T--HE---W-------------T |
| A*3402 | 204 | -M-------------T--HE---W-------------T |
| A*3601 | 205 | -M--------K-------VHA--R-V-----------T |
| A*4301 | 206 | -M-------------T--HE---R---R---------T |
| A*6601 | 207 | -M-------------T--HE---W---R---------T |
| A*6602 | 208 | -M-------------T--HE---W---E---------T |
| A*6801 | 209 | -M------T-KH---------H---W-----------T |
| A*6802 | 210 | -M------T-KH---------H---W-----------T |
| A*6901 | 211 | -M------T-KH---------H--------------H-T |
| A*7401 | 212 | -M-------------------H---------------T |

*Consensus Sequence

The DNA sequences provided above are an important aspect of the present invention. Although only one strand of the sequence is shown, those of skill in the art will recognize that the complementary strand of each sequence can be inferred from the information depicted above. This information enables the construction of probes of the invention in addition to the exemplified probes.

Probes

In the methods of the present invention, the HLA-A alleles are detected and distinguished using sequence-specific oligonucleotide probes. The typing probes of the invention specifically detect the allelic sequence variations.

The extensive sequence diversity of the HLA-A alleles is spread out over the second and third exons, unlike that of the Class II beta genes, which is localized to the second exon. In general, the pattern of second and third exon sequence polymorphism is a patchwork, with specific region sequence variants found in a variety of different alleles. For purposes of HLA-A genotyping, this patchwork pattern of polymorphism means that many alleles cannot be identified by hybridization to a single oligonucleotide probe but can be identified by a unique pattern of hybridization with a panel of probes.

Preferred sets of sequence-specific probes for detecting sequences variation in the second and third exons of the HLA-A locus are provided in Table 2A and 2B, below. The tables provide the amino acid epitope which corresponds to the nucleic acid sequence variation to be detected, the amino acid position, and the hybridizing region of the probe (shown 5' to 3'). The amino acid positions are numbered as in Tables 1C and 1D, above.

TABLE 2A

HLA-A Exon 2 Typing Probes

| Probe | Seq ID No. | Epitope | A.A. | Sequence |
|---|---|---|---|---|
| DB436 | 1 | YFYTS | 5–14 | ATGAGGTATTTCTACACCTCCG |
| DB350* | 2 | YFFRS | 5–12 | ACGGATGTGAAGAAATACCTC |
| DB315* | 3 | YFTTS | 5–12 | GGATGTGGTGAAATACCTC |
| RAP215 | 4 | YFSTS | 5–12 | ATGAGGTATTTCTCCACATCCG |
| RAP207 | 5 | RGKPR | 17–21 | GGGAAGCCCCGCTTC |
| DB455* | 6 | AASQR | 40–46 | TCCATCCTCTGGCTCGCG |
| DB456 | 7 | AASQK | 42–46 | CGCGAGCCAGAAGATGGAG |
| DB457* | 8 | AASRR | 40–46 | TCCATCCTCCGGCTCGC |
| DB213 | 9 | QERPE | 54–58 | GAGCAGGAGAGGCCTGAGTA |
| RAP216 | 10 | WDGET | 60–65 | GGAGTATTGGGACCAGGAGAC |
| DB469* | 11 | WDGET | 60–65 | TGTCTCCCCGTCCCAATACTCC |
| DB411 | 12 | WDGET | 60–65 | GAGTATTGGGACGAGGAGAC |
| DB461* | 13 | WDLQT | 60–65 | CCGTGTCTGCAGGTCCCAATA |
| RAP220 | 14 | WDRNT | 60–65 | GTATTGGGACCGGAACACAC |
| DB464 | 15 | TRNMK | 64–68 | GAGACACGGAATATGAAGGCC |
| DB442* | 16 | TRNVK | 64–68 | TGGGCCTTCACATTCCGTGT |
| DB471* | 17 | TGKVK | 64–68 | GGGCCTTCACTTTCCCTGT |
| RAP205 | 18 | KAHSQ | 68–72 | TGAAAGGCCCACTCACAGACT |
| RAP206* | 19 | KAQSQ | 68–72 | GTCTGTGACTGGGCCTTCA |
| DB463 | 20 | HRVDL | 74–78 | CAGACTCACCGAGTGGACCT |
| RAP24* | 21 | DRVDL | 74–78 | CCAGGTCCAGTCGGTCAGTC |
| RAP22 | 22 | DRANL | 74–78 | GACTGACCGAGCGAACCTG |
| RAP21 | 23 | DRENL | 74–78 | GACTGACCGAGAGAACCTG |
| RAP221* | 24 | DRESL | 74–78 | CGCAGGCTCTCTCGGTC |
| DB414 | 25 | IALR | 80–94 | GATCGCGCTCCGCTACTAC |

*Probe is from non-coding strand

TABLE 2B

HLA-A Exon 3 Typing Probes

| Probe | Seq ID No: | Epitope | A.A. | Sequence |
|---|---|---|---|---|
| RAP244* | 26 | GSHTIQ | 91–96 | GGTTCTCACACCATCCAGAG |
| DB367 | 27 | GSHTLQ | 91–96 | CCTCCAGATGATGTTTGGC |
| DB363 | 28 | LQMMFG | 95–100 | GGTTCTCACACCCTCCAG |
| RAP261 | 29 | TIQIM | 94–98 | TCTCACACCATCCAGATAATGTA |
| DB362* | 30 | HTVQRM | 93–98 | ACATCCTCTGGACGGTGTG |
| RAP227* | 31 | HTIQMM | 93–98 | ATACATCATCTGGATGGTGAGAGA |
| RAP300 | 32 | HTVQMM | 93–98 | TCATCTGGACGGTGTGAGAC |
| RAP262 | 33 | SDWRFG | 105–110 | TCGGACTGGCGCTTC |
| RAP265* | 34 | SDGRF | 105–110 | AGCGCCCGTCCGAC |
| RAP248 | 35 | GYHQY | 112–117 | GCGGGTACCACCAGTACG |
| RAP233 | 36 | GYEQH | 112–117 | GGGTATGAACAGCACGCC |
| RAP249 | 37 | YQQDA | 112–117 | GGTACCAGCAGGACGC |
| RAP252 | 38 | QITQR | 141–156 | TGCGCTGGGTGATCTG |
| RAP270 | 39 | QITKRK | 141–156 | CAGATCACCAAGCGCAA |
| RAP64 | 40 | QTTKHK | 149–154 | CTCAGACCACCAAGCACAAG |
| RAP238 | 41 | VHA | 150–152 | GCGGTCCATGCGGC |
| RAP272 | 42 | AAHVA | 148–154 | AGGCGGCCCATGTG |
| RAP255* | 43 | EAAHEA | 148–154 | CCTCATGGGCCGCC |
| RAP256 | 44 | ETAHEA | 148–154 | GAGACGGCCCATGAGG |
| RAP287 | 45 | EQLRAY | 154–159 | GAGCAGTTGAGAGCCTAC |
| RAP278* | 46 | EQQRAY | 154–159 | TAGGCTCTCTGCTGCTCC |
| RAP280 | 47 | EQWRAY | 154–159 | GGTAGGCTCTCCACTGCTC |
| RAP283 | 48 | EQRRVY | 154–159 | AGGTAGACTCTCCGCTGCT |
| RAP257 | 49 | EGRCV | 161–165 | GAGGGCCGGTGCGT |

TABLE 2B-continued

HLA-A Exon 3 Typing Probes

| Probe | Seq ID No: | Epitope | A.A. | Sequence |
|---|---|---|---|---|
| RAP290 | 50 | CVDGL | 164–168 | CGGAGCCCGTCCACA |

*Probe is from non-coding strand

In the exemplified typing system, only 36 of the 37 distinct alleles which encode amino acid sequence variations are considered to be unique alleles. The alleles 2901 (Seq ID Nos. 73 and 114) and 2902 (Seq ID Nos. 74 and 115) are not distinguished in the exemplified typing system. These alleles are very rare and it may be of limited value to distinguish between them. The 2901/2902 (Seq ID Nos. 73 and 114/Seq ID Nos. 74 and 115) allele group is treated herein as a single allele. However, if desired, an additional sequence-specific probe can be designed using the sequence information provided above that will distinguish alleles 290 1 (Seq ID Nos. 73 and 114) and 2902 (Seq ID Nos. 74 and 115).

The alleles that are considered unique alleles for the purpose of present invention are the following HLA alleles:

0101 (Seq ID Nos. 53 and 94), 0201 (Seq ID Nos. 54 and 95), 0202 (Seq ID Nos. 55 and 96), 0203 (Seq ID Nos. 56 and 97), 0204 (Seq ID Nos. 57 and 98), 0205 (Seq ID Nos. 58 and 99), 0206 (Seq ID Nos. 59 and 100), 0210 (Seq ID Nos. 60 and 101), 0211 (Seq ID Nos. 61 and 102), 0212 (Seq ID Nos. 62 and 103), 0301 (Seq ID Nos. 63 and 104), 0302 (Seq ID Nos. 64 and 105), 1101 (Seq ID Nos. 65 and 106), 1102 (Seq ID Nos. 66 and 107), 2301 (seq ID Nos. 67 and 108), 2401/02 (Seq ID Nos. 68 and 109/

Seq ID Nos. 69 and 110), 2403 (Seq ID Nos. 70 and 111), 2501 (Seq ID Nos. 71 and 112), 2601 (Seq ID Nos. 72 and 113), 2901/02 (Seq ID Nos. 73 and 114/Seq ID Nos. 74 and 115), 3001 (Seq ID Nos. 75 and 116), 3002 (Seq ID Nos. 76 and 117), 3003 (Seq ID Nos. 77 and 118), 3101 (Seq ID Nos. 78, 79, 119, and 120), 3201 (Seq ID Nos. 80 and 121), 3301 (Seq ID Nos. 81 and 122), 3401 (Seq ID Nos. 82 and 123), 3402 (Seq ID Nos. 83 and 124), 3601 (Seq ID Nos. 84 and 125), 4301 (Seq ID Nos. 85 and 126), 6601 (Seq ID Nos. 86 and 127), 6602 (Seq ID Nos. 87 and 128), 6801 (Seq ID Nos. 88, 89, 129, and 130), 6802 (Seq ID Nos. 90 and 131), 6901 (Seq ID Nos. 91 and 132), 7401 (Seq ID Nos. 92 and 133)

The probes provided enable the detection and discrimination of 31 out of the 36 homozygous genotypes and 602 out of the 630 possible heterozygous genotypes. The pattern of probe hybridization is easily obtained by comparing the sequence of each allele with each probe sequence, and is provided in FIG. 1. Similarly, the pattern of probe hybridization for each of the 630 possible heterozygous genotypes is obtained by combining the individual allele hybridization patterns. The genotype of an unknown sample is the determined by comparing the pattern of probe hybridization with the possible probe hybridization patterns. A computer program to generate the possible hybridization patterns and to perform the comparisons necessary to determine an unknown genotype is easily written. The use of such a program is described in Example 3, below.

The probes provided in Tables 2A and 2B are designed so that each probe will hybridize to a specific target sequence under the same stringent hybridization conditions and stay hybridized under the same wash conditions as all other probes in the set. In the reverse dot blot methods described in the Examples, an entire panel of probes may be immobilized on a single membrane. The hybridization and wash steps are carded out for all probes in a panel simultaneously. One set of hybridization conditions is effective for the sequence-specific hybridization of all the probes in a panel shown in Tables 2A and 2B.

Several variable regions have the property in the typing system of the present invention that 3 or more probes are used to distinguish the nucleotide variation present and the variation is such that it is not possible for more than 2 probes to hybridize, even with a heterozygous sample. This provides a check for contamination in the system. If more than 2 probes hybridize, then the sample must be contaminated with additional nucleic acid sequences. The variable regions of the second exon of the HLA-A gene are region A (codons 5 to 12), region B, (codons 40 to 46), region C (codons 60 to 65), region D (codons 64 to 68), and region E (codons 74–78). The variable regions of the third exon of the HLA-A gene are region F (codons 93 to 98), region G (codons 112 and 117), region H (codons 141 to 154), region I (codons 148 to 154), and region J (codons 154–159).

The probes for detecting the allelic variation hybridize either to the allele sequences shown in Tables 1A and 1B, or to the complements of the allele sequences shown in Tables 1A and 1B. One of skill in the art will realize that, for detecting double-stranded target DNA, the complement of each suitable sequence-specific probe is also a suitable sequence-specific probe.

Primers

In a preferred embodiment of the invention, the process for determining the HLA-A genotype comprises amplifying a polymorphic region which includes the entire second and third exons of the HLA-A locus, preferably using PCR, determining the variant HLA-A allele sequence present by hybridization with sequence-specific probes; and inferring the HLA-A genotype from the pattern of binding of the probes to the amplified target sequence. Preferred primers for the PCR amplification of the HLA-A target region are shown in Table 3. The first primer, RAP1007 (Seq ID No. 51), hybridizes upstream of the first exon of A locus; the second primer, DB337 (Seq ID No. 52), hybridizes to the end of the third exon. These primers amplify a 990 base-pair (bp) fragment. An important feature of the preferred primers is that they do not coamplify other HLA Class I loci, which could interfere with the accurate typing of the A locus alleles.

TABLE 3

| | HLA-A Amplification Primers | |
|---|---|---|
| Primer | Seq ID No. | Sequence |
| RAP1007 | 51 | 5'-AGGATCCAGACGCCGAGGATGGCCG |
| DB337 | 52 | 5'-CAGGATCCCTCCTTCCCGTTCTCCAGGT |

Any type of tissue containing HLA-A nucleic acid may be used for determining the HLA-A genotype of an individual; the methods are not limited to typing cells which express the HLA-A gene. Simple and rapid methods of preparing samples for PCR are described in Higuchi, 1989, in PCR Technology (Erich ed., Stockton Press, New York). Because the genotyping methods of the present invention can utilize amplified nucleic acids, and because the PCR technique can amplify extremely small quantities of nucleic acid, the HLA-A genotype can be determined even from samples containing only a few copies of the HLA-A gene. For instance, even a single hair contains enough DNA for purposes of the present invention, as evidenced by the DQ DNA typing methods described by Higuchi et al., 1988, supra. The feasibility of using single sperm for DNA typing is demonstrated in Li et al, 1988, Nature 335:441–417.

In general, the nucleic acid in the sample will be DNA, most usually genomic DNA. However, the present invention can also be practiced with other nucleic acids, such as messenger RNA or cloned DNA, and the nucleic acid may be either single-stranded or double-stranded in the sample and still be suitable for purposes of the present invention. Those skilled in the an recognize that whatever the nature of the nucleic acid, the nucleic acid can be typed by the present method merely by taking appropriate steps at the relevant stage of the process. If PCR is used to amplify the nucleic acid in the sample, then the sample will usually comprise double-stranded DNA after amplification and before probe hybridization.

The polymerase chain reaction (PCR) amplification process is well known in the art and described in U.S. Pat. Nos. 4,683,195; 4,683,202; and 4,965,188, each incorporated herein by reference, and in Saiki et al., 1988, Science 239:487; Scharf et al., 1988, Hum. Immunol. 22:61; and Scharf et al., 1989, Proc. Natl. Acad. Sci. USA 86:6215, each incorporated herein by reference. Commercial vendors, such as Perkin Elmer, Norwalk, Conn., market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

Due to the enormous amplification possible with the PCR process, small levels of DNA carryover from samples with high DNA levels, positive control templates, or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. Sec also Higuchi and Kwok, 1989, Nature 339:237–238 and Kwok, and Orrego, in: Innis et al. eds., 1990 PCR Protocols: A Guide to Methods and Applications, Academic Press, Inc., San Diego, Calif., which are incorporated herein by reference.

Enzymatic methods to reduce the problem of contamination of a PCR by the amplified nucleic acid from previous reactions are described in PCT Patent Publication No. WO 92/01814 and U.S. Pat. No. 5,035,996, both incorporated herein by reference. The methods allow the enzymatic degradation of any amplified DNA from previous reactions. PCR amplifications are carded out in the presence of dUTP instead of dTTP. The resulting double-stranded amplification product which incorporates uracil is subject to degradation by uracil-N-glycosylase (UNG), whereas normal thymine-containing DNA is not degraded by UNG. Amplification reaction mixture are treated with UNG before amplification to degrade all uracil containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-innactivated environment and are not degraded.

Although the polymerase chain reaction is the preferred amplification method, amplification of target sequences in a sample may be accomplished by any known method, such as ligase chain reaction (Wu and Wallace 1988, Genomics 4:560–569, incorporated herein by reference), the TAS amplification system (Kwoh et al., 1989, Proc. Natl. Acad. Sci. USA 86:1173–1177, incorporated herein by reference), and self-sustained sequence replication (Guatelli et al., 1990, Proc. Natl. Acad. Sci. USA 87:1874–1878, incorporated herein by reference), each of which provides sufficient amplification so that the target sequence can be detected by nucleic acid hybridization to an SSO probe. Alternatively, methods that amplify the probe to detectable levels can be used, such as Qβ-replicase amplification (Kramer and Lizardi, 1989, Nature 339:401–402, and Lorneli et al., 1989, Clin. Chem. 35:1826–1831, both of which are incorporated herein by reference). A review of known amplification methods is provided in Abramson and Myers, 1993, Current Opinion in Biotechnology 4:41–47, incorporated herein by reference. The term "probe," as used herein, encompasses the sequence-specific oligonucleotides used in the above procedures;

for instance, the two or more oligonucleotides used in LCR are "probes" for purposes of the present invention, even though some embodiments of LCR only require ligation of the probes to indicate the presence of an allele.

Amplification of the DNA sequences of the alleles of the HLA-A gene is a useful, but not a necessary, step in determining the HLA-A genotype of an individual. Specific probe hybridization, however, is an important step in successful performance of the present methods. The sequence-specific oligonucleotide probes of the present invention are designed to be complementary to one of the particular variant sequences which define the HLA-A alleles. The SSO probes, when used under stringent hybridization conditions wherein probes hybridize only to exactly complementary sequences, enable the detection and discrimination of the HLA-A alleles. Suitable stringent hybridization conditions, which will depend on the exact size of the probe and placement of the target region to which the probe hybridizes, can be selected empirically using the guidance provided in the prior art.

The assay methods for detecting hybrids formed between SSO probes and target nucleic acid sequences can require that the probes contain additional features in addition to the hybridizing region. For example, probes can be labeled to permit detection or bound to an additional compound to facilitate immobilization of the probe. Such additional features incorporated into the probes to allow detection or immobilization should not affect the hybridization properties of the probes which enable the detection and discrimination of HLA-A alleles.

Probes can be labeled by incorporating a label detectable by spectroscopic, photochemical, biochemical, immunochemical, or chemical means. Useful labels include $^{32}P$, fluorescent dyes, electron-dense reagents, enzymes (as commonly used in ELISAS), biotin, or haptens and proteins for which antisera or monoclonal antibodies are available.

Labeled probes of the invention can be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for SSO probes is horseradish peroxidase (HRP). Methods for preparing and detecting probes containing this label are described in the Examples, below, and in U.S. Pat. Nos. 4,914,210, and 4,962,029; both incorporated herein by reference. The use of such labeled probes is also described in U.S. Pat. No. 4,789,630; Saiki et al., 1988, *N. Eng. J. Med.* 319:537-541; Bugawan et al., 1988, *Bio/Technology* 6:943-947; and Levenson and Chang, 1989, in *PCR Protocols: A Guide to Methods and Applications* (Innis, Gelfand, Sninsky and White ed., Academic Press, Inc. San Diego), each of which is incorporated herein by reference. Useful chromogens for the detection of HRP labeled probes include red leuco dye and 3,3',5,5'-tetramethylbenzidine (TMB).

Examples of additional compounds which can be incorporated into probes to allow immobilization of the probes include a long poly-dT "tail" that can be fixed to a nylon support by irradiation, a technique described in more detail in PCT Patent Publication No. 89/11548, incorporated herein by reference.

The probes of the invention are used to identify the allelic sequences present in a sample by determining which probes hybridize to the HLA-A sequences present in the sample. Suitable assay methods for detecting hybrids formed between probes and target nucleic acid sequences in a sample are known in the art (Sambrook et al., 1985, supra). Examples include the dot blot and reverse dot blot assay formats.

In a dot blot format, unlabeled amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

An alternate format is a "reverse" dot blot format, in which the amplified target DNA is labeled and the probes are immobilized on a solid support, such as a nylon membrane (see Saiki et al., 1989, *Proc. Natl. Acad. Sci. USA* 86:6230, and copending U.S. Ser. No. 347,495, filed May 4, 1989, both incorporated herein by reference). The target DNA is typically labeled during amplification by the incorporation of labeled primers. The membrane-probe complex is incubated with the labeled sample under suitable hybridization conditions, unhybridized sample is removed by washing under suitably stringent conditions, and the filter is then monitored for the presence of bound target DNA.

Alternatively, the reverse dot blot assay may be carried out using a solid support having a plurality of probe hybridization sites or wells. For example, a microwell plate is particularly useful in large scale clinical applications of the present methods. A reverse dot blot assay utilizing a microwell plate is described in copending U.S. Ser. No. 695,072, filed May 3, 1991, which is a CIP of U.S. Ser. No. 414,542, filed Nov. 20, 199 1, now abandoned, both incorporated herein by reference. Probes can be immobilized to a microwell plate either by passive binding or by first binding the probes to bovine serum albumen (BSA), which adheres to microwell plates.

Another suitable assay method system is described in U.S. Pat. No. 5,210,015, incorporated herein by reference, in which a labeled probe is added during the PCR amplification process. The probes are modified so as to prevent the probe from acting as a primer for DNA synthesis. Any probe which hybridizes to target DNA during each synthesis step is degraded by the 5' to 3' exonuclease activity of the DNA polymerase, e.g., Taq DNA polymerase. The degradation product from the probe is then detected. Thus, the presence of probe breakdown product indicates that hybridization between probe and target DNA occurred.

Whatever the method for determining which SSO probes of the invention hybridize to HLA-A allelic sequences in a sample, the central feature of the typing method involves the identification of the HLA-A alleles present in the sample by analyzing the pattern of binding of target DNA to a panel of SSO probes. The specific application will determine which probes are used in a panel. For instance, if only the presence or absence of a specific allele is of interest, a subset of the typing probes may be adequate.

DNA typing of HLA-A alleles is useful for many different purposes. For example, the typing methods of the present invention can be used to discover new alleles. New alleles have additional variation such that the pattern of sequence-specific probe hybridization is not a pattern previously observed. The existence of an new allele can then be confirmed by direct sequencing of the PCR products from the above amplification or by cloning the PCR products and sequencing the clones. Suitable sequencing methods are known in the art (Sambrook et al., 1985, supra).

The typing methods of the invention have valuable clinical applications. The Class I gene products of the major histocompatibility complex (MHC) function as restriction elements in the presentation of mainly endogenous peptides to cytotoxic T lymphocytes and are a major barrier for allogeneic tissue transplantation. Hence, the HLA-A genotyping system will be valuable in typing potential transplantation donors, where very precise HLA matching appears to be critical in minimizing risk of rejection or graft versus host disease. Additionally, the HLA-A genotyping system will allow the identification of alleles associated with an increased risk of disease.

Another application of the typing system of the invention is in identifying the source of a biological sample. DNA typing methods now play a significant role in the important area of individual identification, whether for solving crimes, as when the identity of a criminal or victim is established by linking an individual with evidence left at the scene of a crime, or for solving other issues of a non-criminal nature, as when biological material is used to determine the maternity or paternity of an individual.

The present invention also relates to kits, multicontainer units comprising useful components for practicing the present method. A useful kit can contain SSO probes for the HLA-A alleles. In some cases, the SSO probes may be fixed to an appropriate support membrane. The kit can also contain primers for PCR amplification, as such primers are useful in the preferred embodiment of the invention. These primers will amplify a polymorphic region of the HLA-A locus. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

PCR Amplification of HLA-A Genomic DNA

The following protocol is for the PCR amplification of between 250–500 ng of genomic DNA in 100 μl reactions volumes. Each reaction contains the following reagents:

50 mM KCl,
10 mM Tris-HCL (pH 8.4),
1.5 mM MgCl$_2$,
100 μg/ml Gelatin,
175 μM each dATP, cdTP, dGTP and dTTP,
0.30 μM each of the biotinylated amplification primers,
3.0 units of Taq DNA polymerase*, and
20% Glycerol.

* manufactured and developed by Hoffmann-La Roche and marketed by Perkin Elmer (Norwalk, Conn.)

The primers RAP1007 (Seq ID No. 51) and DB337 (Seq ID No. 52) are used to amplify a 990 base pair region that includes exons 2 and 3 of the HLA-A locus. Each primer is biotinylated for use in the reverse dot blot detection method described in Example 2, below.

Amplifications were carded out in a DNA thermal cycler (Perkin Elmer, Norwalk, Conn.) using 35 cycles of the following three-step temperature cycle:
denature at 95° C. for 1 minute,
anneal at 65° C. for 1 minute, and
extend at 72° for 30 seconds.

EXAMPLE 2

Detection of Amplified HLA-A DNA

Reverse Dot Blot Format In this embodiment of the invention, the HLA-A probes are immobilized on a membrane, and the amplified target DNA is hybridized to the membrane-bound probe as described in Saiki et al., 1989, Proc. Natl. Acad. Sci. 86:6230–6234, and in the AmpliType DQalpha DNA Typing Kit, developed and manufactured by Hoffmann-La Roche and marketed by Perkin Elmer, Norwalk, Conn., both incorporated herein by reference.

Amplification is carded out essentially as in Example 1. The primers are biotinylated as described in Levenson and Chang, 1989, supra. Note that one or both of the primers can be biotinylated.

Detection is carded out by reacting streptavidin conjugated horseradish peroxidase (SA-HRP) with any biotinylated, amplified DNA hybridized to the membrane-bound probe. The HRP, which becomes bound through the SA-biotin interaction to the amplified DNA, is used to generate a signal by any of a variety of well know means, such as by the oxidation of tetramethylbenzidine (TMB) (see U.S. Pat. No. 4,789,630).

Although the probes can be fixed to the membrane by any means, a preferred method involves "tailing" an oligonucleotide probe with a long sequence of poly-dT. The resulting poly-dT "tail" can then be reacted with amine groups on the membrane to fix the probe covalently to the membrane. This reaction can be facilitated by UV irradiation.

Poly-dT tailed probes can be created either using terminal deoxyribonucleotidyl transferase (TdT, Ratliff Biochemicals) or synthesized using a commercially available DNA synthesizer. If a DNA synthesizer is used to make the tailed probe, the tail should be synthesized on the 5' end of the probe, so that undesired premature chain termination occurs primarily in the tail region.

Poly-dT tails are added to probes using TdT as follows. TdT reactions are carried out in a 100 μl reaction containing 200 pmole of oligonucleotide probe, 0.8 mM dTT, 60 units of TdT, and 1X TdT salts (100 mM K-cacodylate, 1 mM COCl$_2$, 0.2 mM dithiothreitol, 25 mM Tris-Cl, pH 7.6, prepared as described by Roychoudhury and Wu, 1980, Meth. Enzymol. 65:43–62, incorporated herein by reference). The TdT reaction is carded out at 37° C. for two hours and then stopped by the addition of 100 μl of 10 mM EDTA, pH 8. The final concentration of tailed oligonucleotide is 1 μM (1 pmole/μl), and the length of the homopolymer tail is about 400 residues. Tail length can be changed by adjusting the molar ratio of dTTP to oligonucleotide. The tailed probes can be stored at −20° C. until use.

Two preferred nylon membrane strips for the reverse dot blot format are the Biodyne ™ nylon membrane, 0.45 micron pore size (Pall Corp., Glen Cove, N.Y.) and the Biotrans ™ nylon membrane, 0.45 micron pore size (ICN, Irvine, Calif.). The probes can be spotted onto the strip conveniently with the Gibco dot blot apparatus (Gibco, Gaithersburg, Md.). Probes are spotted on discrete locations on the strip. About 8 picomoles of each tailed probe is premixed with 42 µl of IX TE before application to the dot blot apparatus. After dot blotting, the strip is briefly placed on absorbent paper to draw off excess liquid. The strip is then placed inside a UV light box, such as the Stratalinker ™ light box (Stratagene, La Jolla, Calif.) and exposed to 50 millijoules/cm$^2$ of flux at 254 nm to fix the tailed probe to the nylon strip. After a brief rinse (about 15 minutes in hybridization solution) to remove unbound probe, the strip is ready for hybridization with biotinylated PCR product.

Hybridization reactions are carried out in an Amplitype DNA typing tray (Perkin Elmer, Norwalk, Conn.). The probe-membrane strips are placed in the typing tray and 3 ml of hybridization solution (3X SSPE and 0.5% (w/v) SDS) are added to each probe strip. About 35 µl of PCR reaction mixture is added to each probe strip. Hybridization is carded out at 50° C. for 30 minutes in a rotating water bath.

Alter hybridization, a stringent wash is carried out. The contents of each tray are aspirated and 5 ml of wash solution (1X SSPE and 0.1% (w/v) SDS) are added. The tray is incubated at 50° C. for 10 minutes in a rotating water bath, and the wash solution is then aspirated. Following the stringent wash, the probe strips are rinsed with 5 ml of wash solution, and the wash solution is aspirated.

An enzyme conjugate solution is prepared by adding 100 µl of enzyme conjugate (SA-HRP, available from Perkin Elmer, Norwalk, Conn.) to 3.3 ml of wash solution for each probe strip. Each probe strip is soaked in 3 ml of the enzyme conjugate solution and incubated at room temperature for 30 minutes on an orbital shaker.

The enzyme conjugate is aspirated, the probe strips are washed in 5 ml of wash solution at room temperature on an orbital shaker, and the wash solution is then aspirated. The probe strips are then rinsed in 100 mM citrate buffer (0.1M Sodium Citrate, pH 5.0).

For color development, each membrane is incubated in a solution of 48 ml of citrate buffer, 23 µl of 3% hydrogen peroxide, and 2.5 ml Chromogen:TMB Solution (Perkin Elmer, Norwalk, Conn.). The strips are developed in the dark at room temperature for 20–30 minutes on an orbital shaker (50 rpm). The color development solution is aspirated and development is stopped by washing the strips in 5 ml glass-distilled water for 5 to 10 minutes in an orbital shaker (50 rpm). The wash step is repeated at least twice, preferably more.

The HLA-A type of the sample is determined from the pattern of probe hybridization. If a permanent record is desired, the probe strips should be photographed while still wet.

EXAMPLE 3

HLA-A Genotyping

HLA-A genotyping of 22 human cell lines was carded out essentially as described in Examples 1 and 2, above. PCR amplifications were carded out using the primers provided in Table 3, and the reverse dot blot allele detection was carded out using the sequence-specific oligonucleotide probe panels of Tables 2A and 2B. The cell lines had previously been characterized serologically.

The HLA-A genotype of the sample was inferred from the pattern of probe hybridization. The expected pattern of hybridization for each allele is provided in FIGS. 1 and 2; the sample genotype is inferred from a comparison of the assay results to the expected results. A simple computer program which performs the pattern comparison was designed and used for allele assignment. Hybridization patterns observed for each cell line were as expected.

We claim:

1. A method for amplifying a region of the HLA-A locus containing the first and second exons, wherein said method consists of carrying out a polymerase chain reaction using oligonucleotide primers RAP1007 (SEQ ID NO: 51) and DB337 (SEQ ID NO: 52).

2. A pair of oligonucleotide primers for amplifying a region of the HLA-A locus containing the first and second exons, wherein said pair of primers consists of oligonucleotide primers RAP1007 (SEQ ID NO: 51) and DB337 (SEQ ID NO: 52).

* * * * *